US012396821B2

(12) United States Patent
Colle

(10) Patent No.: US 12,396,821 B2
(45) Date of Patent: Aug. 26, 2025

(54) DEVICES FOR ASSISTING NEUROSURGICAL INTERVENTIONS

(71) Applicants: Henry Colle, Drongen (BE); David Colle, Sint-Denijs-Westrem (BE)

(72) Inventor: Henry Colle, Drongen (BE)

(73) Assignees: Henry Colle, Drongen (BE); David Colle, Sint-Denijs-Westrem (BE)

( * ) Notice: Subject to any disclaimer, the term of this patent is extended or adjusted under 35 U.S.C. 154(b) by 416 days.

(21) Appl. No.: 17/998,140

(22) PCT Filed: May 7, 2021

(86) PCT No.: PCT/EP2021/062093
§ 371 (c)(1),
(2) Date: Nov. 7, 2022

(87) PCT Pub. No.: WO2021/224440
PCT Pub. Date: Nov. 11, 2021

(65) Prior Publication Data
US 2023/0225820 A1 Jul. 20, 2023

(30) Foreign Application Priority Data
May 8, 2020 (EP) ..................................... 20173644

(51) Int. Cl.
*A61B 90/14* (2016.01)
*A61B 90/11* (2016.01)
*A61B 17/00* (2006.01)

(52) U.S. Cl.
CPC .............. *A61B 90/14* (2016.02); *A61B 90/11* (2016.02); *A61B 2017/00712* (2013.01)

(58) Field of Classification Search
CPC ......... A61B 34/20; A61B 34/30; A61B 90/10; A61B 34/70; A61B 2034/2055; A61B 90/14; A61B 2090/101; A61B 90/11
See application file for complete search history.

(56) References Cited

U.S. PATENT DOCUMENTS

| 5,423,832 A | 6/1995 | Gildenberg |
| 10,548,681 B2 | 2/2020 | Seong et al. |

(Continued)

FOREIGN PATENT DOCUMENTS

| EP | 1681029 A1 | 7/2006 |
| GB | 818711 A | 8/1959 |

(Continued)

OTHER PUBLICATIONS

International Search Report and Written Opinion issued for International Patent Application No. PCT/EP2021/062093, dated Nov. 24, 2021 in 24 pages.

*Primary Examiner* — Katherine M Shi
(74) *Attorney, Agent, or Firm* — Knobbe, Martens, Olson & Bear, LLP

(57) ABSTRACT

Provided is a system for positioning an intermediate head clamp (300) on a subject for medical interventions on the subject comprising a superior positioning cap (200) configured for placement on a head of the subject having a domed receiving space (222) for receiving a part of the head of the subject, provided with a plurality of adjustable protrusions (260, a, b, c, d, e) to adjust a pose of the superior positioning cap (200);

an inferior positioning support (400) comprising a main body (410) configured for placement around the head of the subject in a region and a plurality of locating bodies (460, 470, 480) each for locating in and engaging with a bodily recesses to adjust the pose of the inferior positioning support (400); wherein the superior positioning cap (200) and inferior positioning support are configured to flank and each engage with the intermediate head clamp (300) such that intermediate head clamp (300) is rotatable around an axis of (Continued)

rotation co-axial with the axes of reference (250, 450) of the superior positioning cap (200) and of the inferior positioning support (400).

8 Claims, 29 Drawing Sheets

(56) References Cited

U.S. PATENT DOCUMENTS

| | | |
|---|---|---|
| 10,595,744 B2 | 3/2020 | Sayler et al. |
| 2010/0268248 A1 | 10/2010 | Hong |
| 2012/0138066 A1 | 6/2012 | Akram et al. |

FOREIGN PATENT DOCUMENTS

| | | |
|---|---|---|
| GB | 2094590 A | 9/1982 |
| WO | 2006/033064 A2 | 3/2006 |

DEVICES FOR ASSISTING NEUROSURGICAL INTERVENTIONS

CROSS-REFERENCE TO RELATED APPLICATIONS

This application is the U.S. National Phase under 35. U.S.C. § 371 of International Application PCT/EP2021/062093, filed May 7, 2021, which claims priority to European Patent Application No. 20173644.4, filed May 8, 2020. The disclosures of the above-described applications are hereby incorporated by reference in their entirety.

FIELD OF THE INVENTION

The present invention is in a field of neurosurgery, in particular of stereotactic neurosurgery.

BACKGROUND TO THE INVENTION

Stereotactic head frames have a long history in neurosurgery. The two most commonly used are the Leksell (Elekta) and CRW (Integra Neurosciences) and ZD system (Inomed). In these procedures, a frame is mounted to the head by screwing pins directly against the patient's skull for fixation at a number points, usually 4. The head with attached frame are then imaged by CT or MRI to identify targets, either manually or more frequently with computerized software, in relation to the external frame. Since both the frame and target can be viewed on the images, the distance of the target from given reference points on the frame can be measured in three coordinates. Next in the operating room, an arc apparatus is attached to the head frame and adjusted based on the previously measured coordinates and desired trajectory. Once in position, a guide is used to introduce a needle through a drill hole along a trajectory to the target.

A problem of the art is the bulkiness of some of the head frames; some medical imaging machines (e.g. MRI) have insufficient tunnel diameter to accommodate the head frame. The bulkiness e.g. of an arc, leads to the need for very long tools (e.g. Leksell frame, CRW frame)). Others extend bilaterally (e.g. ZD system). Another problem is the head frame has to be as close to the head as possible in order to improve stability. Unfortunately, the frame is cumbersome, uncomfortable for patients, and time intensive.

SUMMARY OF THE INVENTION

Provided herein is a system for positioning an intermediate head clamp (300) on a subject for medical interventions thereon, comprising:
a superior positioning cap (200) configured for placement on a head of the subject having a domed receiving space (222) for receiving a part of the head of the subject, wherein the superior positioning cap (200) is provided with a plurality of adjustable protrusions (260, a, b, c, d, e), each configured for controlled advancement into the domed receiving space or withdrawal therefrom and for contacting a part of the head of the subject, wherein the plurality of adjustable protrusions (260, a, b, c, d, e) adjusts a pose of the superior positioning cap (200) and of an axis of reference (250) of the superior positioning cap (200) in relation to the head,
an inferior positioning support (400) comprising a main body (410) configured for placement around the head of the subject in a region coinciding with the forehead, and a plurality of locating bodies (460, 470, 480) each for locating in and engaging with a bodily recesses and each locating body (460, 470, 480) being attached in adjustable and fixable in positional relation to the main body (410) of the inferior positioning support (400), wherein the plurality of locating bodies (460, 470, 480) adjusts the pose of the inferior positioning support (400) and of an axis of reference (450) of the inferior positioning support (400) in relation to the head,
wherein the superior positioning cap (200) and inferior positioning support are configured to flank and each engage with the intermediate head clamp (300) such that the axes of reference (250, 450) of the superior positioning cap (200) and of the inferior positioning support (400) are co-axial, and intermediate head clamp (300) is rotatable around an axis of rotation co-axial with the axes of reference (250, 450) of the superior positioning cap (200) and of the inferior positioning support (400).

Each of the superior positioning cap (200), and inferior positioning support (400) may comprise a movement guide (246, 340) configured to co-operate with a complementary movement guide (346, 346') disposed respectively on superior and inferior sides of the intermediate head clamp (300), the movement guides having a circular or arc path centred on the coaxial arrangement of the axes of reference (250, 450) and axis of rotation (350).

The system may further comprise the intermediate head clamp (300), wherein the intermediate clamp comprises a main body (310), a holding space (322) at least partially surrounded by the main body (310) dimensioned to receive the head of the subject, a plurality of clamps (390, a-d) each configured for advancement into the holding space (322) or withdrawal therefrom and for contacting the part of the head of the subject, wherein deployment of the plurality of clamps (390, a-d) fixes a pose of the main body (310) relative to the head of the subject.

The intermediate head clamp (300) may be provided with at least one intermediate head clamp, IHC, hub (380, 380') configured for dismountable attachment of at least one arc-shaped intermediate head clamp, IHC, supporting rail (382, 382', 382"), wherein the IHC hub (380, 380') is configured to allow rotation of the IHC supporting rail (382, 382', 382") around a rail axis of rotation (385) that crosses the axis of rotation of the intermediate head clamp (300).

The intermediate head clamp (300) main body (310) may be provided with a side opening (324) connecting the holding space (322) to an exterior edge of the main body (310).

The system may further comprise a side-opening bridge (3010) configured for dismountable attachable to the intermediate head clamp (300) body (310) across the side opening (324), wherein the side-opening bridge (3010) is provided with a side-opening bridge, SOB, supporting rail (3020) having an arc-shape and having an arc centre (3012) coinciding with the axis of rotation (350) of the intermediate head clamp (300).

The system may further comprise a further SOB supporting rail (3060) configured for slidable attachment to the SOB supporting rail (3020), wherein the further SOB supporting rail (3060) has an arc-shape having an arc centre coinciding with the arc centre (3012) of the SOB supporting rail (3020), and wherein the arcs of SOB supporting rail (3020) and of the further SOB supporting rail (3060) are perpendicular.

The system may further comprise an instrument holder (384) slidably attached to the further SOB supporting rail (3060), instrument holder (384) configured to fix an instrument direction to coincide with the axis of rotation (350) of the intermediate head clamp (300).

The system may further comprising a marking arc (3070) attached at one end rotatably to the further SOB supporting rail (3060), such that a centre of the marking arc (3070) crosses the axis of rotation (350) of the intermediate head clamp (300), wherein an instrument holder (384) is slidably attached to the marking arc (3070), the instrument holder (384) configured to fix an instrument direction to coincide with the axis of rotation (350) of the intermediate head clamp (300).

Further provided is an intermediate head clamp (300), IHC, support frame (500) comprising a frame base (510) and a moveable member (580) whose position is adjustable and fixable in relation to three orthogonal axes relative the frame base (510), and the frame base (510) is disposed with one or more couplings (519, a, b) for repeatable dismountable attachment of the intermediate head clamp (300), optionally wherein the intermediate head clamp (300) is the intermediate head clamp (300) as defined herein.

The IHC support frame (500) may comprising a kinetic chain of four links (510, 540, 560, 580) connected in series, each link connected to the next link by a prismatic joint, wherein the first link (510) in the chain is the frame base (510), and the last link (580) the moveable member (580), and the second and third links connecting the first and last links together.

At least two of the first link (510), second link (540), and third link (460) may each comprise a pair of parallel bars (512, 514; 542, 544; 562, 564; 562'a, 568b) configured to guide sliding movement of the higher link in the chain, and the pair of parallel bars (512, 514; 542, 544; 562, 564; 562'a, 568b) in said link is mutually rigidly connected by one or more, preferably two interconnecting elements (518a; 518b; 568a, 568b; 568'a, 568'b).

At least one of the prismatic joints may be manually operable, or motorised (electrically, hydraulically or pneumatically) for robotic control.

The IHC support frame (500) may further comprise a dismountable unit (600), wherein the moveable member (580) is disposed with at least one coupling (522, a, b, c) for repeatable dismountable attachment to the dismountable unit (600), wherein the dismountable unit comprises (600):
- a fixed alpha arm, FAA, (610) configured for dismountable attachment in fixed relation to the coupling (522, a, b, c) of the moveable member (580), the fixed alpha arm disposed with an arc-shaped supporting rail, FAA supporting rail (612), having an FAA arc centre for coinciding with a target of treatment of the subject,
- a beta arm, BA, (620) attached in sliding relation to the FAA supporting rail (612), wherein the beta arm (620) is provided with a BA supporting rail (622) configured for slidable attachment of a BA instrument holder (630), the BA supporting rail (612) having an arc-shape, the centre of the arc crossing the centre of the FAA supporting rail arc, wherein the arcs of FAA supporting rail (612) and of the BA supporting rail (622) are perpendicular,
- the BA instrument holder (630), configured for dismountable or non-dismountable attachment of an instrument, the BA instrument holder fixing the instrument direction such that it coincides with the centre of the BA supporting rail arc, or is offset from the centre of the BA supporting rail (622) arc by an offset value to take account of a dimension of BA instrument holder, The IHC support frame (500) may further comprise a dismountable unit (600), wherein the moveable member (580) is disposed with at least one coupling (522, a, b, c) for repeatable dismountable attachment to the dismountable unit (600), wherein the dismountable unit comprises (600):
- at least one moveable member, MM, hub assembly (700) configured for dismountable attachment in fixed relation to the coupling (522, a, b, c) of the moveable member (580) and for dismountable attachment of at least one arc-shaped MM hub supporting rail (720), wherein the MM hub is configured to allow rotation of the MM hub supporting rail (720) around a rail axis of rotation (716) that crosses a target of treatment of the subject,
- at least one MM hub supporting rail (720).

Further provided is an intermediate head clamp (300) comprising:
- a main body (310), a holding space (322) at least partially surrounded by the main body (310) dimensioned to receive the head of the subject, and
- a plurality of clamps (390, a-d) wherein deployment of the plurality of clamps (390, a-d) fixes a pose of the main body (310) relative to the head of the subject, wherein
at least one of the plurality of clamps (390, a-d) comprises
a moveable shaft (392) configured for advancement into the holding space (322) or withdrawal therefrom and for contacting the part of the head of the subject, and a shaft-receiving body (394) for receiving and supporting the moveable shaft (392);
the shaft-receiving body (394) is rotatably attached to the main body (310) for adjustment of the direction of the moveable shaft (392) relative to the main body (310).

The moveable shaft (392) may comprise:
- an outer moveable shaft (392a) moveable in an axial direction (396, A-A') within a passageway (393) of the shaft-receiving body (394),
- an inner moveable shaft (392b), moveable in an axial direction (B-B') within a passageway (3921) of the outer moveable shaft (392a), wherein
a distal end (2) of the outer moveable shaft (392a) is blunt ended for atraumatic contact with skin of the subject's head, and
a distal end (2) of the inner moveable shaft (392b) is pointed (3925) for applying an engaging and locking force to the head to fix the pose of the main body (310) relative to the head of the subject.

The shaft-receiving body (394) may be disposed on a superior side (312) or inferior side (314) of the intermediate head clamp (300), or within a slot (318) disposed within the main body (310).

Further provided is a phantom (800) configured to reproduce a spatial position and optionally orientation of a target in a head of subject comprising:
- a phantom base (810) and a target body (840) whose spatial position and optionally orientation is moveable and fixable relative to the phantom base (810),
- an inferior supporting element (850) configured to support an intermediate head clamp (300) and allow revolute movement of the intermediate head clamp (300) around an axis of reference (855) relative to the phantom base (810), wherein the intermediate head clamp is positionable and fixable around the head of the subject.

The phantom (800) may further comprising the intermediate head clamp (300), wherein the intermediate clamp (300) comprises a main body (310), a holding space (322) at least partially surrounded by the main body (310) dimensioned to receive the head of the subject, a plurality of clamps (390, a-d) each configured for advancement into the holding space (322) or withdrawal therefrom and for contacting the part of the head of the subject, wherein deployment of the plurality of clamps (390, a-d) fixes a pose of the main body (310) relative to the head of the subject, wherein the intermediate head clamp (300) is repeatably dismountably attachable in fixed relation to an intermediate head clamp (300), IHC, support frame (500), and is configured for coupling to the inferior supporting element (850).

The phantom (800) may further comprise the intermediate head clamp (300), IHC, support frame (500) comprising a frame base (510) and a moveable member (580) whose position is adjustable and fixable in relation to three orthogonal axes relative the frame base (510), and the frame base (510) is disposed with one or more couplings (519, a, b) for repeatable dismountable attachment of the intermediate head clamp (300), and the moveable member (580) is disposed with at least one coupling (522, a, b, c) for repeatable dismountable attachment to a dismountable unit (600).

The inferior supporting element (850) may incorporate the inferior positioning support (400) as described elsewhere herein.

FIGURE LEGENDS

FIG. 1 exemplary illustration of a cross-section of the head through median sagittal plane indicating anterior commissure (AC), posterior commissure (PC), AC-PC line, and mid commissural point (MCP) (26), and other structures.

FIGS. 2 & 3 different isometric view of an exemplary superior positioning cap (SPC).

FIGS. 4A to 4C isometric views of an exemplary adjustable protrusions. In FIGS. 4A and 4B a screw thread adjusts the depth. In FIG. 4C, the adjustable protrusion is slidable.

FIGS. 5A & 5B schematic illustrations of an SPC highlighting a movement guide on the inferior side. FIG. 5A shows a plan view, FIG. 7B shows a transverse cross section.

FIGS. 6A and 6B isometric view of different exemplary inferior positioning supports (IPS).

FIGS. 7A & 7B schematic illustrations of an IPS highlighting a movement guide on the superior side. FIG. 7A shows a plan view, FIG. 7B shows a transverse cross section.

FIG. 8 schematic illustration of an IPS depicting a plurality of clamps.

FIG. 9 isometric view of an exemplary intermediate head clamp (IHC).

FIGS. 10A and 10B schematic illustrating a superior side of an IHC, the movement guide, and a plurality of clamps (FIG. 10A only). FIG. 10A shows a plan view, FIG. 10B shows a transverse cross section.

FIGS. 11A and 11B schematic illustrating an inferior side of an IHC, the movement guide, and a plurality of clamps (FIG. 11A only). FIG. 11A shows a plan view, FIG. 11B shows a transverse cross section.

FIG. 12 schematic illustration (plan view) an IHC, showing one IHC hub and one IHC supporting rail.

FIG. 13 schematic illustration (plan view) an IHC, showing two IHC hubs and multiple IHC supporting rails.

FIG. 14 schematic illustration (plan view) an IHC, showing IHC hub and IHC supporting rail and further IHC supporting rail.

FIG. 15 schematic illustration (plan view) an IHC, showing dismountable side-opening bridge (SOB).

FIG. 16 schematic of side-opening bridge (SOB) and further SOB supporting rail.

FIG. 17 schematic of side-opening bridge (SOB) and further SOB supporting rail, the SOB mounted on the side-opening of the IHC.

FIG. 18 schematic view of FIG. 17, in which the further SOB supporting rail revolutely supports a marking (circular) arc.

FIG. 19 isometric view of an IHC coupled with an IPS.

FIG. 20 isometric view of a system comprising IHC coupled with both an IPS and SPC.

FIGS. 21, 22 and 23 shows various views and variations on an IHC support frame.

FIG. 24 isometric view of a dismountable unit that is a fixed alpha arm (FAA) attached to a moveable member, and a beta arm (BA) on the FAA supporting rail.

FIG. 25 isometric view of a dismountable unit that is a moveable member (MM) hub assembly, disposed with a MMH supporting rail that is an arm rest.

FIG. 26 isometric view of a dismountable unit that is a moveable member (MM) hub assembly, disposed with one arc-shaped MMH supporting rail.

FIG. 27 isometric view of a dismountable unit that is a moveable member (MM) hub assembly, disposed with several arc-shaped MMH supporting rails.

FIG. 28 isometric view of a dismountable unit that is a moveable member (MM) hub assembly, disposed with an several arc-shaped MMH supporting rail supporting a further MMH supporting rail (730).

FIG. 29A to D parts of a steerable moveable shaft. FIG. 29A steerable shaft-receiving body;

FIG. 29B moveable shaft; FIG. 29C moveable shaft engaged with shaft-receiving body; FIG. 29D shaft-receiving body with connector to intermediate head clamp (300).

FIG. 30A to D parts of a telescopic moveable threaded shaft. FIG. 30A threaded outer moveable shaft; FIG. 30B threaded inner moveable shaft; FIG. 30C threaded inner moveable shaft recessed within threaded outer moveable shaft; FIG. 30D threaded inner moveable shaft protruding from threaded outer moveable shaft.

FIG. 31A to D parts of a telescopic moveable slidable shaft. FIG. 30A slidable outer moveable shaft; FIG. 30B slidable inner moveable shaft; FIG. 30C slidable inner moveable shaft recessed within slidable outer moveable shaft; FIG. 30D slidable inner moveable shaft protruding from slidable outer moveable shaft.

FIG. 32 isometric view of an IHC provided, in which 4 swivelling shaft-receiving bodies are disposed within a main body of the IHC.

FIG. 33 detailed isometric views of a swivelling shaft-receiving body.

FIG. 34 detailed isometric views of an IHC disposed with a pair of parallel movement guides.

FIG. 35 isometric view of a phantom described herein, with the inferior supporting element separated from the phantom base.

FIG. 36 isometric view of an intermediate head clamp aligned for coupling with the phantom inferior supporting element of FIG. 36.

FIG. 37 detailed isometric view of detailed isometric view of a phantom described herein, with the inferior supporting element attached to the phantom base, aligned with the intermediate head clamp of FIG. 35.

FIG. 38 view of the phantom of FIG. 37, coupled to the intermediate head clamp of FIG. 36.

FIG. 39 isometric view of an IHC frame comprising a dismountable unit containing an alpha and beta arms FIG. 40 view of the IHC frame of FIG. 39, coupled to the intermediate head clamp of FIG. 36.

FIG. 41 view of the phantom of FIG. 38, in which it is coupled to the intermediate head clamp of FIG. 36, and wherein the intermediate head clamp is also attached to the IHC frame base.

DETAILED DESCRIPTION OF INVENTION

Figure 1:
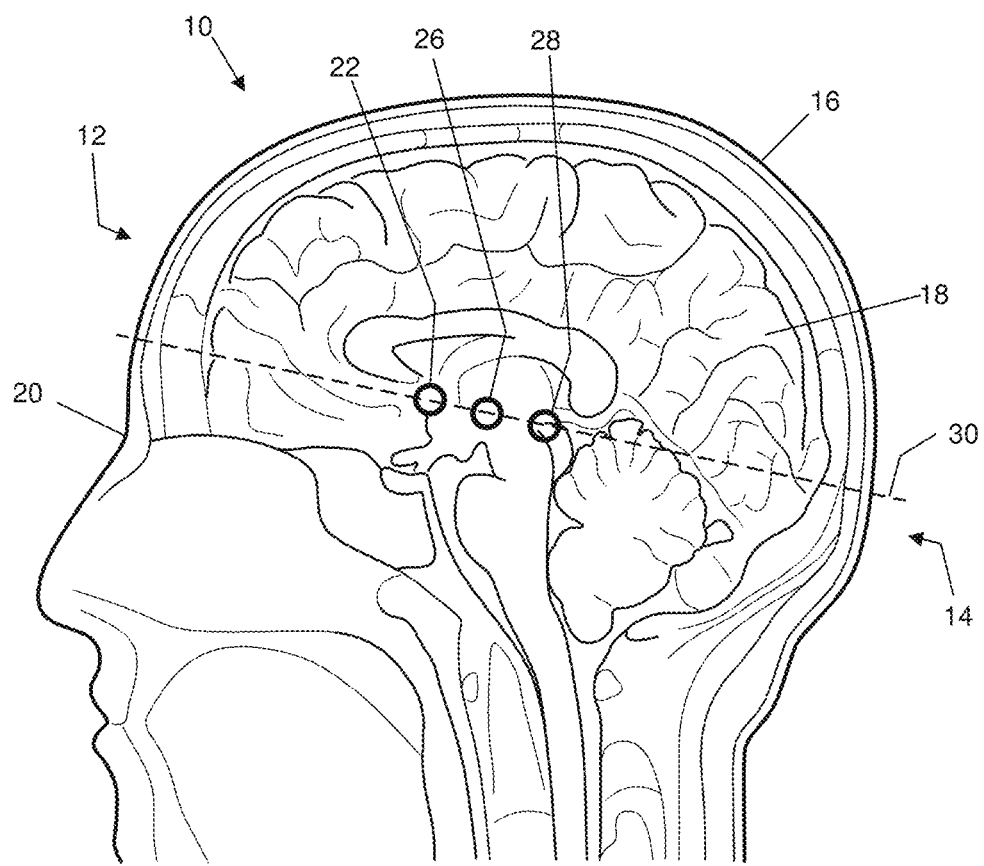

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms superior, inferior, lateral, anterior, and posterior have been used here according to their ordinary meaning with respect to a body of a subject. The terms superior and inferior refer mean towards the head (vertex) and towards the feet respectively of an subject in particular when one of the superior positioning cap (200), intermediate head clamp (300), or inferior positioning support (400) is mounted or to be on the subject's head. The terms anterior and posterior means towards the front and towards the back respectively of the subject. The term lateral means towards the exterior of an upright subject. The term pose herein refers to a position (e.g. with respect to axis of displacement) and orientation (e.g. with respect to 2 or 3 axes of rotation) of an object. The pose may be determined relative to a positional reference such as the head or mid-commissural point (MCP) (26).

FIG. 1 is an exemplary illustration of a cross-section of the head (16) (through median sagittal plane) of a subject (10) typically obtained by medical imaging. In the brain (18), the anterior commissure (AC) (22) and posterior commissure (PC) (24) are determined from which an AC-PC line (30) is known. A midpoint of the AC (22) and PC (24) along the AC-PC line (30) is determined, which is also mid commissural point (MCP) (26). This MCP (26) is considered to be the centre of the brain. Also indicated is the nasion (460), the anterior side (20) and posterior side (14).

Figure 20:
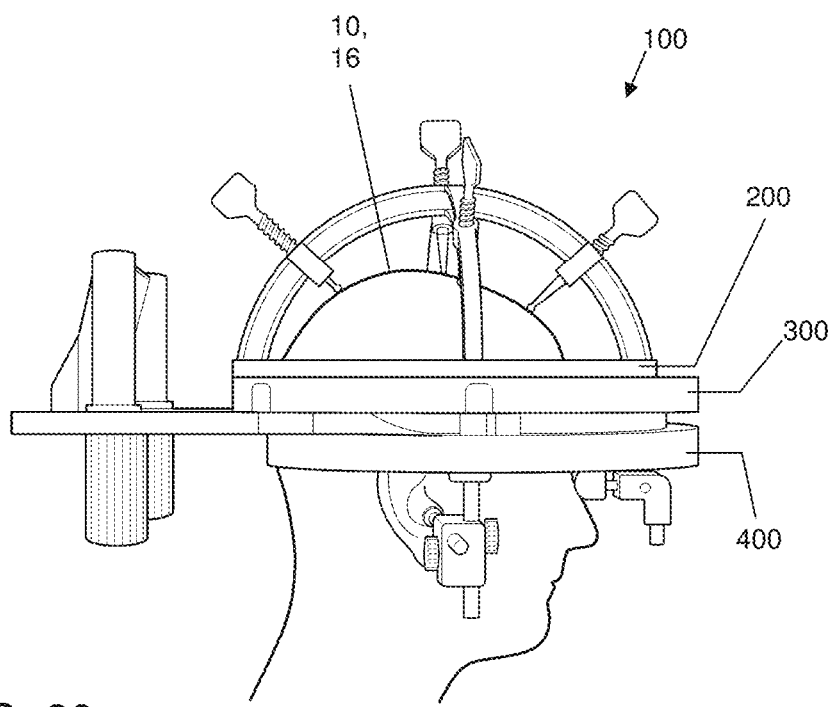

Provided herein is a system (100) for accurately positioning a head clamp (300) (also known as an intermediate head clamp (IHC) (300)) on a subject (10) for medical interventions on the head of the subject (e.g. neurosurgical interventions, including open surgery, and stereotactic interventions). The system comprises a superior positioning cap (200), and an inferior positioning support (400), wherein a pose of the intermediate head clamp (300) is set by the flanking superior positioning guide (SPC) (200) and inferior positioning support (IPS) (400), and the intermediate head clamp (300)) is rotatable therebetween. A system (100) in which the SPC (200), IHC (300) and IPS (400) are coupled together on a head of a subject is shown in FIG. 20.

Further provided is a localiser for positioning a moveable member relative to the head clamp for accurate positioning of instruments and supports with respect to a surgical target.

Further provided is an intermediate head clamp (IHC) (300) adapted for optimal fixation to the head of the subject at a desired pose.

Further provided is a phantom for reproducing the spatial position of the target for treatment of the subject relative to the intermediate head clamp (300).

Figure 2:
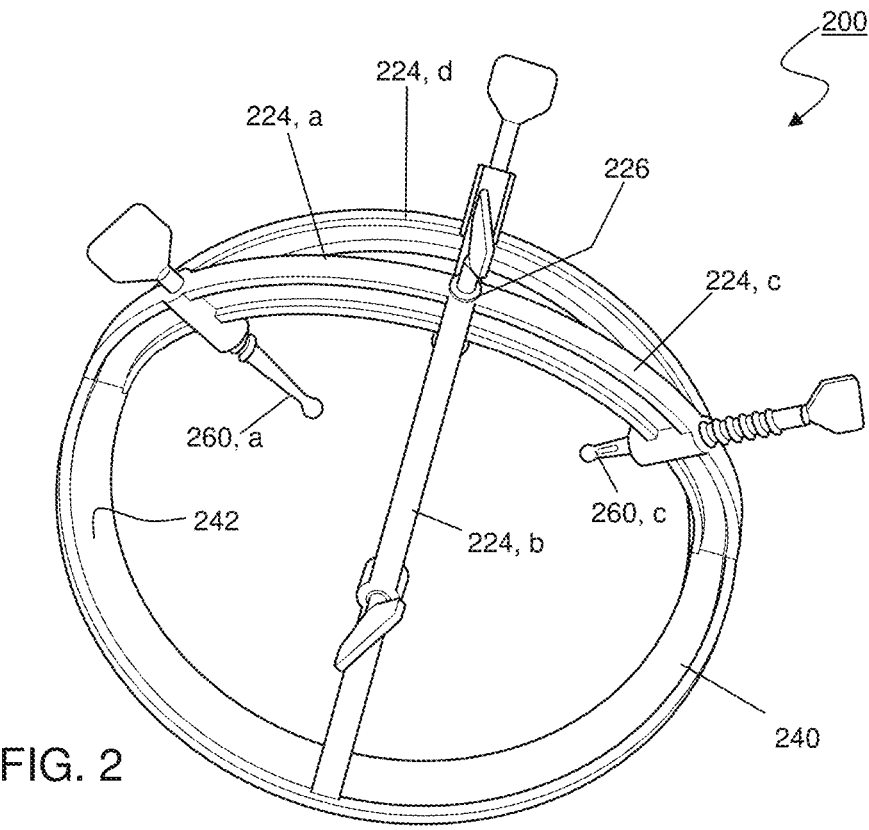
Figure 3:
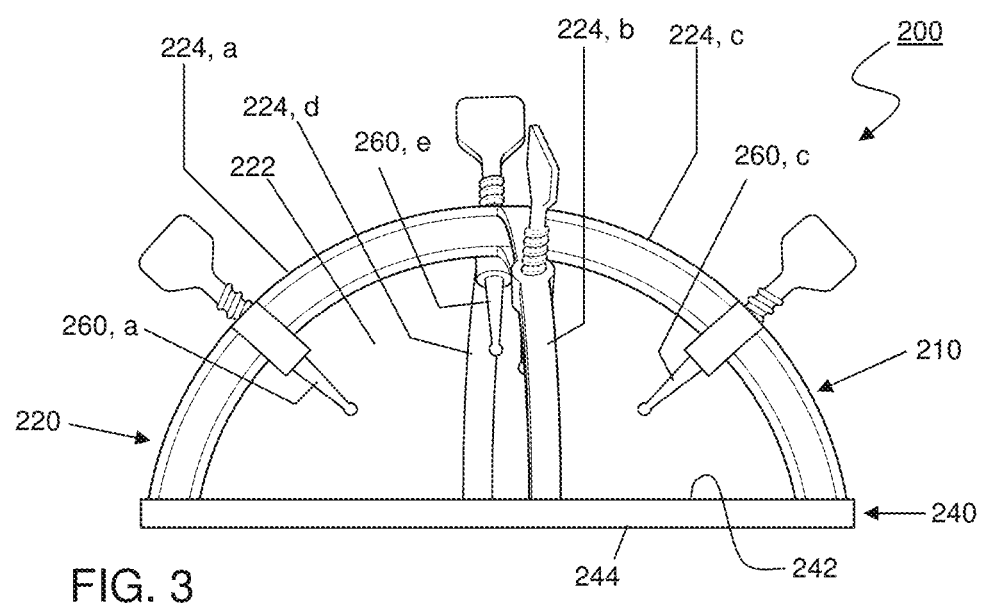
Figure 5:
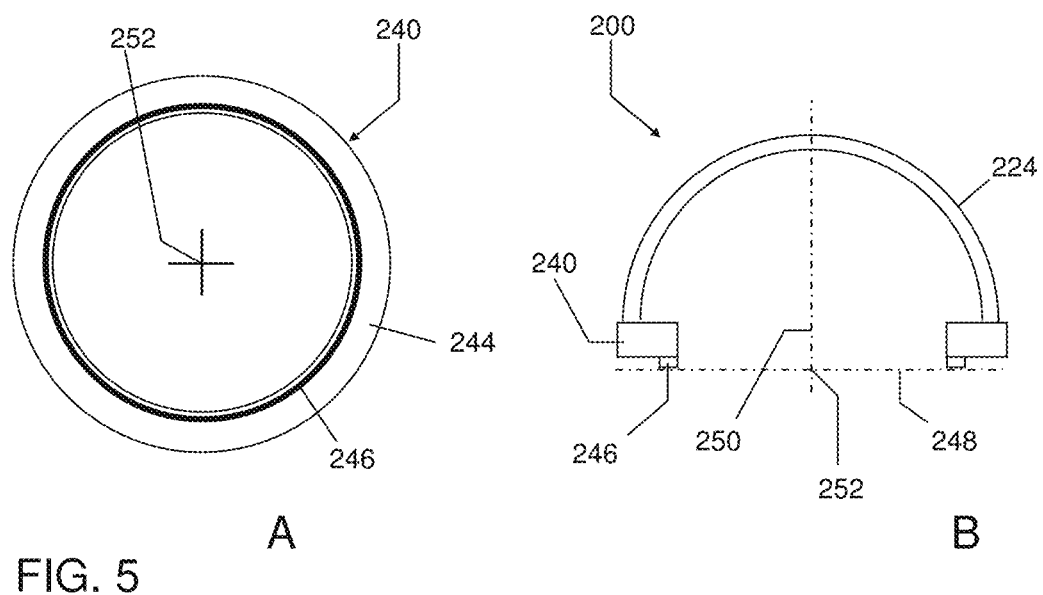

The superior positioning cap (SPC) (200) is configured placement on a top of a head (16) of the subject, namely a skull part of the head (16). An exemplary superior positioning cap (200) is shown in FIGS. 2, 3 and 5. The pose of the superior positioning cap (200) is adjustable and fixable relative to a positional reference of the subject. The positional reference of the subject may be the mid-commissural point (MCP) (26) in the brain (18) of the subject. The superior positioning cap (200) is configured for setting a pose of an intermediate head clamp (300) on a subject relative to a positional reference of the subject. When the superior positioning cap (200) and the intermediate head clamp (300) co-operate, the pose of the intermediate head clamp (300) can be set.

The superior positioning cap (200) comprises a supporting frame (210). The supporting frame comprises a supporting frame superior part (220) forming a domed receiving space (222) for the part of the head of the subject, and a supporting frame inferior base part (240) attached to the base of the dome. The dome receiving space (222) may be a spherical dome. The spherical dome may have a sphere diameter of 22-26 cm, preferably 24 cm. The supporting frame is rigid.

The supporting frame superior part (220) may comprise a body having 4 or more curved support members (224, a, b, c, d), joined together at one end to each other at a common region (226) at the top of the supporting frame superior part (220), and at the other end to the supporting frame inferior base (240). Spaces between the curved support members are preferably open. The supporting frame inferior base (240) is preferably annular (circular) or contains an annular (circular) path. A curved support member (224, a, b, c, d) may be a circular arc, the centre of the arc coinciding with an SPC axis of reference (250) of the superior positioning cap (200). The SPC axis of reference (250) extends in a superior-inferior direction. The SPC axis of reference (250) is an axis that is co-axial with the axis of rotation (350) of the intermediate head clamp (300) and with the axis of reference (450) of the inferior positioning support (400) when the SPC (200), IHC (300) and IPS (400) co-operate. The intermediate head clamp (300) rotates around this axis.

Figure 4:
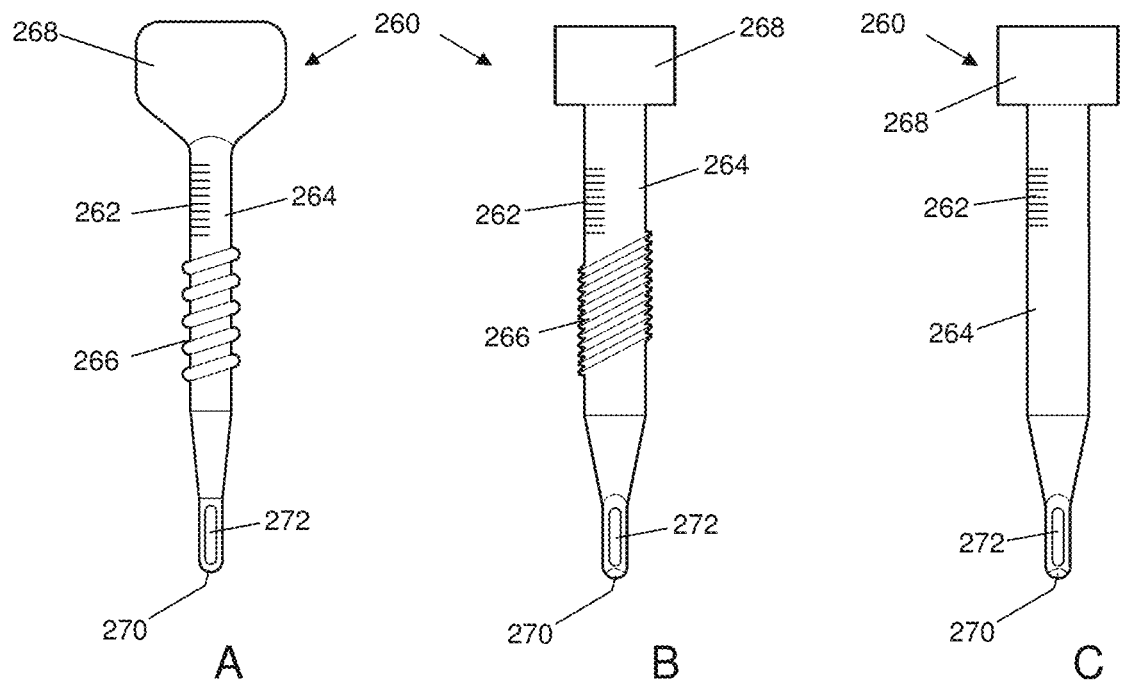

The superior positioning cap (200) further comprises a plurality of adjustable protrusions (260, a, b, c, d, e). Each adjustable protrusion is configured for controlled advancement into the domed receiving space or withdrawal therefrom. Each adjustable protrusion is configured for contacting a part of the head of the subject. Adjustment of one or more of the plurality of adjustable protrusions adjusts and stabilises the pose of the supporting frame relative to the head of the subject, and hence relative to the MCP (26). The plurality of adjustable protrusions may be each slidably and/or rotatably attached to the supporting frame superior part (220), more preferably to the curved support member (224, a, b, c, d). Exemplary adjustable protrusions are shown in detail in FIGS. 4A to 4C.

At least one, preferably all of the plurality of adjustable protrusions may comprise a moveable shaft (264), configured for advancement into the domed receiving space or withdrawal therefrom. The moveable shaft (264) may be at least partially threaded (266) (e.g. FIGS. 4A and 4B). The moveable shaft (264) may be non-threaded (e.g. FIG. 4C); the distance may be lockable with a side screw or clamp. The moveable shaft (264) may be provided with a surface-marked measurement gauge (262); the measurement gauge is for reading-out a distance setting of the moveable shaft. The distance setting may be a distance from the head exterior of the subject to the supporting frame. The moveable shaft may have a central (longitudinal) axis having a direction crossing the SPC axis of reference (250) of the superior positioning cap (200). The direction may cross the MCP (26). The number of adjustable protrusions may be 4, 5, 7, 9, 10 or more. Two or more adjustable protrusions may be spaced along the curved support member, each separated by an angle of 40 to 50 deg.

The adjustable protrusion may be provided with a head (268) to allow adjustment of the moveable shaft. The adjustable protrusion may be motorised to allow automated setting of the moveable shaft. A tip (270) of the shaft (264) may be rounded or pointed. A cavity (272) may be provided in the shaft (262) connecting a side of the shaft with an opening in the tip (270). The cavity is dimensioned to receive a measurement probe for optical measurement of the pose of the superior positioning cap (200) by one or more external cameras in a position measurement system (e.g. optical localiser).

At least one, preferably all of the adjustable protrusions (260, a, b, c, d, e) may be disposed with a surface-marked measurement gauge or scale; the measurement gauge is for reading-out a depth setting of each adjustable protrusion. It enables the depth of each adjustable protrusion to be manually set with respect to the supporting frame superior part (220). The depth settings may be set based on a 3D medical image.

The base part (240) has a superior side (242) an inferior side (244). The inferior side (244) may be planar. The superior positioning cap (200), in particular the inferior side (244) is disposed with a movement guide (246) configured to co-operate with a complementary movement guide (346) of the intermediate head clamp (300). FIGS. 5A and 5B show an exemplary movement guide (246). The movement guide (246) limits relative movement of the parts to a guide path. The guide path is a circular path. Herein, a circular path includes a complete circle or a circular arc. The circular path is planar. The movement guide (246) describes a circular path of rotation. The movement guide (246) has an axis of reference (250), which is an axis passing through a centre (252) of the circular path (246) and is perpendicular to a plane (248) of the circular path. This is also known as the SPC axis of reference (250).

An edge of the base part (240) may be disposed with a surface-marked measurement gauge or scale; the measurement gauge is for reading-out an angle setting of the intermediate head clamp (300) with respect to the superior positioning cap (200). The edge is an outside edge. The marking may be in angular degrees (e.g. 0 to 359 deg). 0 degrees may correspond to the nasion.

When both the movement guide (246) of the superior positioning cap (200) and of the intermediate head clamp (300) co-operate, movement of the intermediate head clamp (300) is limited to rotation about the superior positioning cap (200), in particular around the respective axes of rotation (350) which coincides with the IHC axis of reference (350). The movement guide (246) may comprise a continuous or discontinuous protrusion or recess or edge, that couples with a complementary continuous or discontinuous recess or surface protrusion of the complementary movement guide of the intermediate head clamp (300).

The superior positioning cap may be made from any suitable material that provides the requisite strength and rigidity. The material may be non-ferrous to allow use with a medical imager. The material should also comply with the requirements of good surgical practice, e.g. be washable. It may be a sterilisable material also. Examples of suitable materials include polymers (e.g. polyethylene, polypropylene, polycarbonate, polyurethane), metals or alloys (e.g. aluminium, titanium), ceramic (silicon based), composites.

An exemplary inferior positioning support (IPS) (400) is illustrated in FIGS. 6A to 8. The inferior positioning support (IPS) (400) is configured for placement around the head, in a region coinciding with the forehead. The pose of the inferior positioning support (400) is adjustable and fixable relative to a positional reference of the subject. The positional reference of the subject may be the mid commissural point (MCP) (26) in the brain of the subject. The inferior positioning support (400) is configured for setting a pose of an intermediate head clamp (300) on a subject relative to the positional reference of the subject. When the inferior positioning support (400) and the intermediate head clamp (300) co-operate, the pose of the intermediate head clamp (300) can be set. When both the inferior positioning support (400) and the superior positioning cap (200) flank and co-operate with intermediate head clamp (300), the pose of the intermediate head clamp (300) is highly accurately determined.

The inferior positioning support (400) comprises a main body having superior side (412) and opposing inferior side (414). The superior side (412) and optionally the inferior side (414) may be planar. The inferior positioning support (400) further comprises a holding space (422) at least partially surrounded by the main body dimensioned to receive the head of the subject. The holding space (422) may have a span of 22-26 cm, preferably 24 cm. The holding space preferably has a circular profile. A side opening (424) in the main body (410) may be provided for connecting the holding space to an exterior edge of the main body in order to allow removal of the inferior positioning support (400) from the subject by a lateral movement through the side opening (424). The side opening (424) may be disposed on a posterior side of the main body (410). The side opening (424) may span a geometric segment of the circular path of the movement guide (446) that is between 55-180 deg, preferably 65 deg.

The main body has a height, that is a dimension parallel to the axis of reference (450) of the inferior positioning support (400); the height may be 1-3 cm.

The superior side (412) may be disposed with a movement guide (446) configured to co-operate with a complementary movement guide (346') of the intermediate head clamp (300). An exemplary movement guide (446) is shown in FIGS. 7A and 7B and in FIG. 8. The movement guide (446) limits relative movement of the parts along to a guide path. The guide path is a circular path. Herein, a circular path includes a complete circle or a circular arc. The circular path is planar. The movement guide (446) describes a circular path of rotation. The movement guide has an axis of reference (450), which is an axis passing through the centre (452) of the circular path and is perpendicular to a plane (448) of the circular path. This is also known as an IPS axis of reference (450).

An edge of the main body (410) may be disposed with a surface-marked measurement gauge or scale; the measurement gauge is for reading-out an angle setting of the intermediate head clamp (300) with respect to the inferior positioning support (400). The edge is an outside edge. The marking may be in angular degrees (e.g. 0 to 359 deg). 0 degrees may correspond to the nasion.

When both the movement guides (446, 346) of the inferior positioning support (400) and of the intermediate head clamp (300) co-operate, movement of the intermediate head clamp (300) is limited to rotation about the interior positioning support (400), in particular around the IPS axis of reference (450). The movement guide may comprise a continuous or discontinuous protrusion or recess or edge, that couples with a complementary continuous or discontinuous recess or protrusion or surface of the complementary movement guide of the intermediate head clamp (300).

Figure 6A:
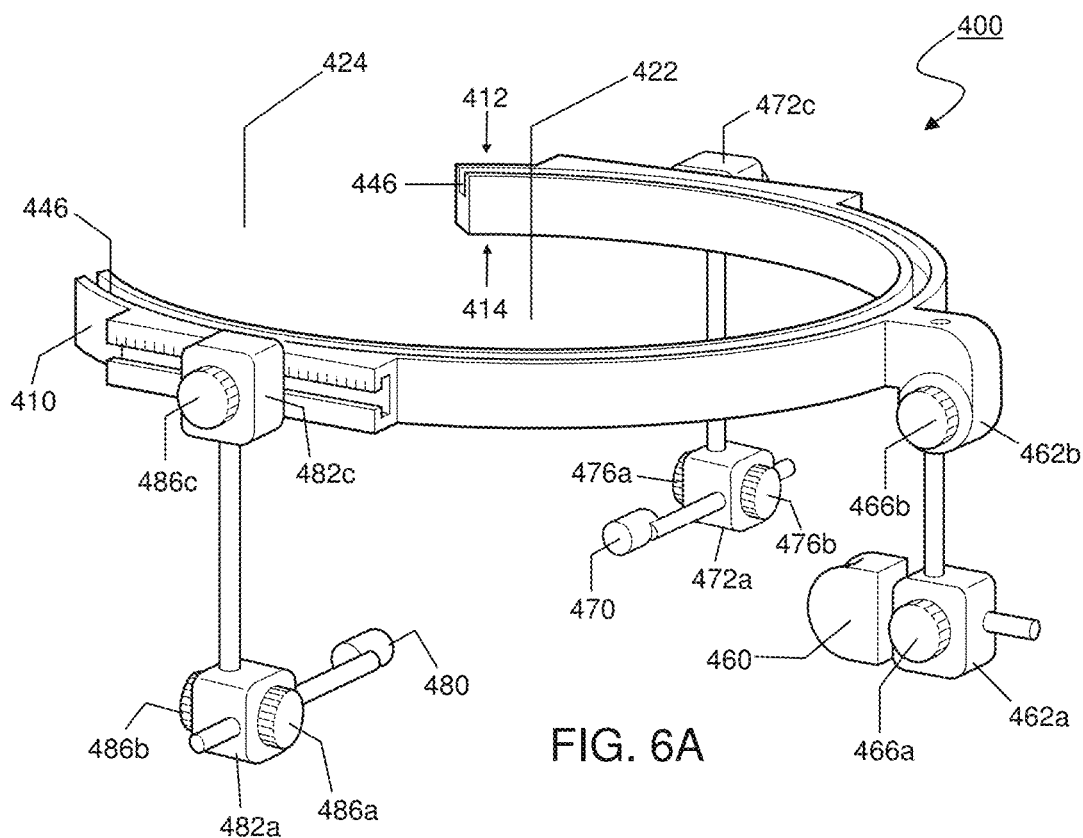
Figure 6B:
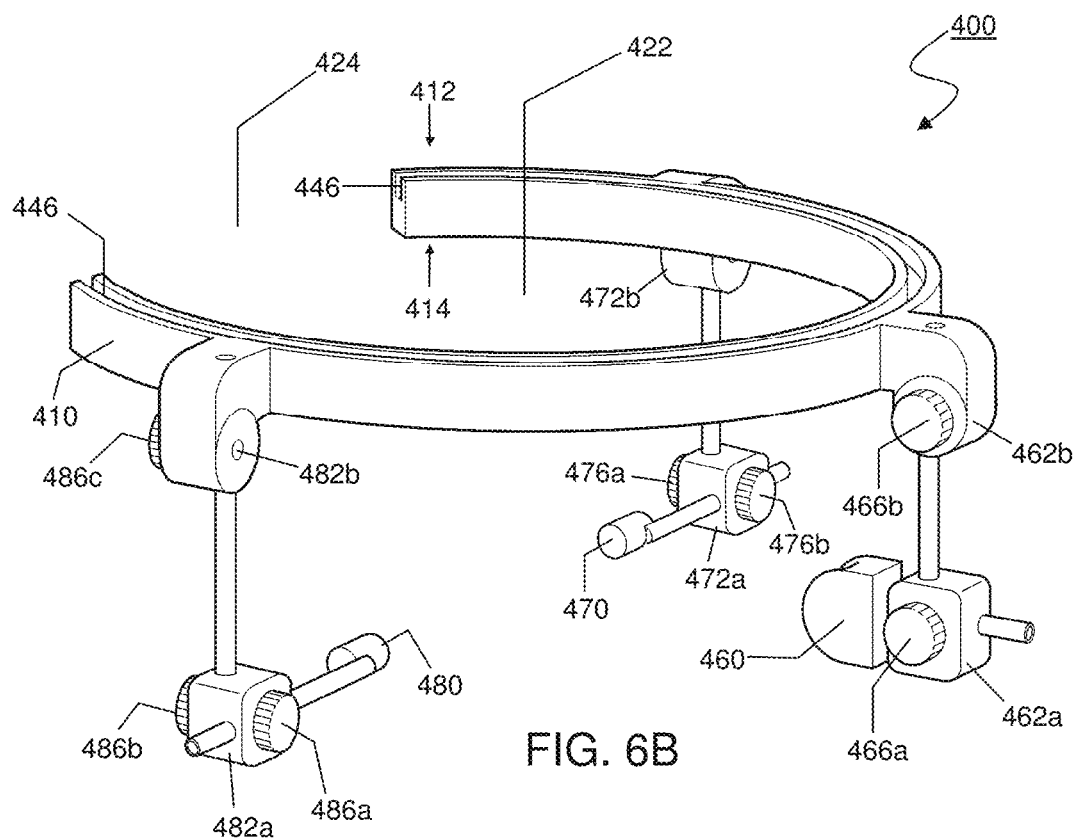
Figure 7:
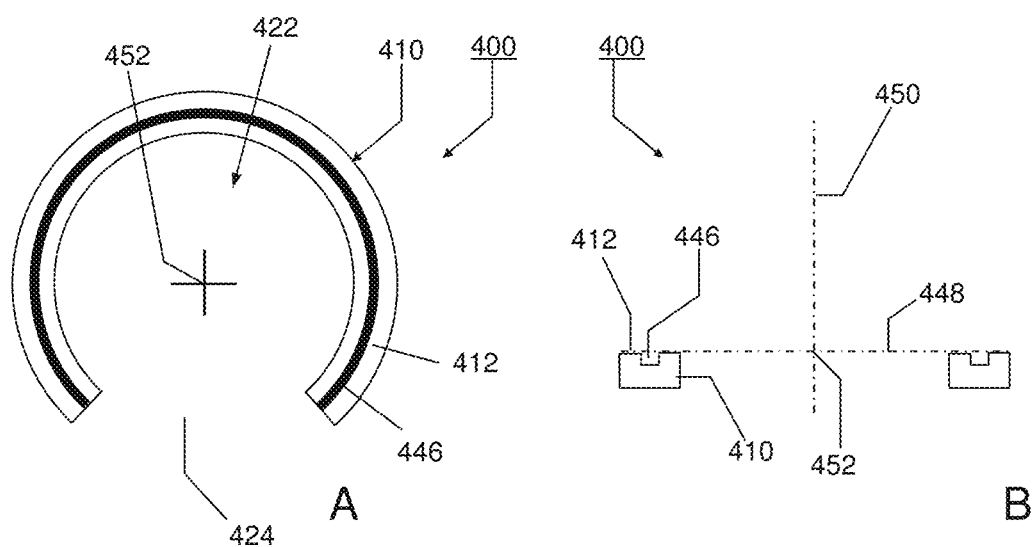

The inferior positioning support (400) further comprises a plurality of locating bodies (460, 470, 480); a locating body (460, 470, 480) locates in and engages with a bodily recess of the subject's head (e.g. in the nasion, left ear intratragic notch and right ear intratragic notch). Exemplary locating bodies are shown in FIGS. 6A and 6B. Each locating body (460, 470, 480) is attached in adjustable and fixable in relation to main body (410). According to one example, there may be at least 3 locating bodies, one for each of the nasion (460) (disposed on an anterior side of the main body), left ear intratragic notch (470) and right ear intratragic notch (480) (disposed on lateral sides of the main body). The nasion (20) is indicated in FIG. 1. The presence of three locating bodies supports the main body (410), and allows adjustment of the pose of the main body (410) relative to the head, in particular relative to the MCP (26). Preferably the pose of the main body (410) is adjusted such that the MCP (26) coincides with the SPC axis of reference (250). Preferably the pose of the main body is adjusted such that the plane (448) of the circular path of rotation is parallel to the AC-PC line (30).

A locating body (460, 470, 480) may be attached to the main body by a one or more joints (e.g. prismatic and/or revolute) (462a, b; 472a, b, c; 482a, b, c) wherein the position of each joint is adjustable and lockable, for instance, using a thumb-screw (466a, b; 476a, b; 486a, b, c). In FIGS. 6A and 6B, revolute and prismatic joints (462a, b; 472a, b, c; 482a, b, c) connect each locating body (460, 470, 480) to the main body (410). In FIG. 6A the joint connecting to the main body (410) is prismatic (472c, 482c) for the left ear intratragic notch (470) and right ear intratragic notch (480); this prismatic joint also has a scale. In FIG. 6B the joint connecting to the main body (410) is revolute (462b, 472b, 482b).

The locating body (460, 470, 480) may be attached to the main body by a kinematic chain. Each joint may be manually setable. A surface-marked measurement gauge may be associated with a joint; the measurement gauge is for reading-out a distance or angle setting of the joint. One or more joints may be motorised to allow automatic setting of the joint.

Figure 8:
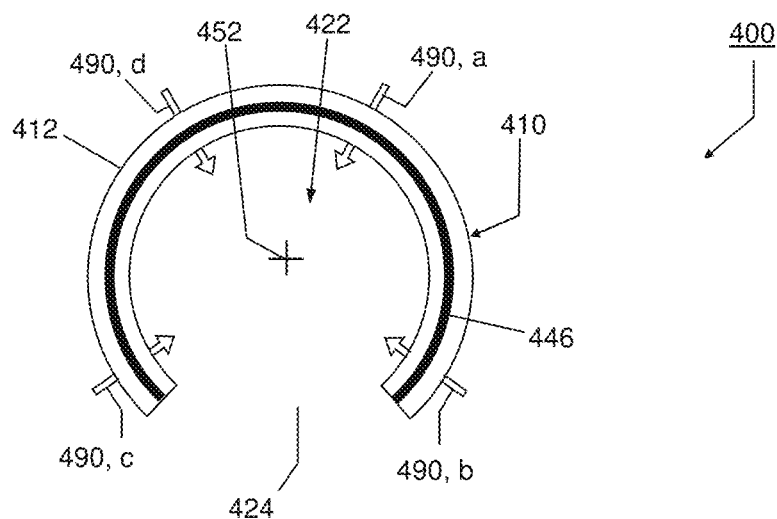

The inferior positioning support (400) may further comprise a plurality of clamps (490, a, b, c, d). Exemplary clamps (490, a, b, c, d) are illustrated in FIG. 8. Each clamp is configured for advancement into the holding space (422) or withdrawal therefrom. Each clamp is configured for contacting the part of the head of the subject. Deployment of one or more of the plurality of clamps fixes or stabilises the pose of the main body (410) relative to the head of the subject, and hence relative to the MCP (26). The clamps (490, a, b, c) may be deployed once the pose of the inferior positioning support (400) has been set with respect to the locating body. The number of clamps may be 4. The clamps may be positioned around the main body (410) at 30° (e.g. 490, a), 135° (e.g. 490, b), 225° (e.g. 490, c), 330° (e.g. 490, d), where 0° is at a locating body (460) above the nasion (20).

The plurality of clamps (490, a, b, c) may be each slidably and/or rotatably attached to the main body (410). At least one, preferably all of the plurality of clamps may comprise a moveable shaft, configured for advancement into the holding space or withdrawal therefrom. The moveable shaft may be at least partially threaded. The moveable shaft may have a central (longitudinal) axis having a direction crossing the IPS axis of reference (450). The direction may cross the MCP (26). The clamp may be provided with a head to allow adjustment of the moveable shaft. The clamp may be motorised to allow automated setting of the moveable shaft.

The inferior positioning support may be made from any suitable material that provides the requisite strength and rigidity. The material may be non-ferrous to allow use with a medical imager. The material should also comply with the requirements of good surgical practice, e.g. be washable. It may be a sterilizable material also. Examples of suitable materials include polymers (e.g. polyethylene, polypropylene, polycarbonate, polyurethane), metals or alloys (e.g. aluminium, titanium), ceramic (silicon based), composites.

Exemplary intermediate head clamps (IHC) (300) are shown in FIGS. 9 to 18. The intermediate head clamp (IHC) (300) is configured for placement around the head, in a region parallel to and superior to the AC-PC line. The intermediate head clamp (300) may co-operate with both the inferior positioning support (400) (e.g. FIG. 19) and with the superior positioning cap (200) (e.g. FIG. 20), which co-operation sets the pose of the intermediate head clamp (300). Clamps disposed around the intermediate head clamp (300) lock the intermediate head clamp (300) to the head of the subject for a duration of the intervention, and also lock the pose of the intermediate head clamp (300) with respect to the head, and relative to the positional reference of the subject. The positional reference of the subject may be the mid commissural point (MCP) (26) in the brain of the subject. The pose of the intermediate head clamp (300) is hence highly accurately determined by both superior and inferior positioning guides; once the clamps have been deployed, the inferior positioning support (400) and the superior positioning cap (200) can be removed.

The intermediate head clamp (300) comprises a main body (310) having superior side (312) and opposing inferior side (314). The superior side and opposing inferior side may be planar; the planes may be parallel. The intermediate head clamp (300) further comprises a holding space (322) at least partially surrounded by the main body (310) dimensioned to receive the head of the subject. The holding space (322) may have a span of 22-26 cm, preferably 24 cm. The holding space (322) may be essentially disc-shaped. The main body has a height, that is a dimension parallel to the axis of rotation of the intermediate head clamp (300); the height may be 1-3 cm. The holding space (322) is preferably configured to receive a circular structure. A side opening (324) in the main body may be provided for connecting the holding space to an exterior edge of the main body in order to allow un-restricted access by user (e.g. neurosurgeon) to the target. The side opening may be disposed on an anterior side of the main body. The side opening (324) may span a geometric segment of the circular path of the movement guide (346, 346') that is between 60-180 deg.

An edge (316) of the main body (310) may be disposed with a surface-marked measurement gauge or scale; the measurement gauge is for reading-out an angle setting of the intermediate head clamp (300) with respect to either or both of the superior positioning cap (200) and the inferior positioning support (400). The edge (316) may be the outside edge.

The intermediate head clamp (300) in particular the superior side (312) may be disposed with a movement guide (346) configured to co-operate with a complementary movement guide (246) of the superior positioning cap (200). A view of the superior side (312) of the movement guide is shown in FIGS. 10A and 10B. The movement guide (346) limits relative movement of the parts along to a guide path. The movement guide (346) describes a circular path of rotation. The circular path is planar. The movement guide has an axis of rotation (350), which is an axis passing through the centre (352) of the circular path and is perpendicular to a plane (348) of the circular path. This is also known as an axis of rotation (350) of the intermediate head clamp (300). The movement guide may comprise a continuous or discontinuous protrusion or recess or edge, that couples with a complementary continuous or discontinuous recess or protrusion or surface of the complementary movement guide (246) of the superior positioning cap (200).

The intermediate head clamp (300) in particular the inferior side (314) may be disposed with a movement guide (346') configured to co-operate with a complementary movement guide of the inferior head clamp (200). A view of the inferior side (314) of the movement guide is shown in FIGS. 11A and 11B. The movement guide (346') limits relative movement of the parts along to a guide path. The guide path is a circular path. Herein, a circular path includes a complete circle or a circular arc. The circular path is planar. The movement guide (346') describes a circular path of rotation. The movement guide (346') has an axis of rotation (350'), which is an axis passing through the centre (352') of the circular path and is perpendicular to a plane (348') of the circular path. This inferior side axis of rotation (350') coincides or is co-axial with the superior side axis of rotation (350), and hence with the axis of rotation (350) of the intermediate head clamp (300). The movement guide (346') may comprise a continuous or discontinuous protrusion or recess or edge, that couples with a complementary continuous or discontinuous recess or protrusion or surface of the complementary movement guide of the inferior positioning support (400).

When the movement guides of the inferior positioning support (400) (446) and of the intermediate head clamp (300) (346, 346') and superior positioning cap (200) (246) co-operate, movement of the intermediate head clamp (300) is limited to rotation about the interior positioning support (400) and superior positioning cap (200), in particular around the axis of rotation (350).

Figure 9:
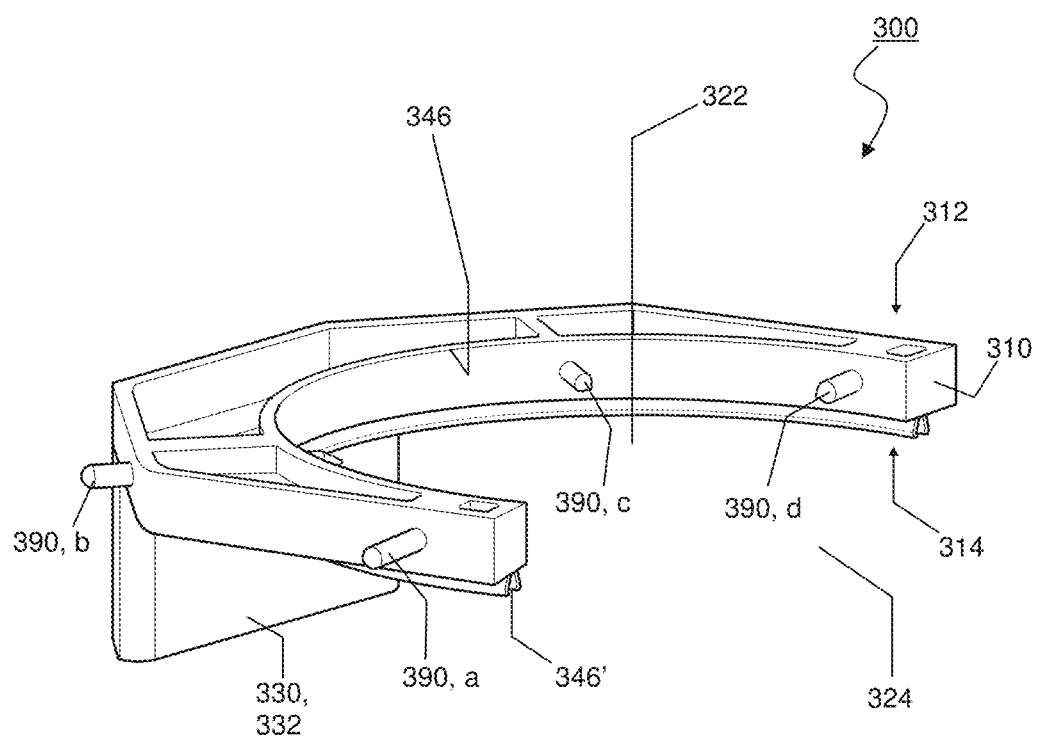
Figure 10:
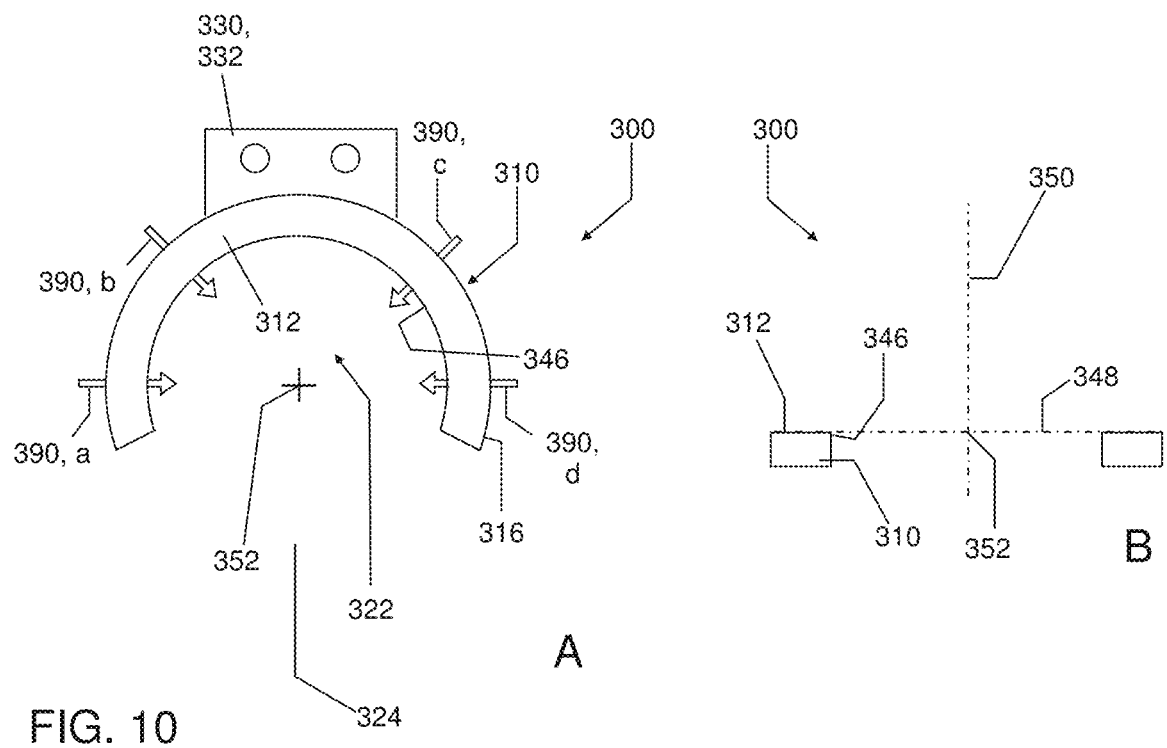
Figure 11:
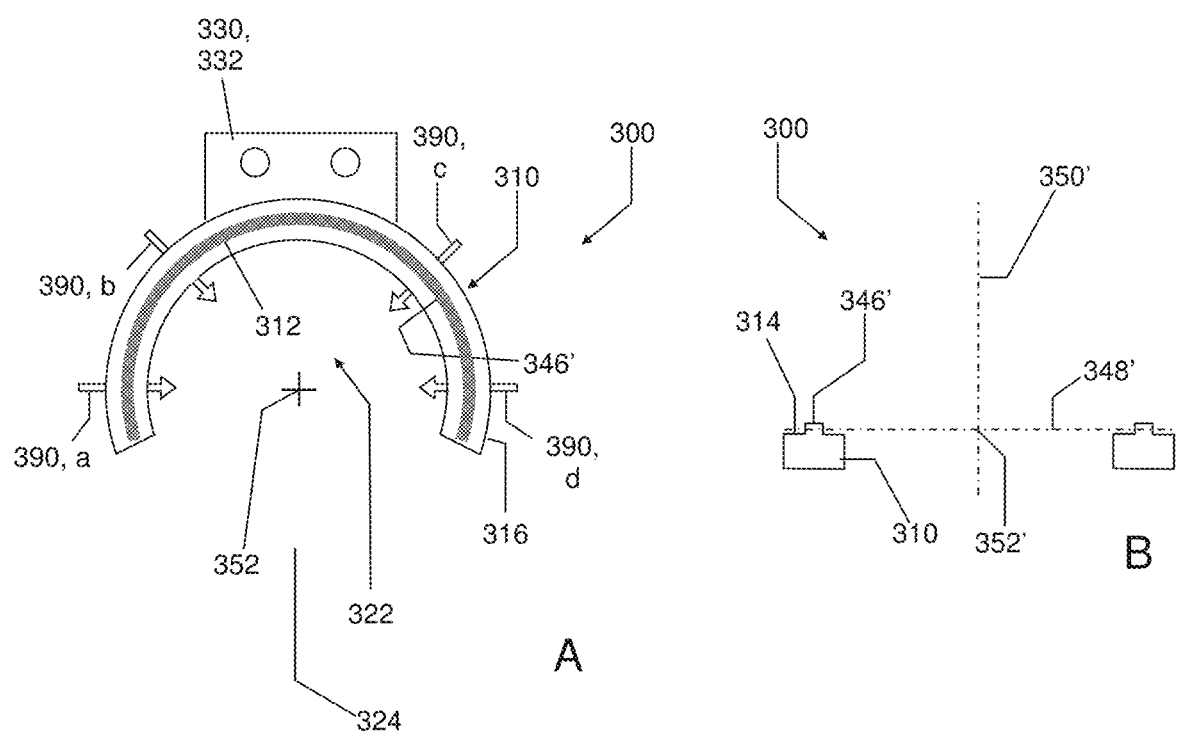

The intermediate head clamp (300) may further comprise a plurality of clamps (390, a-d). Each clamp (390, a-d) is configured for advancement into the holding space or withdrawal therefrom. Exemplary clamps are illustrated in FIGS. 9 to 11. Each clamp (390, a-d) is configured for contacting the part of the head of the subject. Deployment of one or more of the plurality of clamp (390, a-d) stabilises or fixes the pose of the main body (310) relative to the head of the subject, and hence relative to the MCP (26). The clamp (390, a-d) may be deployed once the pose of the intermediate head clamp (300) has been set with respect to the inferior positioning support (400) and the superior positioning cap (200). The number of clamps may be 4. The clamps may be positioned at 90°, 135°; 225° & 270°, where 0° is at a centre of the side opening (324).

The plurality of clamps (390, a-d) may be each slidably and/or rotatably attached to the main body (310). At least one, preferably all of the plurality of the clamps (390, a-d) may comprise a moveable shaft, configured for advancement into the holding space (322) or withdrawal therefrom. The moveable shaft may be at least partially threaded. The moveable shaft may have a central (longitudinal) axis having a direction crossing the axis of rotation (350) of the intermediate head clamp (300). The direction may cross the MCP (26). The clamp may be provided with a head to allow adjustment of the moveable shaft. The moveable shaft may be motorised to allow automated setting of the moveable shaft.

Figure 43:
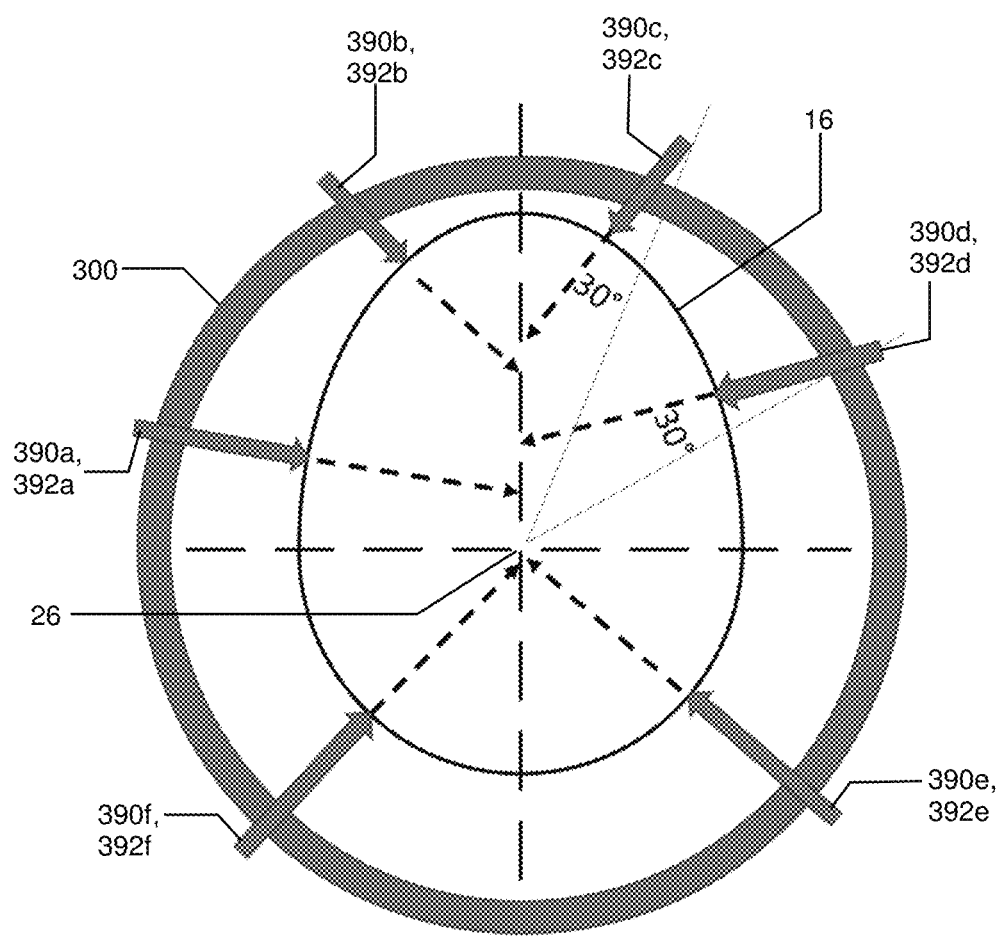
FIG. 43 is a schematic view of an intermediate head clamp, disposed with steerable moveable shafts.

To optimally secure the intermediate head clamp (300), a direction (i.e. rotation) of the moveable shaft (392) with respect to the main body (310) of the intermediate head clamp (300) may be adjustable; it allows the intermediate head clamp (300) to be aligned perpendicular (in at least one plane) to an angled surface of the head of the subject. In other words, the moveable shaft (392) may be steerable. FIG. 43 illustrates the effect of moveable shafts (392a to f). When the direction of each moveable shaft (392a to f) is fixed and points towards the MCP (26), the majority of moveable shafts (392a to d) contact the head (16) of the subject at an angle, thereby not securing optimally the intermediate head clamp (300). FIG. 43 illustrates each steerable moveable shaft (392) can be directed to contact the head (16) of the subject perpendicularly.

Figure 29:
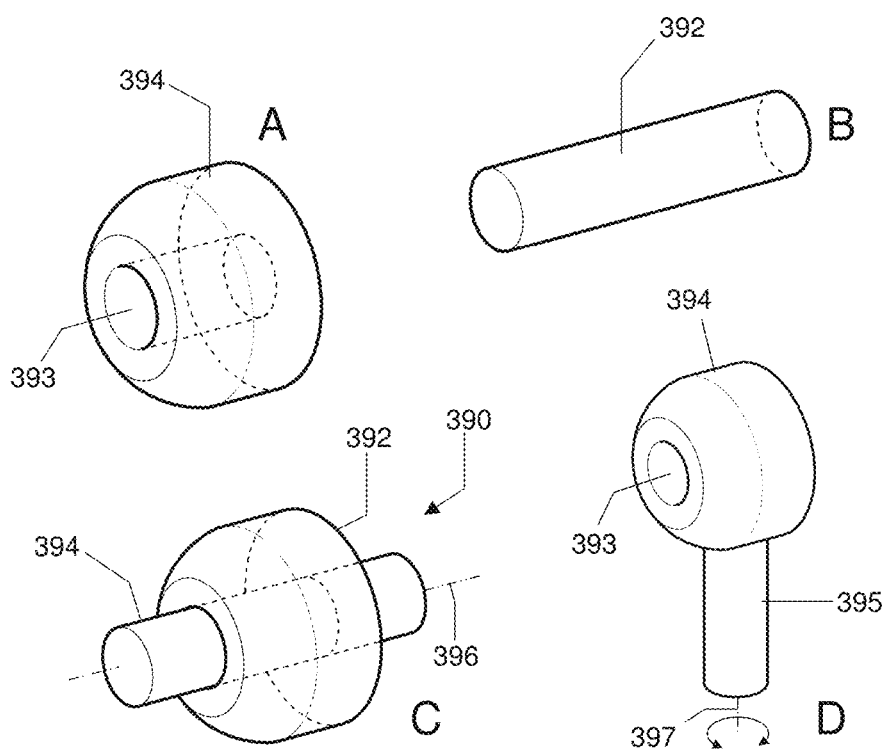
Figure 30:
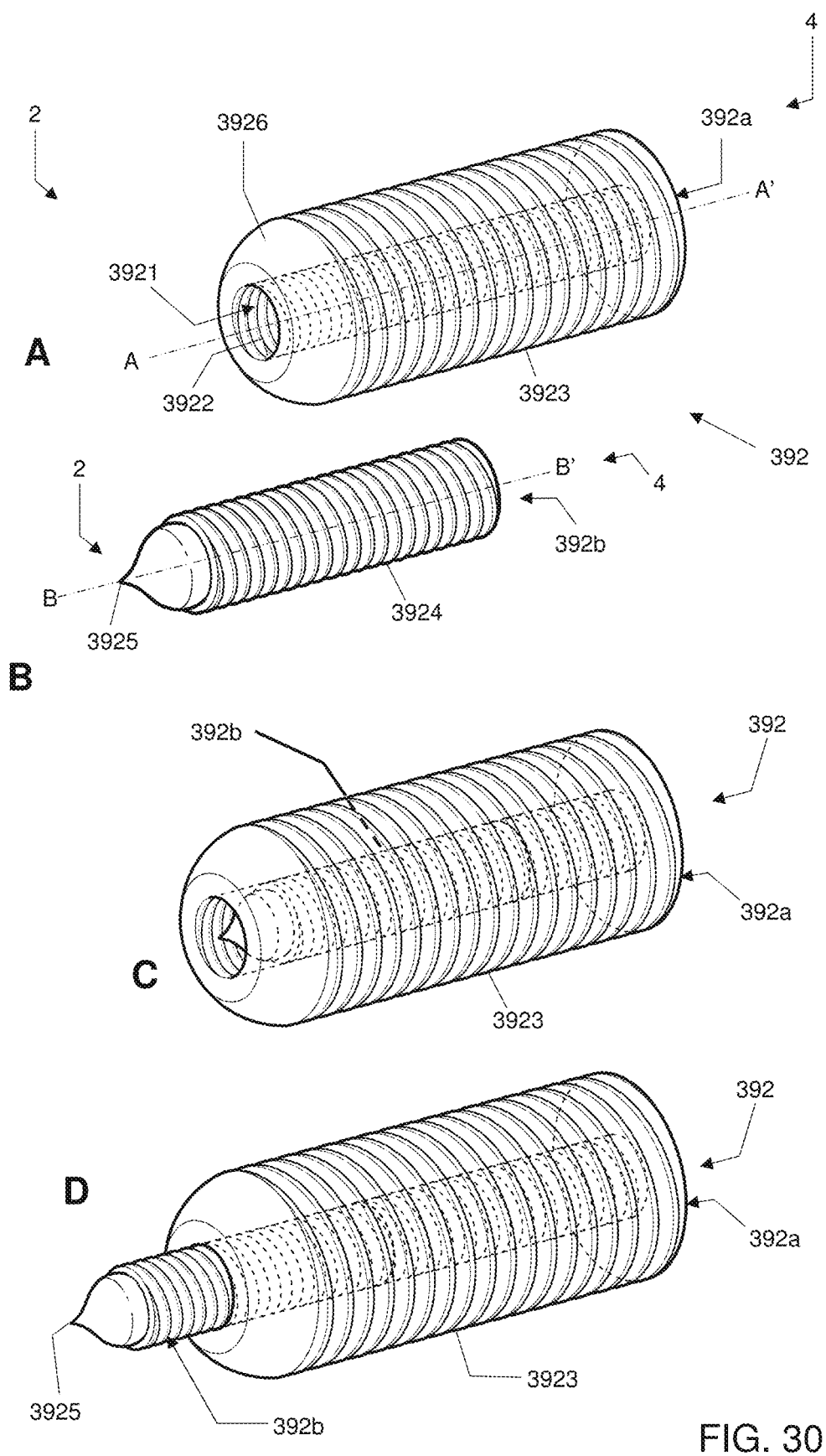
Figure 31:
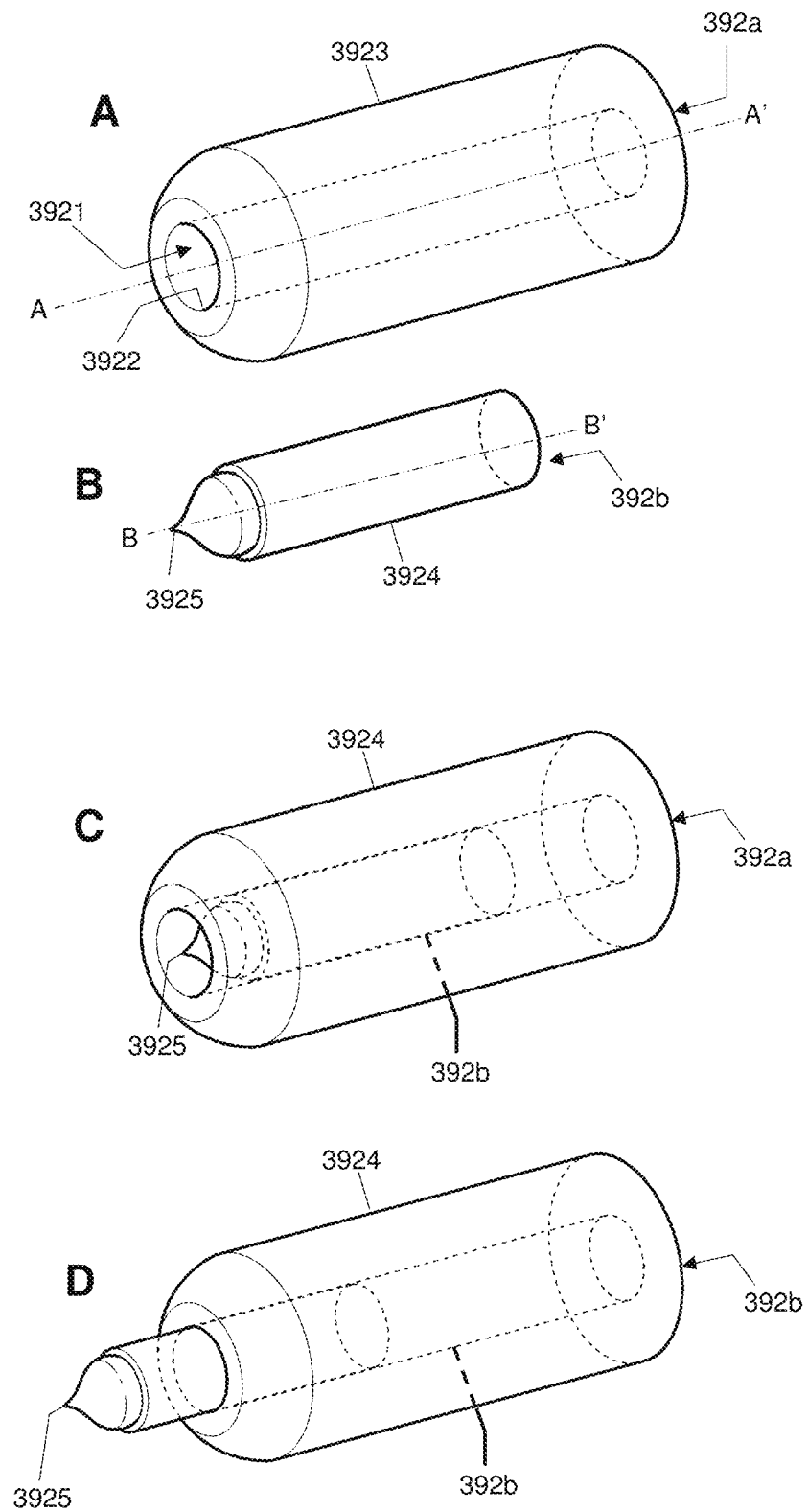
Figure 32:
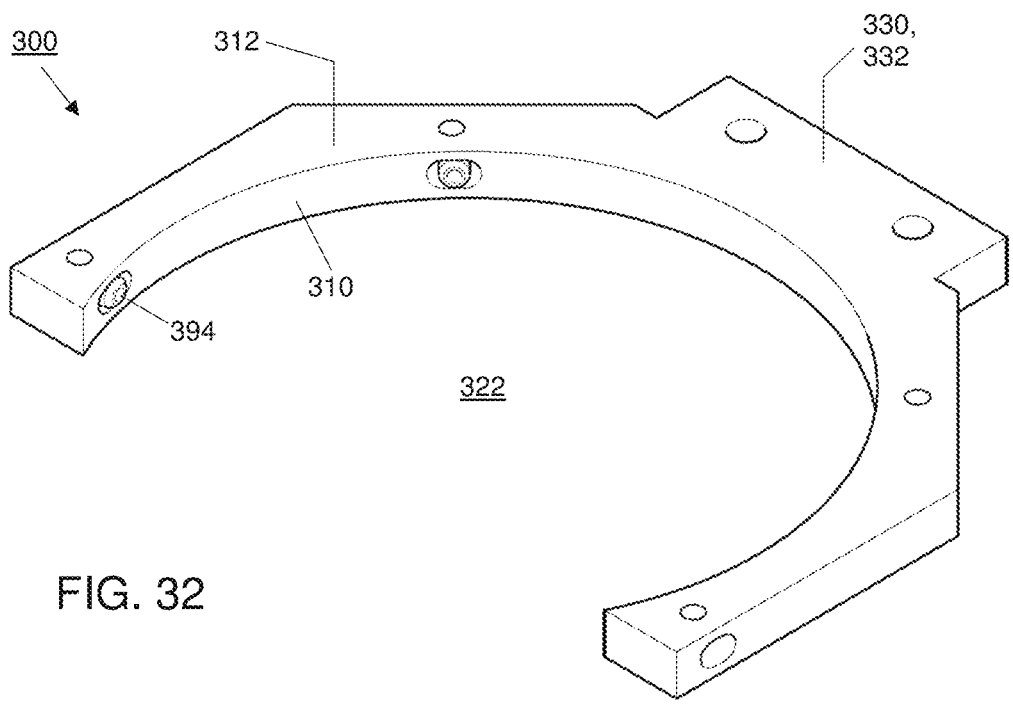
Figure 33:
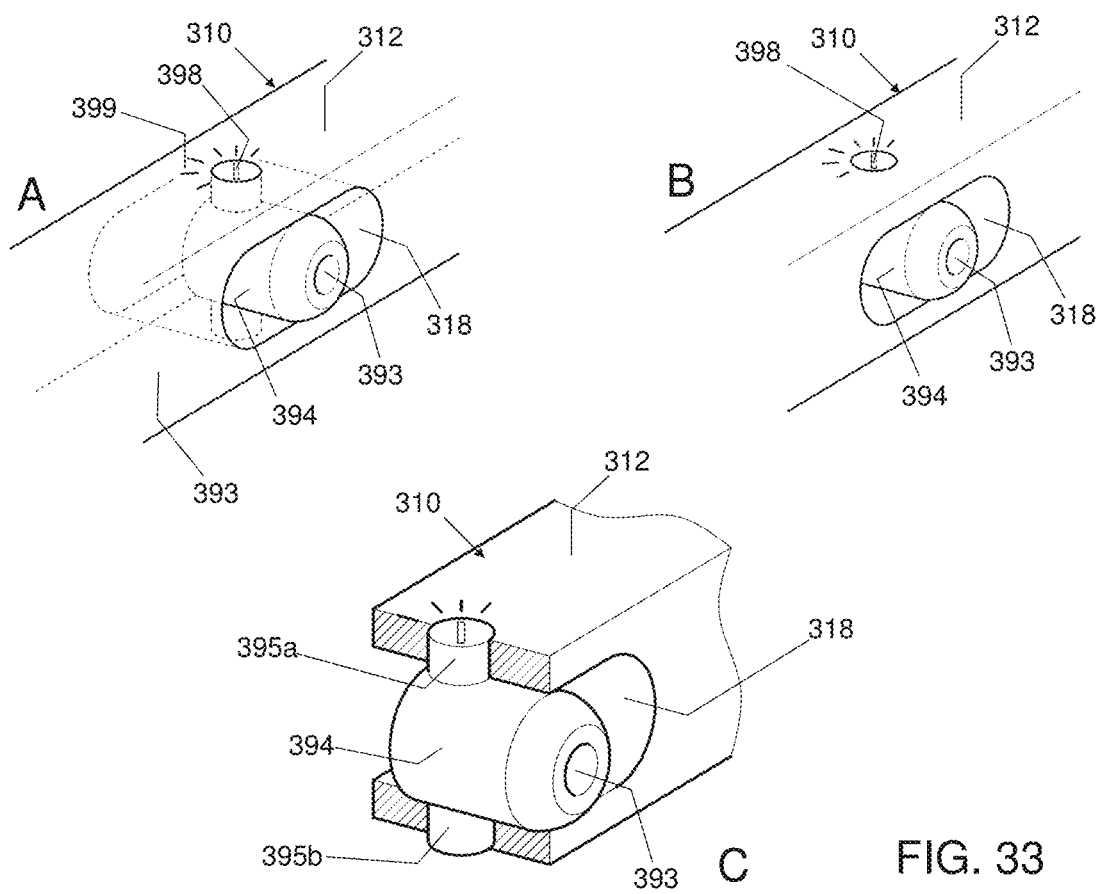

A shaft-receiving body (394) may be provided disposed with a passageway (393) for receiving and supporting the moveable shaft (392) of the clamp (390). An example of a steerable moveable shaft (392) is shown in FIGS. 29A and C, and of a steerable shaft-receiving body (394) is shown in FIGS. 29A, C and D. The shaft-receiving body (394) is rotatably attached to the intermediate head clamp (300) main body (310). The attachment allows rotation of the shaft-receiving body (394) around 1, 2 or 3, preferably 1 axis (e.g. 397) of rotation relative to the main body (310). This allows the shaft-receiving body (394) to swivel relative to the intermediate head clamp (300) main body (310). The direction of the (one) axis (397) around which the shaft-receiving body (394) rotates may be perpendicular to a central axis (396) of the moveable shaft (392) of the clamp (390).

The shaft-receiving body (394) may be attached to the intermediate head clamp (300) main body (310) via one or more links (395) (e.g. FIGS. 29D, 33A to C). The link (395, 395a, 395b) is rigid. The link (395) may be attached at one end in fixed (non-adjustable) relation to the shaft-receiving body (394) and at the other end may be revolutely attached to the intermediate head clamp (300) main body (310). Alternatively, the link (395) may be attached at one end in fixed (non-adjustable) relation to the intermediate head clamp (300) main body (310) and at the other end may be revolutely attached to the shaft-receiving body (394). The may be one or two links. The link (395a, 395b) may include a coupling (398) for a tool such as a slotted or Philipps screwdriver to adjust the direction of the shaft-receiving body (394) (e.g. FIGS. 33A to C). Access to the coupling (398) may be via an opening in the intermediate head clamp (300) main body (310). The main body (310) may be disposed with a surface-marked measurement gauge or scale (399) so the direction (angle) of the shaft-receiving body (394) can be read off.

In one example, the shaft-receiving body (394) is disposed within the intermediate head clamp (300) main body (310). This might be realised by the presence of a slot (318) running through the main body (310) as shown in FIGS. 32, and 33A to C. The slot (318) is disposed in the main body (310) between the superior (312) and inferior (314) sides In another example, the shaft-receiving body (394) is disposed on a surface of the intermediate head clamp (300) main body (310). The shaft-receiving body (394) may be disposed on the superior side (312), inferior side (314), or shaft-receiving bodies (394) may be disposed both sides (312, 314).

A locking mechanism may be provided to fix the direction of the shaft-receiving body (394). The locking mechanism may have an open state wherein the direction of the shaft-receiving body (394) can be adjusted, and a closed state wherein the direction of the shaft-receiving body (394) is fixed. The locking mechanism may comprise a friction clamp (e.g. threaded member).

The moveable shaft (392) of the clamp (390) may be telescopic, comprising an outer moveable shaft (392a) and an inner moveable shaft (392b). Examples are shown in FIGS. 30A-D and 31A-D. The inner moveable shaft (392b) is disposed within a passageway (3922) of the outer moveable shaft (392a). The outer moveable shaft (392a) may be moveable in an axial direction (A-A') (by sliding or rotation) relative to the shaft-receiving body (394). The inner moveable shaft (392b) is moveable in an axial direction (B-B') (by sliding or rotation) relative to the outer moveable shaft (392a). The respective axial (A-A', B-B') directions of movement may be parallel. Central axes of the outer moveable shaft (392a) and an inner moveable shaft (392b) may be parallel, preferably co-axial. The outer moveable shaft (392a) and the inner moveable shaft (392b) may be independently axially moveable. In a preferred configuration, the outer moveable shaft (392a) is axially moveable while the inner moveable shaft (392b) is stored within the outer moveable shaft (392a) passageway (3921).

The outer moveable shaft (392a) has distal end (2) that engages with the head of the subject, and an opposing proximal end (4). The distal end of the outer moveable shaft (392a) may be blunt ended. It may have a rounded circumferential edge (3926) (e.g. chamfered, bullet-shaped). The blunt ended distal end (2) allows the outer moveable shaft (392a) to contact the skin of the subject and to be swivelled relative to the intermediate head clamp (300) main body (310) (e.g. around axis 397) for optimal perpendicular placement with respect to the head of the subject without causing trauma. The distal end (2) of the outer moveable shaft (392a) hence blunt ended for atraumatic (glancing or passing) contact with skin of the subject's head.

The inner moveable shaft (392b) has distal end (2) that engages with the head of the subject, and an opposing proximal end (4). The distal end of the outer moveable shaft (392a) may be a pointed end (3925). The pointed end (3925) is narrowed to the extent that inner moveable shaft (392b) applies an engaging and locking force to the head of the subject so as to clamp the intermediate head clamp (300) main body (310). The pointed end (3925) may or may not be not be sharp so as to pierce the skin; it may terminate to a sphere or partial sphere which concentrates force. The combination of a blunt distal-ended outer moveable shaft (392a) and a pointed (3925) distal-end (2) inner moveable shaft (392b) in a telescopic arrangement allows atraumatic and accurate directional placement of moveable shaft (392)

against the skin when the inner moveable shaft (392*b*) is retracted within the passageway (3922) of the outer moveable shaft (392*a*), and once the direction is set, it allows the inner moveable shaft (392*b*) and its pointed end (3925) to be advanced linearly towards the head in the direction set by the outer moveable shaft (392*a*).

The extent of linear movement of the outer moveable shaft (392*a*) and of the inner moveable shaft (392*b*) may adjustable by sliding or rotation of the outer moveable shaft (392*a*) and an inner moveable shaft (392*b*) respectively.

An example of a telescopic moveable shaft (392) that uses rotation is used to adjust the linear position of outer moveable shaft (392*a*) and of the inner moveable shaft (392*b*) is shown in FIGS. 30A to D. Where rotation is used to adjust the linear position of outer moveable shaft (392*a*), the outer surface (3923) of the outer moveable shaft (392*a*) and the surface of the passageway (393) of the shaft-receiving body (394) are each threaded; the respective threads engage. Where rotation is used to adjust the linear position of inner moveable shaft (392*b*), the outer surface (3924) of the inner moveable shaft (392*b*) and the surface (3922) of the passageway (3921) of the outer moveable shaft (392*a*) are each threaded; the respective threads engage. The proximal end (4) of the outer moveable shaft (392*a*) may be disposed with a coupling element for a tool for rotation of the outer moveable shaft (392*a*). The proximal end (4) of the inner moveable shaft (392*b*) may be disposed with a coupling element for a tool for rotation of the inner moveable shaft (392*b*).

An example of a telescopic moveable shaft (392) that uses sliding is used to adjust the linear position of outer moveable shaft (392*a*) and of the inner moveable shaft (392*b*) is shown in FIGS. 31A to D. Where sliding is used to adjust the linear position of outer moveable shaft (392*a*), the outer surface (3923) of the outer moveable shaft (392*a*) and the surface of the passageway (393) of the shaft-receiving body (394) are each smooth; the respective smooth surfaces slidably engage. A locking mechanism may be provided to fix the linear position of the outer moveable shaft (392*a*) with respect to the shaft-receiving body (394). Where sliding is used to adjust the linear position of inner moveable shaft (392*b*), the outer surface (3924) of the inner moveable shaft (392*b*) and the surface (3922) of the passageway (3921) of the outer moveable shaft (392*a*) are each smooth; the respective smooth surfaces slidably engage. A locking mechanism may be provided to fix the linear position of the inner moveable shaft (392*b*) with respect to the outer moveable shaft (392*a*).

Provided is an intermediate head clamp (300) disposed with the plurality of clamps (390, *a-d*) disclosed above, wherein at least one, preferably all of the clamps (390, *a-d*) is telescopic as described above.

The main body (310) may be disposed with an IHC coupling (330) for repeatable dismountable attachment to a base end of a localizer, and/or to the operating table and/or to a Mayfield connector. The IHC coupling (330) may non-adjustably fix the pose and of the main body with respect to the base end of a localizer (e.g. to the IHC support frame (500), in particular to the frame base (510), in particular to one or more couplings (519, *a, b*) mentioned elsewhere herein), and/or to the operating table and/or to a Mayfield connector. The IHC coupling (330) may comprise an IHC coupling body (332) attached or attachable to the main body (310). The IHC coupling body (332) may be rigidly and permanently attached to the main body (310). The main body (310) and IHC coupling body (332) may be integrated into a one-piece unit, formed, for instance, by machine, molding, 3D printing. The IHC coupling body (332) may be dismountably attached to the main body (310). The IHC coupling body (332) may be dismountably attachable to the main body (310) using one or more fixtures (e.g. bolt).

The main body (310) may be disposed with an IHC fixer coupling for repeatable dismountable attachment to a working end of a 3DOF direction fixer (also called "fixer" herein). The IHC fixer coupling may be the same as or different from the IHC coupling (330). The fixer has a fixer base end attachable to the operating table and/or to a Mayfield connector, and a fixer working end attachable to the main body (310) via the IHC fixer coupling. The direction of the fixer working end is adjustable in relation to the fixer base end. The fixer base end is attachable in fixed relation to the operating table and/or to a Mayfield connector. The direction of the fixer working end can be changed and fixed around three intersecting axes of rotation. The point of intersection of the three axes and the centre (352) of the circular path of the intermediate head clamp (300) contact a line parallel to the operation table and coinciding with the rotation point of the head in the cervical spine (first & second cervical vertebrae), by concentric double arc system allowing rotation in each axis. The 3DOF direction fixer allows the direction of the head of the subject to be altered whilst on the operation table. When the IHC support frame (500) is attached to the IHC (300), and adjustment to the direction of the head via the 3DOF direction fixer also causes a direct relational change in the direction of the IHC support frame (500).

The IHC coupling body (332) may be disposed with one or more channels (334*a*, 334*b*) through which one or more fixation rods may be passed for attachment to the operating table. The one or more channels (334*a*, 334*b*) may be disposed in fixed and non-adjustable relation to the coupling body (332), and hence to the main body (310). A channel preferably runs in a direction from the superior side (312) to the inferior side (314). A channel preferably runs in a direction parallel to the axis of rotation (350) of the intermediate head clamp (300). The IHC coupling body (332) may be disposed on an upwards side of the main body. The IHC coupling body (332) may be disposed opposite to the side opening (324).

The intermediate head clamp may be made from any suitable material that provides the requisite strength and rigidity. The material may be non-ferrous to allow use with a medical imager. The material should also comply with the requirements of good surgical practice, e.g. be washable and sterilizable. Examples of suitable materials include polymers (e.g. polyethylene, polypropylene, polycarbonate, polyurethane), metals or alloys (e.g. aluminium, titanium), ceramic (silicon based), composites.

Figure 12:
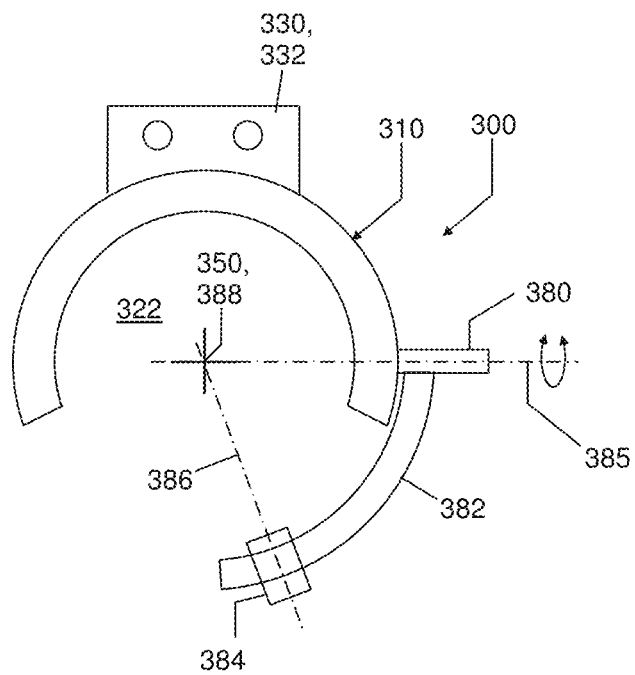
Figure 13:
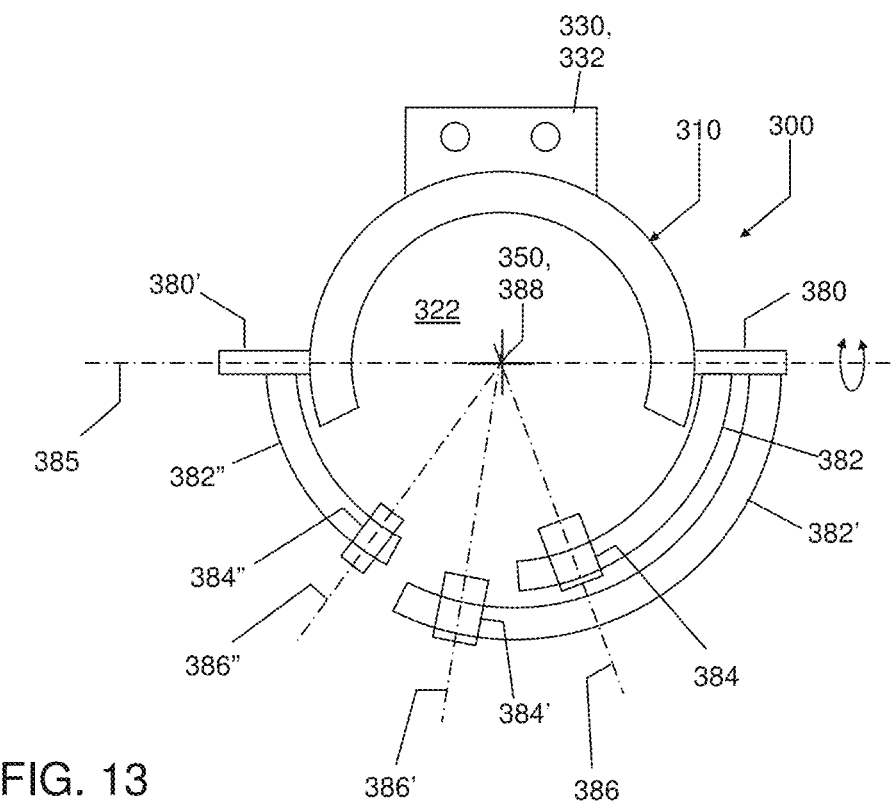
Figure 14:
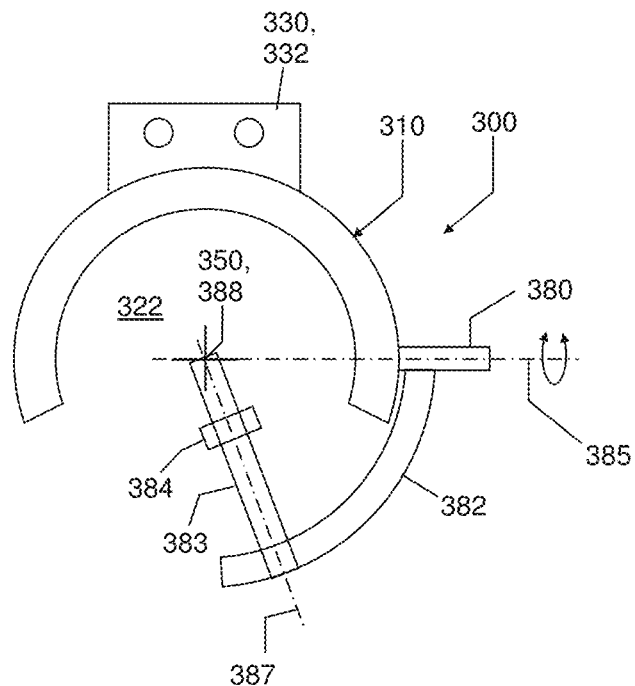

The intermediate head clamp (IHC) (300) may be provided with at least one IHC hub (380, 380') configured for dismountable attachment of at least one arc-shaped IHC supporting rail (382, 382', 382"). Exemplary IHC hubs (380, 380') are illustrated in FIGS. 12 to 14. The arc may be circular and planar. The IHC hub (380, 380') may be configured to allow rotation of the IHC supporting rail (382, 382', 382") around a rail axis of rotation (385) that crosses the axis of rotation of the intermediate head clamp (300). The IHC hub (380, 380') may be configured to position the IHC supporting rail (382, 382', 382") such that the centre of the IHC supporting rail arc (388) crosses the axis of rotation (350) of the intermediate head clamp (300). The radius of the IHC supporting rail arc (388) may be 12-16 cm.

The orientation of the IHC supporting rail (382, 382', 382") relative to the main body (310) may be adjustable and lockable. The number of IHC hubs (380, 380') may be 2, diametrically arranged around the axis of rotation (350) of the intermediate head clamp (300). An IHC hub (380, 380') may be configured to support a plurality of supporting rails (382, 382', 382") (e.g. FIG. 13). Where there is a plurality of IHC supporting rails (382, 382', 382"), the arc centre of each rail (388) may cross the axis of rotation (350) of the intermediate head clamp (300). Where there is a plurality of IHC supporting rails (382, 382') on one IHC hub (380), the IHC supporting rails (382, 382') may be concentrically arranged.

The IHC supporting rail (382, 382', 382") may be configured for slidable attachment of an instrument holder (384, 384', 384") (e.g. FIG. 13). The position on the IHC supporting rail may be adjusted and fixed, for instance, using a screw clamp or spring clamp. The IHC supporting rail (382, 382', 382") may be provided with a surface-marked measurement gauge; the measurement gauge is for reading-out a distance or angle of the instrument holder (384, 384', 384") with respect to the supporting rail (382, 382', 382"). The instrument holder (384, 384', 384") may be configured for dismountable attachment of an instrument. The instrument holder (384, 384', 384") may be non-dismountably attached to an instrument. The instrument holder may fix an instrument direction (386, 386', 386"), preferably the direction coincides with the axis of rotation (350) of the intermediate head clamp (300). Examples of instruments includes: skin retractor, muscle/bone flap retractor, dural retractor, brain spatula, exoscope.

The IHC supporting rail (382, 382', 382") may be configured for slidable attachment of a further IHC supporting rail (383) (e.g. FIG. 14). The further IHC supporting rail may have an arc-shape. The arc may be circular and planar. The centre of the further IHC supporting rail arc may cross the centre of the supporting IHC rail arc (388). The further IHC supporting rail (383) arc plane may have a direction (387) that crosses the axis of rotation (350) of the intermediate head clamp (300). The further IHC supporting rail may be configured for slidable attachment of the above-mentioned instrument holder (384). The position of the instrument holder (384) on the further IHC supporting rail may be adjusted and fixed, for instance, using a screw clamp or spring clamp. The further IHC supporting rail (383) may be provided with a surface-marked measurement gauge; the measurement gauge is for reading-out a distance or angle of the instrument holder with respect to the further supporting rail. The radius of the further IHC supporting rail arc (383) may be 12-16 cm.

A side-opening bridge (SOB) (3010) may be provided that is dismountably attachable to the intermediate head clamp (300) body (310) across the side opening. Exemplary side-opening bridges are shown in FIGS. 15 to 18. The pose of the side opening bridge (3010) attached to the intermediate head clamp (300) body (310) may be fixed and non-adjustable with respect to the axis of rotation (350) of the intermediate head clamp (300). The side opening bridge (3010) may span a geometric segment of the circular path of the movement guide (346, 346') that is between 60-180 deg.

Figure 15:
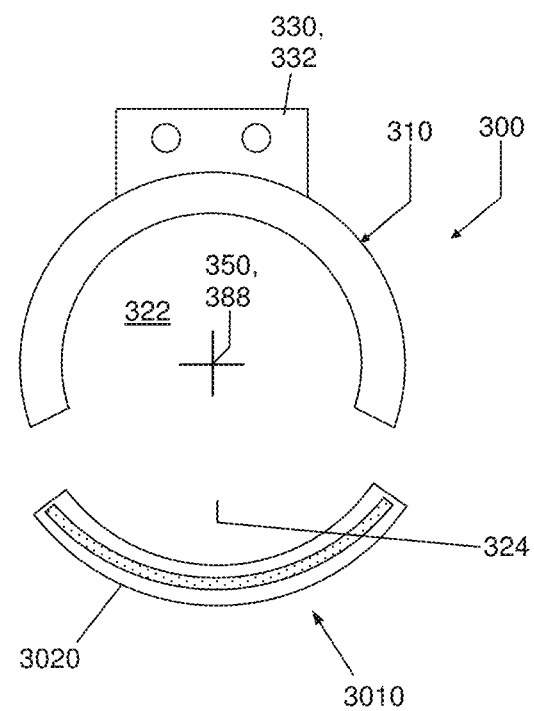
Figure 16:
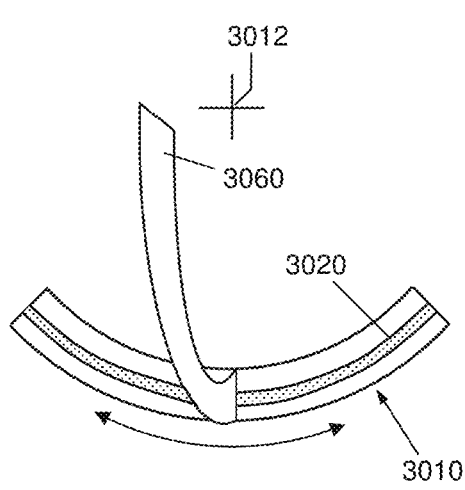

The side-opening bridge (3010) may be provided with a SOB (circular) arc-shaped supporting rail (3020) (e.g. FIGS. 15 and 16). The centre (3012) of the SOB supporting rail (3020) arc crosses the axis of rotation (350) of the intermediate head clamp (300) (when attached thereto). The SOB supporting rail (3020) may be configured for slidable attachment of a further SOB supporting rail (3060) (e.g. FIGS. 16 to 18).

The position of the further SOB supporting rail (3060) may be adjusted and fixed, for instance, using a screw clamp or spring clamp. The side-opening bridge (3010) may be provided with a surface-marked measurement gauge; the measurement gauge is for reading-out a distance or angle of the further SOB supporting rail (3060) with respect to the SOB supporting rail (3020). The further SOB supporting rail (3060) may have a (circular) arc-shape. The centre (3012) of the further SOB supporting rail (3060) arc may coincide with the centre of the SOB supporting rail arc. The radius of the SOB supporting rail (3060) may be 12-16 cm. The arcs of SOB supporting rail (3020) and of the further SOB supporting rail (3060) may be perpendicular.

Figure 17:
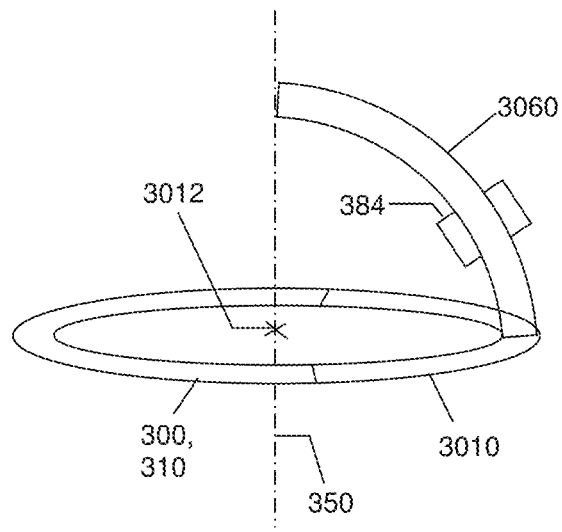

The further SOB supporting rail (3060) may be configured for slidable attachment of an instrument holder (384) (e.g. FIG. 17). The position on the further SOB supporting rail (3060) may be adjusted and fixed, for instance, using a screw clamp or spring clamp. The further SOB supporting rail (3060) may be provided with a surface-marked measurement gauge; the measurement gauge is for reading-out a distance or angle of the instrument holder (384) with respect to the further SOB supporting rail (3060). The instrument holder (384) may be configured for dismountable attachment of an instrument. The instrument holder (384) may be non-dismountably attached to an instrument. The instrument holder (384) may fix an instrument direction, preferably the direction coincides with the axis of rotation (350) of the intermediate head clamp (300). Examples of instruments includes: skin retractor, muscle/bone flap retractor, dural retractor, brain spatula, exoscope.

Figure 18:
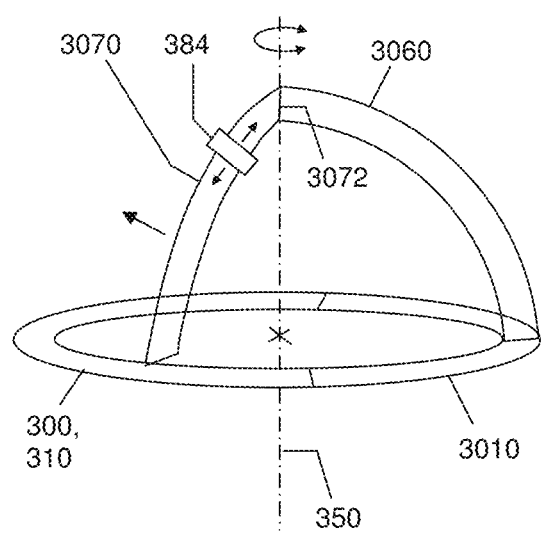
Figure 19:
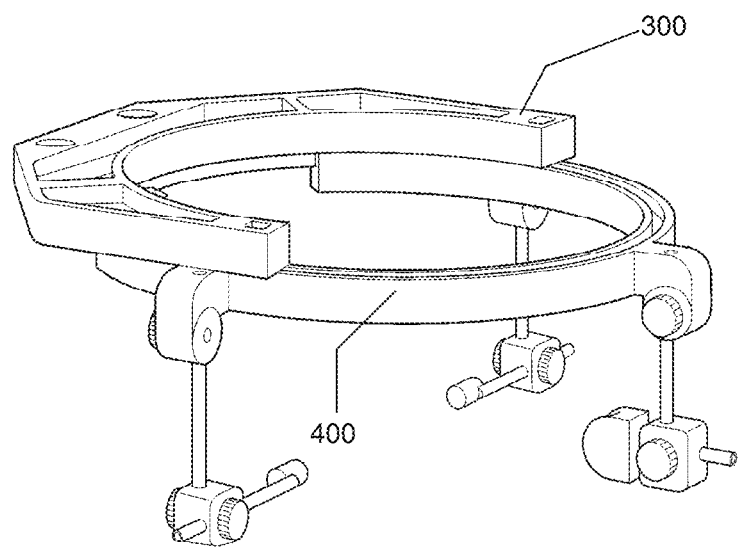

The further SOB supporting rail (3060) may be provided with a marking (circular) arc (3070) (e.g. FIG. 18). The marking arc may be attached at one end (3072) rotatably to further SOB supporting rail (3060), such that a centre of the marking arc crosses the axis of rotation (350) of the intermediate head clamp (300). By rotation of the marking arc (3070), the centre of the marking (circular) arc is maintained in the same position, which touches the axis of rotation (350) of the intermediate head clamp (300). The marking arc (3070) may be configured for slidable attachment of an instrument holder (384). The position on the marking arc (3070) may be adjusted and fixed, for instance, using a screw clamp or spring clamp. The marking arc (3070) may be provided with a surface-marked measurement gauge; the measurement gauge is for reading-out a distance or angle of the instrument holder (384) with respect to the marking arc. The instrument holder may be configured for dismountable attachment of an instrument. The instrument holder may be non-dismountably attached to an instrument. The instrument holder may fix an instrument direction, preferably the direction coincides with the axis of rotation (350) of the intermediate head clamp (300). Examples of instruments includes marker. By using the instrument holder (384) in combination with the further SOB supporting rail (3060), the user can mark on the skull accurately measured positions for attachment of one or more evoked potential (EP) electrodes.

Figure 34:
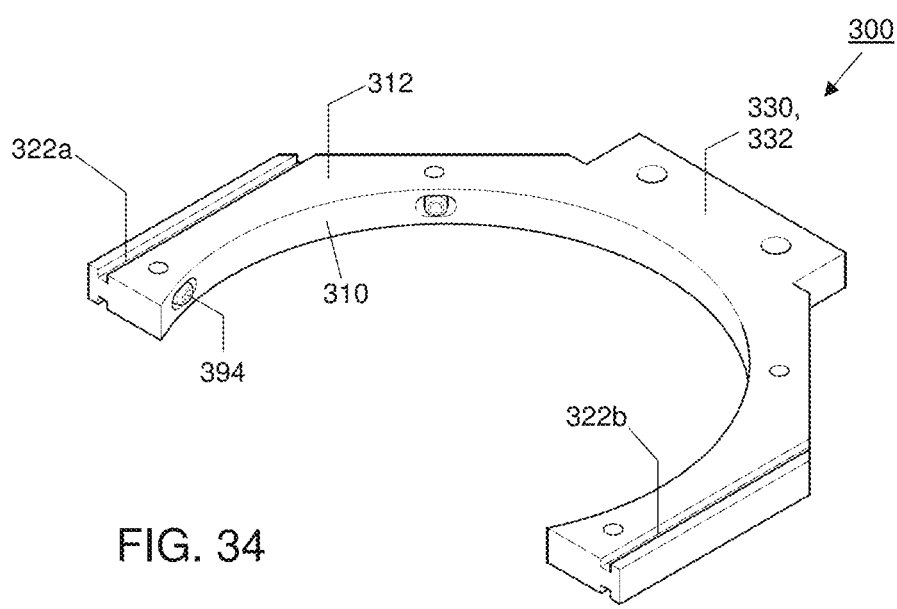

The intermediate head clamp (300), more in particular the main body (310), may be disposed with a pair of parallel movement guides (322a, 322b) for slidable attachment of a linear slidable positioning device. A view of the superior side (312) of the parallel movement guides (322a, 322b) is shown in FIG. 34. The parallel movement guides (322a, 322b) limit relative movement of the linear slidable positioning device along a guide path. The parallel movement guides (322a, 322b) describes a linear path of movement. The movement is planar. The parallel movement guides (322a, 322b) may be disposed on a superior side (312), or on an inferior side (314), of on both the superior side (312) and inferior side (314) of the intermediate head clamp (300). Each parallel movement guide (322a, 322b) is preferably disposed in the same plane. The parallel movement guides (322a, 322b) may comprise pair of a continuous or discontinuous protrusions or recesses or edges disposed mutually parallel and separated by the holding space (322). The parallel movement guides (322a, 322b) couple with a complementary continuous or discontinuous protrusion or recess or surface of a complementary part of the linear slidable positioning device.

The position of the linear slidable positioning device relative to the intermediate head clamp (300) can be locked. The position of the linear slidable positioning device can be adjusted by movement over the parallel movement guides (322a, 322b). The movement is parallel to the AC-PC line of the subject. The linear slidable positioning device comprises a base part and a moveable member. It moveable member may move in 2, 3, or more degrees of freedom relative to the base part. The position and optionally orientation of the moveable member may be lockable. The moveable member may support one or more devices (e.g. exoscope).

Just prior to the medical intervention, one or medial images is taken of the subject's (10) head (16) in the region of the brain (18). The medical images are typically three-dimensional. The anterior commissure (AC) (22) and posterior commissure (PC) (24) are determined from which an AC-PC line (30) is known. A midpoint of the AC (22) and PC (24) along the AC-PC line (30) is determined, which is also mid commissural point (MCP) (26). This MCP (26) is considered to be the centre of the brain.

From the one or medical images and knowledge of the MCP, distances of the adjustable protrusions (260) are determined by geometry and set to position the superior positioning cap (200) around the head of the subject so that:
 the planar (248) circular path of the superior positioning cap (200) is parallel with the AC-PC line (30), and/or
 the axis of reference (250) of the superior positioning cap (200) crosses the MCP (26),
 the MCP (26) is positioned within a height of the inferior positioning guide (400) when the superior positioning cap (200), intermediate head clamp (300), and superior positioning support (400) co-operate.

Figure 42A:
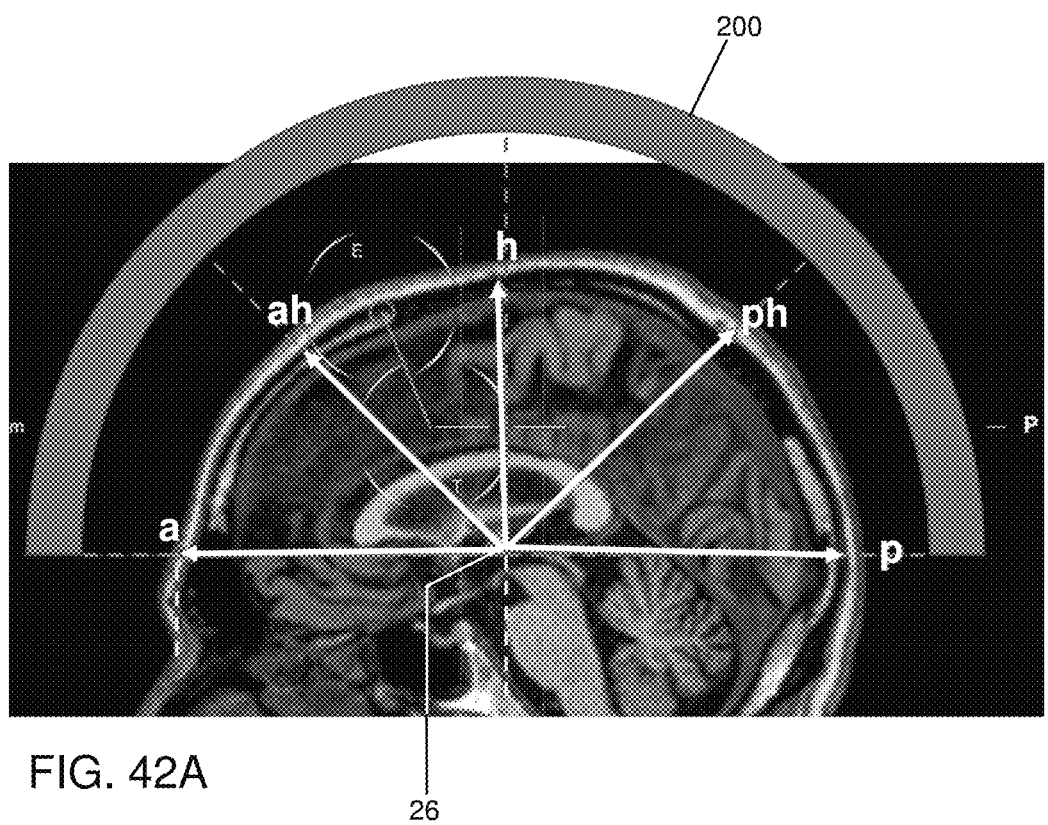
FIGS. 42A and 42B are medical imaging slices taken at the MCP in a posterior-anterior plane (42A) and in a lateral (left-right) plane (42B), together with a superior positioning cap and distance measurements.
Figure 42B:
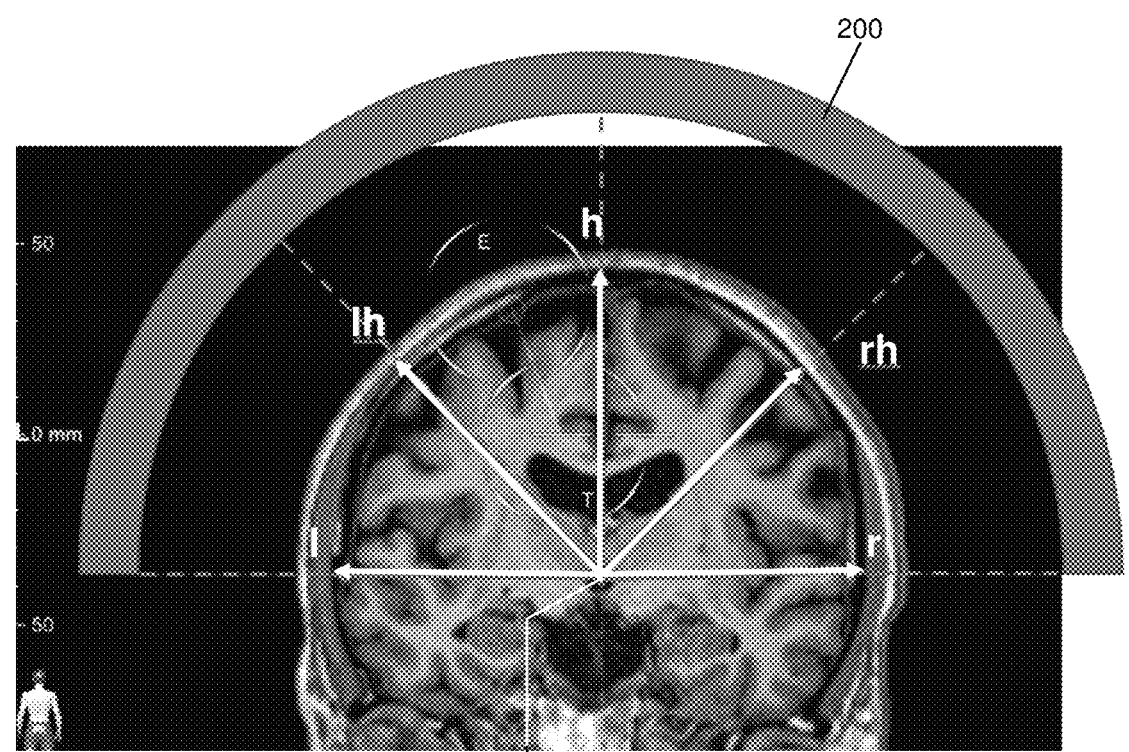

FIGS. 42A and 42B indicate exemplary measurements (a, ah, h, ph, p, where "p" is posterior and "a" is anterior; l, lh, h, rh, r, where "l" is left and "r" is right) taken from a 3D medical image from the MCP (26) to the edge of the skull. From the values a, ah, h, ph, p, l, lh, h, rh, r, the adjustable protrusions (260), optionally at corresponding positions to the measurements, can be set so the axis of reference (250) of the superior positioning cap (200) crosses the MCP (26).

From the one or medical images, and knowledge of the MPC (26), the pose of each locating body is determined by geometry and set to position the inferior positioning cap (400) around the head of the subject so that:
 the planar (448) circular path inferior positioning cap (400) is parallel with the AC-PC line (30), and/or
 the axis of reference (450) of the inferior positioning cap (400) crosses the MCP (26),
 the MCP (26) is positioned within a height of the inferior positioning guide (400).

After setting the adjustable protrusions (260) of the superior positioning cap (200) (SPC), and the locating bodies (460, 470, 480) of the inferior positioning support (400) (IPS), the IPS (400) is introduced around the head of the subject and the locating bodies (460, 470, 480) are located within the bodily recesses of the subject's head (e.g. in the nasion, left ear intratragic notch and right ear intratragic notch). The IPS clamps (490) are deployed to secure the IPS (400) to the head of the subject. The intermediate head clamp (300) (IHC) is introduced onto the IPS (400) main body (410) superior surface (412) such that the respective movement guides (446, 346') co-operate and the respective axes of rotation (450, 350) coincide (e.g. FIG. 19). The adjusted SPC (200) is introduced onto the IHC main body (310) superior surface (312) such that the respective movement guides (346, 246) co-operate and the axes of rotation (250) coincides with the SPC axis of reference (350) (e.g. FIG. 20). The SPC (200) main body (210) may be rotated around the axis of reference (250) until a radial marker on the SPC (200) main body aligns with a corresponding radial marker on the IPS (400) to ensure that the SPC (200) is correctly orientated.

The stack of SPC (200), IHC (300) and IPS (400) may be clamped together, e.g. using one or more clamps, elastic loops, and the like, to ensure tight mutual co-operation. The clamp may be a C-clamp. The clamp may have two arms, one arm that co-operates with the SPC (200) in particular with the supporting frame (210) inferior base part (240) (superior aide (242)), and the other arm that that co-operates with the IPS (400) in particular with the main body inferior side (414). The two arms are connected by a threaded member, and distance separating them adjusted by a nut (e.g. wing nut).

An angle of rotation of the IHC (300) may be set with respect to either or both of the superior positioning cap (200) and the IPS (400). The angle is chosen based on the location of the target in the subject and the planned route of access by the user (e.g. neurosurgeon). Once at the desired pose, the IHC (300) clamps (390) are deployed to secure the IHC (300) to the head of the subject. The SPC (200) and IPS (400) are removed. The IHC (300) pose is accurately set and fixed with respect to the MCP (26). Thereafter, the subject is mounted on the operating table, and the IHC (300) coupling is attached to the localizer base end. The intervention is performed, wherein a pose of the localizer effector end is known with respect to the localizer base end and hence with respect to the IHC (300) and to the MCP (26) and target.

Figure 21:
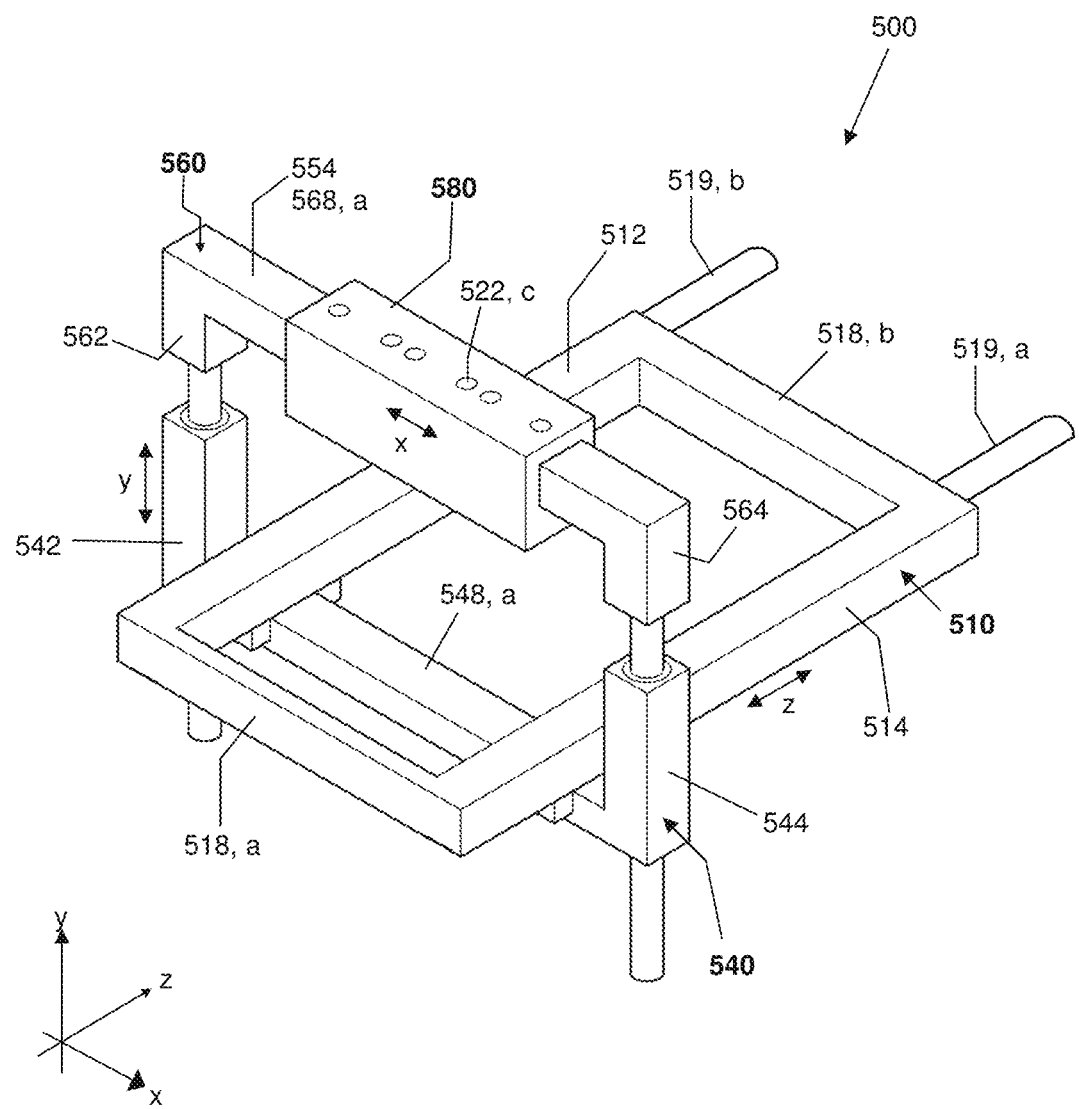
Figure 22:
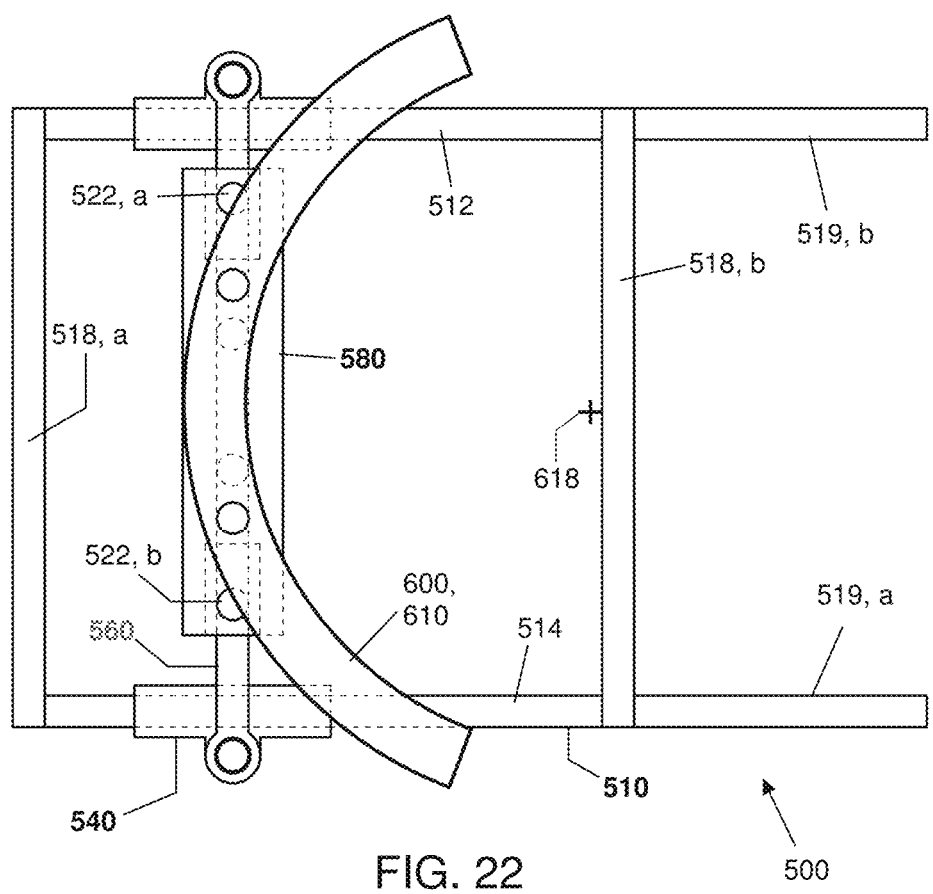
Figure 23:
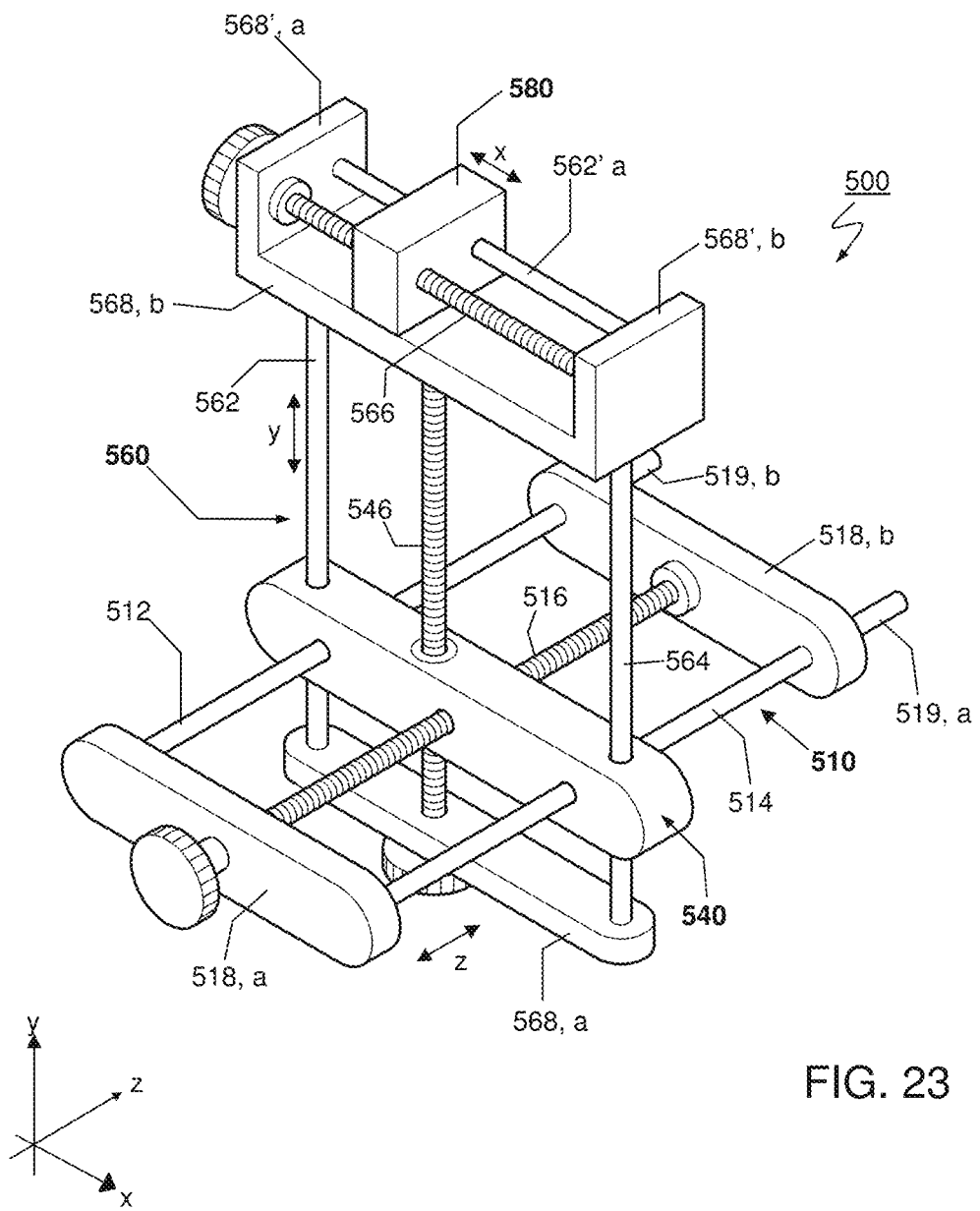

FIGS. 21, 22 and 23 show various views and variations of an IHC (300) support frame (500). The IHC (300) support frame (500) comprising a frame base (510) and a moveable member (580) whose position is adjustable and fixable in relation to three orthogonal axes (x-, z-, y-axes), relative the frame base (510).

The support frame (500) may comprise a kinetic chain of links or rigid bodies connected in series; each link may be connected to the next link by a prismatic joint. A prismatic joint is a 1 degree of freedom (1DOF only) sliding joint. The kinematic chain may comprise preferably four links connected in series, each link connected to the next link by the prismatic joint, the first link in the chain being the frame base (510), and the last (fourth) link being the moveable member (580), and the second and third link connecting the first and last links together. The three prismatic joints may be oriented in mutually perpendicular directions. The links and joints may be arranged in a gantry machine. At least one, preferably all of the prismatic joints and/or links may be disposed with a surface-marked measurement gauge or scale; the measurement gauge is for reading-out a distance setting of each joint link. It enables the position of the moveable member (580) to be manually set with respect to the frame base (510). The position may be set based on a 3D medical image.

The frame base (510) or first link (510) may be configured for repeatable non-adjustable attachment in fixed relation to the IHC (300). The frame base (510) may be configured for repeatable non-adjustable attachment in fixed relation to the operating table.

The second link (540) is attached to the frame base (510) by a kinematic joint having a (1DOF) direction of movement along an axis that is or is parallel to the z-axis. The z-axis is parallel to a planar surface of an operating table and parallel to a longitudinal axis of the operating table. The kinematic joint allows movement of the second link (540) along an axis that is or is parallel to the z-axis, for instance, parallel to a planar surface and longitudinal axis of the operating table The third link (560) is attached to the second link (540) by a kinematic joint having a (1DOF) direction of movement along an axis that is or is parallel to the y-axis. The y-axis is perpendicular to the z-axis. In particular, y-axis is perpendicular to a planar surface of the operating table. The kinematic joint allows movement of the third link (560) along the axis that is or is parallel to the y-axis that is or is parallel to the y-axis, for instance, perpendicular to a planar surface of the operating table The fourth link (580) or moveable member (580) is attached to the third link (560) by a kinematic joint having a (1DOF) direction of movement along an axis that is or is parallel to the x-axis. The x-axis is mutually perpendicular to the y-axis and z-axis. In particular, x-axis is parallel to a planar surface of the operating table and perpendicular to a longitudinal axis of the operating table. The kinematic joint allows movement of the fourth link (580) or moveable member (580) along the axis that is or is parallel to the x-axis, for instance, parallel to a planar surface of the operating table and perpendicular to a longitudinal axis of the operating table.

The IHC support frame (500) prismatic joints may each be motorised (e.g. hydraulically, pneumatically or electrically powered) to facilitate robotic control. The IHC support frame (500) prismatic joints may each be manually moveable (e.g. using a manually moveable screw-thread).

In a preferred embodiment, at least two of the first link, second link, and third link each comprise a pair of parallel bars or structures that slidably support and guide sliding movement of the higher link in the chain, and the pair of parallel bars in said link is mutually rigidly connected by one or more, preferably two interconnecting bars. The pair of parallel bars for part of the prismatic joint.

The moveable member may have an operation volume having a maximum movement span of a distance up to 150 mm along the z-axis (horizontal), of a distance up to 100 mm along the y-axis (vertical), of a distance up to 100 mm along the x-axis (vertical).

The IHC support frame (500) may be made from any suitable materials that provide the requisite strength and rigidity. The materials may be non-ferrous to allow use with a medical imager. The materials should also comply with the requirements of good surgical practice, e.g. be washable. It may be a sterilizable material also. Examples of suitable materials include polymers (e.g. polyethylene, polypropylene, polycarbonate, polyurethane), metals or alloys (e.g. aluminium, titanium), ceramic (silicon based), composites.

Where non-ferrous material have been used, the system can be used within medical imaging devices (in MRI, in CT scan) for stereotaxic procedures; this is an important feature of the present system, since most aiming devices all are outside of the imaging field.

The IHC support frame (500) can be used to set (manually or automatically) the position of the intermediate head clamp (300) with respect to the moveable member (580). The system (100) allows the centre of intermediate head clamp (300) (e.g. centre of rotation) to be aligned with the MCP of the subject and in a region parallel to and superior to the AC-PC line based on a medical image. A medical image also provides x-y-z distances allowing the IHC support frame (500) to be set (manually or automatically (e.g. motorised)) so that the moveable member (580) is aligned with the target (e.g. tumour, electrode target). The IHC system finds utility as a navigational device in medical care centres not disposed with an expensive navigation system.

Since the IHC support frame (500) is compact, it may be used with the intermediate head clamp (300) as a Halo Vest for treatment of a cervical spine fractures or as a skull fixation device in case of large skull deficits (as after a huge cranial decompression for trauma and edema), when the patient has to be kept in lateral position for a while. The pose of the intermediate head clamp (300) can be accurately set by the IHC support frame (500), thereby allowing healing.

The frame base (510) of the IHC support frame (500) or first link (510) may comprise two or more parallel bars (512, 514) (frame base bars (512, 514)) arranged in a plane. The parallel bars (512, 514) may be mutually connected by one or more interconnecting elements (e.g. rods, plates) (518, *a, b*) to increase rigidity of the frame base (510). These may be known as frame base interconnecting elements (518, *a, b*). The parallel bars (512, 514) may support and guide movement of the sliding second link (540). The second link (540) may slide across the parallel bars (512, 514). The parallel bars (512, 514) may form part of the prismatic joint. The frame base (510) with interconnecting elements may have a rectangular (e.g. square or oblong) of H-shaped form. One or more of the interconnecting elements (518, a, b) of the frame base (510) may be provided that extend out of the plane containing the parallel links; hence the frame base (510) may have a three-dimensional polyhedron form such a cuboid, pyramidal, prism, while one face of the polyhedron being planar and containing the aforementioned parallel links.

In FIGS. 21, 22 and 23, the frame base (510) is formed principally from components marked 512, 514, 518*a*, 518*b*.

Frame base (510) may comprise one or more couplings (519, *a, b*) for fixed attachment to the IHC (300), in particular to an IHC coupling (330). Frame base (510) may comprise one or more couplings for fixed attachment to operating table (e.g. via Mayfield connector). Frame base (510) may comprise one or more couplings (519, *a, b*) for fixed attachment to a phantom simulator (e.g. to a Target Point Simulator/Phantom).

The frame base (510) and/or second link (540) may be provided with a surface-marked measurement gauge; the measurement gauge is for reading-out a distance of one of the frame base (510) and/or second link (540) with respect to the other or to another reference such as the one or more couplings for fixed attachment to operating table.

A second link (540) is slidably attached to the first link (510) such that second link is moveable in 1DOF along the z-axis or z-direction. According to one embodiment, exemplified, for instance, in FIG. 21, the second link (540) may comprise two or more parallel bars (542, 544) arranged in a plane (second link bars (542, 544). The second link (540) may further comprise one or more interconnecting elements (e.g. rods, plates) (548, a, b) that connect the second link bars (542, 542) to increase rigidity of the second link (540). These may be known as second link interconnecting elements (548, a, b). The second link bars (542, 544) may support and guide sliding movement of the third link (560). The second link bars (542, 544) may form part of the prismatic joint. The third link (560) may slide across or into the second link bars (542, 544). The second link (540) with interconnecting elements (548, a) may have a "U", rectangular (e.g. square or oblong) of H-shaped form. Each second link bar (542, 544) may be slidably attached to a corresponding frame base bar (512, 514).

According to one embodiment, exemplified, for instance, in FIG. 23, the second link (540) may comprise a rigid body having a first guiding passage for each of the frame base parallel bars (512, 514) of the first link (frame base) (510). This allows sliding (1DOF) movement of the second link (540) along the parallel bars (512, 514) of the first link (frame base) (510). The direction of the first guiding passage is in the z-direction. The rigid body is further provided with a second guiding passage for each of the frame base parallel bars (562, 564) of the third link (560), wherein each second guiding passage is disposed perpendicular to a first guiding passage. The direction of the second guiding passage is in the y-direction. This allows (1DOF) sliding movement of the third link (560) along its parallel bars (562, 564) with respect to the second link (540). The guiding passages may form part of the prismatic joint.

In FIG. 23, the second link (540) is formed principally from the component marked 540. In FIG. 21, the second link (540) is formed principally from components marked 542, 544, 548, a.

Movement of the second link (540) in the z-direction may be motorised (e.g. hydraulically, pneumatically or electrically powered) to facilitate robotic control. Movement of the second link (540) in the z-direction may be manual. Under manual control, the movement of the joint may be controlled, for instance, by a screw-thread to convert rotation into a linear movement. In FIG. 23, the movement of second link (540) along the z-axis is controlled by screw-thread (516).

The second link (540) and/or third link (560) may be provided with a surface-marked measurement gauge; the measurement gauge is for reading-out a distance of one of the second link (540) and/or third link (560) elements with respect to the other or to another reference such as the frame base.

A third link (560) is slidably attached to the second link (540) such that third link (560) is moveable in 1DOF along the y-axis or y-direction.

According to one embodiment, exemplified, for instance, in FIG. 23, the third link (560) may comprise two or more parallel bars (562, 564) arranged in a plane (third link bars (562, 564)). The third link (560) may further comprise one or more interconnecting elements (e.g. rods, plates) (568, a, b) that connects the third link bars (562, 564) to increase rigidity of the third link (560). These may be known as third link interconnecting elements (568, a, b). The third link bars (562, 564) may support and guide sliding movement of the third link (560) within the second guiding passages of the second link (560). The third link bars (562, 564) may form part of the kinematic joint. The third link (560) with interconnecting elements (568, a, b) may have a rectangular (e.g. square or oblong) of H-shaped form. Each third link bar (562, 564) may be slidably (1DOF) attached to a second link (540). In FIG. 23 each third link bar (562, 564) is attached a body of the second link (540), passing through second guiding passages therein. The third link bars (562, 564) may form part of the prismatic joint In FIG. 23, the third link (560) is formed principally from components marked 564, 566, 568 a, b.

According to one embodiment, exemplified, for instance, in FIG. 21, third link (560) may comprise two or more parallel bars (562, 564) arranged in a plane (third link bars (544, 546)). The third link (560) may further comprise one or more interconnecting elements (e.g. rods, plates) (568, a) that connect the third link bars (562, 564) to increase rigidity of the third link (560). These may be known as third link interconnecting elements (548, a). The third link bars (562, 564) may support and guide sliding movement of the third link (560) within the parallel bars (542, 544) of the second link (540). The third link bars (562, 564) may form part of the prismatic joint. The third link (560) with interconnecting elements (568, a) may have a rectangular (e.g. square or oblong) of H-shaped form. In FIG. 21, the third link (560) is formed principally from components marked 562, 564, 548 a.

Movement of the third link (560) in the y-direction may be motorised (e.g. hydraulically, pneumatically or electrically powered) to facilitate robotic control. Movement of the third link (560) in the y-direction may be manual. Under manual control, the movement of the joint may be controlled, for instance, by a screw-thread to convert rotation into a linear movement. In FIG. 23, the third link (560) is controlled by screw-thread 546.

The third link (560) and/or fourth link (570) may be provided with a surface-marked measurement gauge; the measurement gauge is for reading-out a distance of one of the third link (560) and/or fourth link (570) elements with respect to the other or to another reference such as the frame base.

A fourth link (580) also known as the moveable member (580) is slidably attached to the third link (560) such that fourth link (580) is moveable in 1DOF along the x-axis or x-direction.

The moveable member (580) typically comprises a rigid body. The moveable member (580) may be disposed with at least one guiding passage that slidably receives a bar or rod of the $3^{rd}$ link. The direction of the guiding passage is in the x-direction.

In FIG. 21 the moveable member (580) is disposed with a guiding passage that slidably receives the interconnecting elements (568, a) of the $3^{rd}$ link (360). The moveable member (580) is engaged with the interconnecting element (568, a) of the $3^{rd}$ link (360) and is slidable along the interconnecting element (568, a) in the x-direction.

In FIG. 23 the moveable member (580) is disposed with a guiding passage that slidably receives a guiding x-bar (562', a) rigidly attached to the $3^{rd}$ link (360). The guiding bar x-bar (562', a) is orientated parallel to an x-direction, along the x-axis. The guiding x-bar (562', a) is attached to the interconnecting element (568, b) of the $3^{rd}$ link (360). It is attached to the upper interconnecting element (568, b) of the $3^{rd}$ link (360). In the figure, there are two supporting x-bar interconnecting elements (568', a, b), that rigidly connect the guiding x-bar (562', a) to the interconnecting element (568, b) of the $3^{rd}$ link (360).

The moveable member (580) may be disposed with one or more coupling points (522, a, b, c) for repeatable dismountable attachment to a dismountable unit (600). The attachment may be non-adjustable. The attachment may be fixed e.g. for a duration of the intervention. The frame base may be disposed with a coupling configured for repeatable dismountable attachment in fixed relation to the IHC (300). The attachment may be non-adjustable.

Movement of the moveable member (580) in the x-direction may be motorised (e.g. hydraulically, pneumatically or electrically powered) to facilitate robotic control. Movement of the moveable member (580) in the x-direction may be manual. Under manual control, the movement of the joint may be controlled, for instance, by a screw-thread to convert rotation into a linear movement. In FIG. 23, the moveable member (580) is controlled by screw-thread (566).

The third link (560) and/or fourth link (580) may be provided with a surface-marked measurement gauge; the measurement gauge is for reading-out a distance of one of the third link (560) and/or fourth link (580) elements with respect to the other or to another reference such as the frame base.

Figure 24:
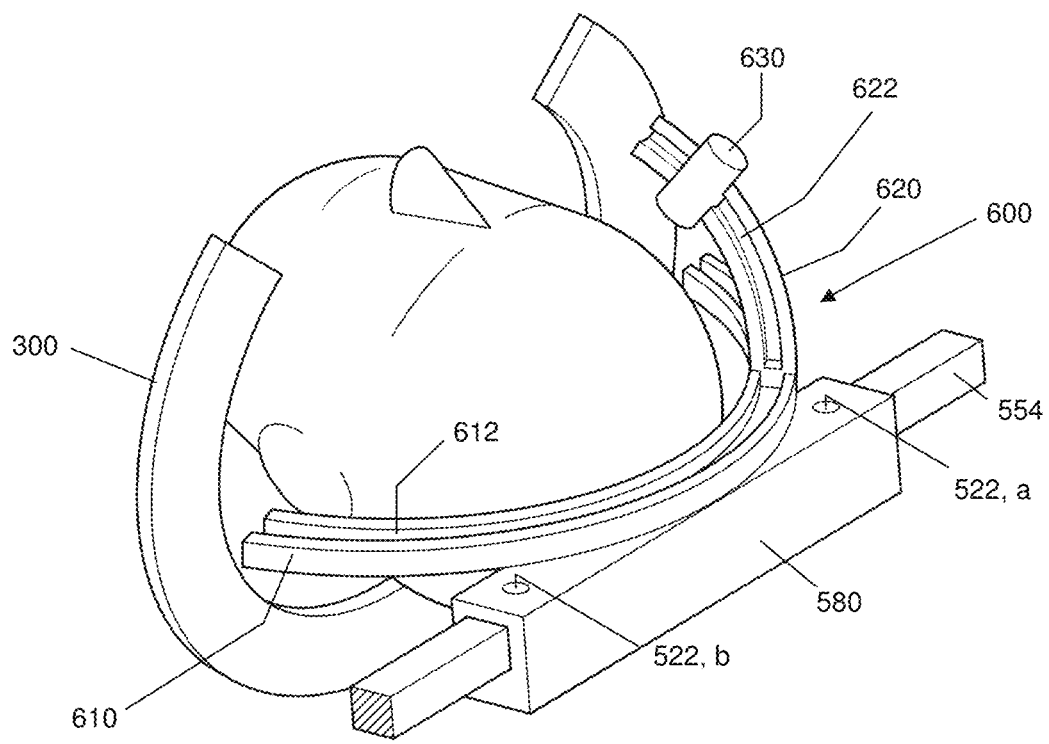

The dismountable unit (600) may comprise a fixed alpha arm (FAA) (610) configured for dismountable attachment in fixed relation to the coupling points (522) of the moveable member (580). An example of dismountable unit (600) FAA (610) attached to the moveable member (580) of the IHC support frame (500) is shown in FIGS. 22 and 24. In particular, the coupling to the moveable member may be non-adjustable. The fixed alpha arm (610) may be disposed with an arc-shaped supporting rail (612). The arc may be circular and planar.

The radius of the arc may be 12-16 cm. The position of the FAA supporting rail arc is adjusted by the IHC support frame until the centre of the arc (618) crosses the target of treatment of the subject. With the IHC centred on the MCP, and with a medical image of the subject indicating both the position of the MCP and of target, the adjustment of the IHC support frame axes can be determined to move the moveable member and bring the AA supporting rail arc centre into alignment with the target.

The FAA supporting rail may be configured for slidable attachment of a beta arm (BA) (620). The position of beta arm (620) on the FAA supporting rail (612) may be adjusted and fixed, for instance, using a screw clamp or spring clamp. An exemplary beta arm (620) is shown in FIG. 24. The FAA supporting rail (612) may be provided with a surface-marked measurement gauge; the measurement gauge is for reading-out an angle of the BA (620) with respect to the FAA supporting rail (612). The beta arm (620) may be configured for dismountable attachment to the fixed alpha arm (610). The beta arm may be configured for non-dismountable attachment to the fixed alpha arm.

The beta arm (620) may be provided with a beta arm (BA) supporting rail (622) configured for slidable attachment of a beta arm (BA) instrument holder (630). The BA supporting rail (622) may have an arc-shape. The arc may be circular and planar. The centre of the BA supporting rail (622) arc may cross the centre of the FAA supporting rail (612) arc, or it may be offset from the centre of the FAA supporting rail (612) arc by an offset value to take account of a dimension of BA instrument holder. The centre of the BA supporting rail arc may the centre of the target, or it may be offset from the centre of the target by an offset value to take account of a dimension of BA instrument holder. The BA supporting rail (622) arc plane (optionally extended) may cross the target or it may be offset from the target by an offset value to take account of a dimension of BA instrument holder. The aforementioned offset value shifts the centre of the centre of the BA supporting rail (622) arc so that the direction of an instrument mounted in the BA instrument holder (630)—which BA instrument holder (630) may introduce a displacement—is corrected so that crosses the target.

The BA supporting rail may be configured for slidable attachment of the beta arm (BA) instrument holder (630). The position of the BA instrument holder (630) on the BA supporting rail (622) may be adjusted and fixed, for instance, using a screw clamp or spring clamp. The beta arm (620) or BA supporting rail (622) may be provided with a surface-marked measurement gauge; the measurement gauge is for reading-out a distance or angle of the BA instrument holder with respect to the BA supporting rail (622). The radius of the BA supporting rail (622) arc may be 12-16 cm. The BA instrument holder (630) may be configured for dismountable attachment of an instrument. The BA instrument holder (630) may be non-dismountably attached to an instrument. The BA instrument holder may fix an instrument direction. The instrument direction preferably crosses the centre of the FAA supporting rail arc (612), and the target. The instrument direction preferably crosses the centre of the BA supporting rail (622) arc, or it may be offset from the centre of the BA supporting rail (622) arc by an offset value to take account of a dimension of BA instrument holder. Examples of instruments includes those for stereotactic interventions, including deep brain stimulation probes. The arcs of FAA supporting rail (612) and of the BA supporting rail (622) may be perpendicular.

The dismountable unit (600) may comprise at least one moveable member (MM) hub assembly (700) configured for dismountable attachment in fixed relation to the coupling points (522) of the moveable member (580). Examples of hub assemblies (700) are shown in FIGS. 25 to 28. The MM hub assembly (700) may be configured for dismountable attachment of at least one arc-shaped moveable member hub (MMH) supporting rail (720). The arc may be circular and planar. The radius of the arc may be 12-16 cm.

The position of the MMH supporting rail (720) is adjusted by the IHC support frame until the centre of the arc crosses the target of treatment of the subject. With the IHC centred on the MCP, and with a medical image of the subject indicating both the position of the MCP and of target, the adjustment of the IHC support frame axes can be determined to move the moveable member and bring the MMH supporting rail arc centre into alignment with the target. The MM hub assembly (700) may be configured to allow rotation of the MMH supporting rail (720) around a rail axis of rotation. The rail axis of rotation crosses the target of treatment of the subject.

The MM hub assembly (700) may comprises a MM hub (710, a, b), configured for dismountable attachment of at least one MMH supporting rail (720). The MM hub (710, a, b) may be configured to allow rotation of the MMH supporting rail (720) around a rail axis of rotation (716) that crosses the target of treatment of the subject. The radius of the MMH supporting rail (720) may be 12-24 cm, for instance 12-16 cm.

The orientation of the MMH supporting rail (720) relative to the moveable member (580) may be adjustable and lockable. The number of MM hubs (710, a, b) may be 2, diametrically arranged around the axis of rotation (716). An MM hub (710, a, b) may be configured to support a plurality of MMH supporting rails (720). Where there is a plurality of MMH supporting rails (720), the arc centre of each rail (718) may cross at the same point. Where there is a plurality of MMH supporting rail (720) on one MM hub (710, a, b), the MMH supporting rail (720) may be concentrically arranged.

The MM hub assembly (700) may comprises a y-axis extender (712, a, b), configured to raisethe position of MM hub (710, a, b) relative to the moveable member. In particular, the extender (712, a, b) may be configured to raise position of attachment of the MMH supporting rail relative to the moveable member in a y-direction. By raising the position of the MM hub (710, a, b), the axis of rotation of the MMH supporting rail is also raised. The extender (712, a, b) may comprise an extender coupling, configured for attachment to the moveable member coupling points (522).

The MM hub assembly (700) may comprises an MMH base (714) configured for dismountable attachment in fixed relation to the coupling points (522) of the moveable member (580), which base also supports the MM hub (710, a, b) and extender (712, a, b) where present. The base is typically rigid in order to stably anchor the MM hub (710, a, b) to the moveable member (580). The MMH base (714) may be disposed with one or more coupling points (715) to facilitate attachment to the coupling points (522) of the moveable member (580). The MMH base (714) may comprise two arms (717, a, b) that extend in an inferior direction (towards feet of subject). The arms (717, a, b) may be straight or curved. The arms displace the MM hub assembly (700) in a z-direction away from the moveable member (580) of IHC (300) support frame (500), such that the rail axis of rotation (716) crosses the target of treatment of the subject.

The orientation (around the axis of rotation (716)) of the MMH supporting rail (720) relative to the MM hub (710, a, b) may be adjustable and lockable. The number of MM hubs may be 2 arranged such that their axes of rotation is co-axial, and preferably parallel to the x-axis direction of movement of the moveable member. A MM hub may be configured to support a plurality of MMH supporting rails. Where there is a plurality of MMH supporting rails (720, 724, 725, FIG. 27) on a MM hub (710, a), the arc centre (718) of each rail may cross the same point; the target of treatment of the subject. Where there is a plurality of MMH supporting rails (720, 724, 725, FIG. 27) on one MM hub (710, a, b), the supporting rails (720), may be concentrically arranged. A MMH supporting rail (720, 723, 724, 725, 726) may be attached at both ends to a MM hub (710, a and b) and open at the other end. A MMH supporting rail (720, 722) may be attached at either end to a MM hub (710, a and b).

Figure 25:
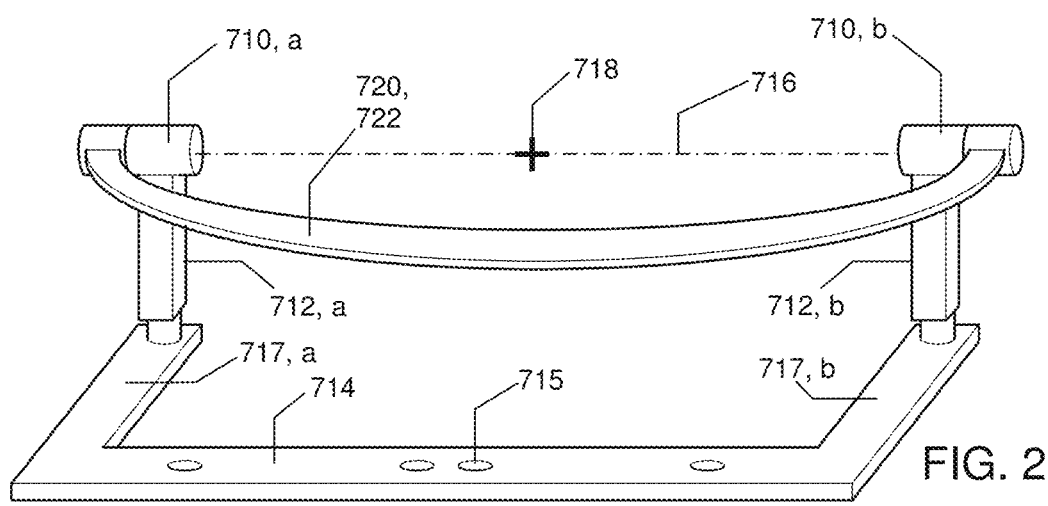
Figure 26:
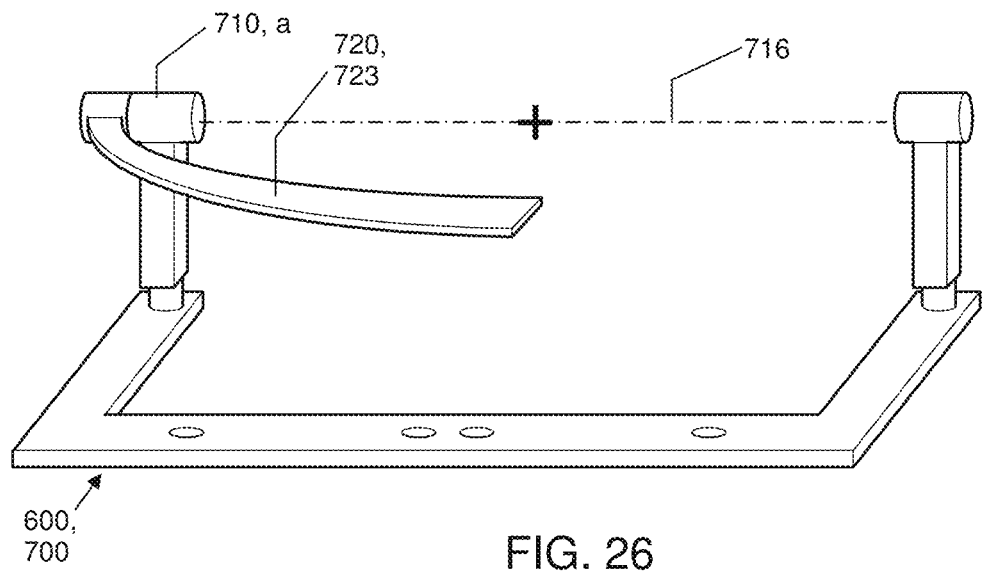
Figure 27:
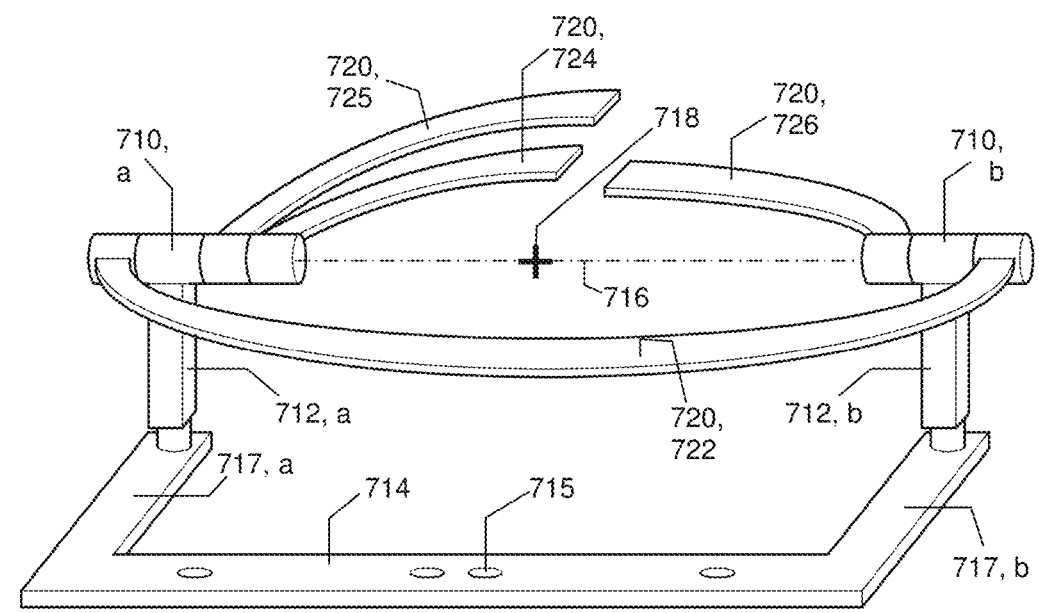

A MMH supporting rail (720) may be an arm rest (722), configured to support a part of the arm of the user (e.g. surgeon) such as the wrist. An example of an arm rest (722) is shown in FIG. 25. The arm rest (722) is preferably arc-shaped. The arm rest may be attached at either end to a MM hub (710, a and b). The arm rest (722) may be tiltable; the angle of tile adjustable and lockable.

The MMH supporting rail (720, 723-726) may be configured for slidable attachment of an instrument holder. The position on the MMH supporting rail (720) may be adjusted and fixed, for instance, using a screw clamp or spring clamp. The MMH supporting rail (720) may be provided with a surface-marked measurement gauge; the measurement gauge is for reading-out a distance or angle of the instrument holder with respect to the MMH supporting rail (720). The instrument holder may be configured for dismountable attachment of an instrument. The instrument holder may be non-dismountably attached to an instrument. The instrument holder may fix an instrument direction, preferably the direction coincides with the axis of rotation (350) of the MM hub. Preferably the direction coincides with the target. Examples of instruments include skin retractor, muscle/bone flap retractor, dural retractor, brain spatula, exoscope.

Figure 28:
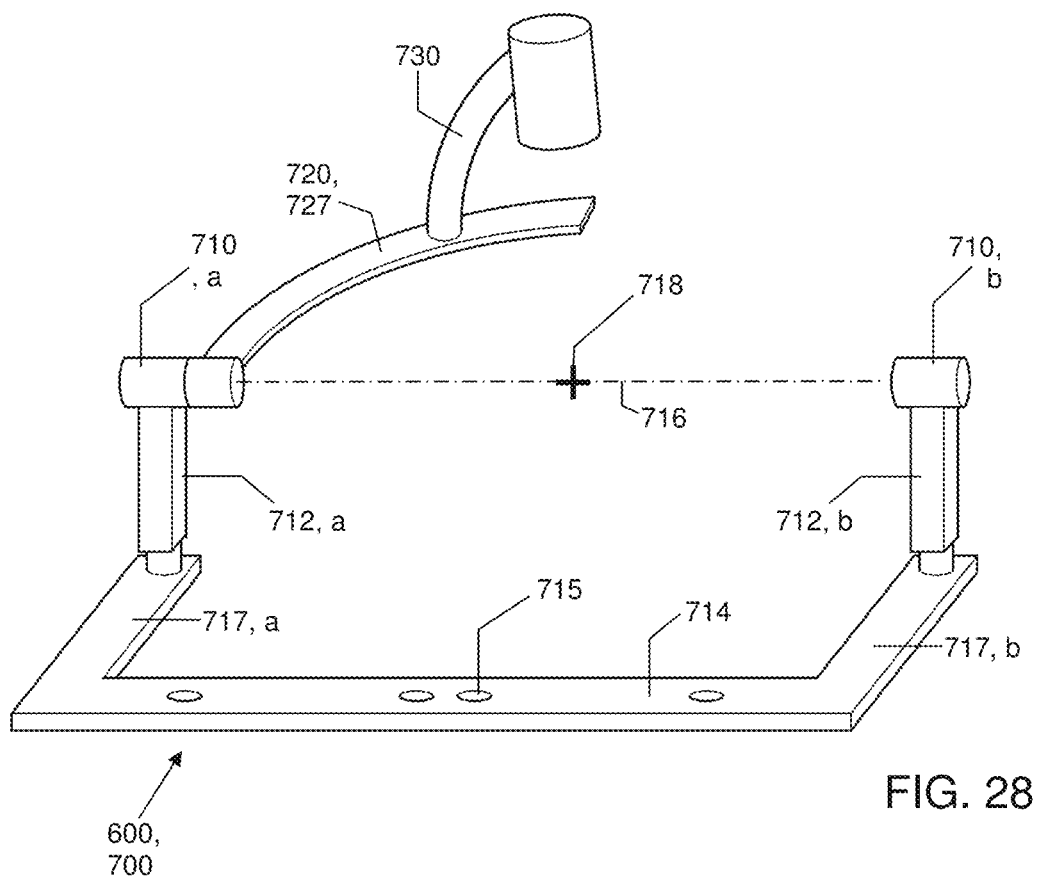

The MMH supporting rail (720) may be configured for slidable attachment of a further MMH supporting rail (730). An example of a further MMH supporting rail (730) is shown in FIG. 28. The further MMH supporting rail (730) may have an arc-shape. The arc may be circular and planar. The centre of the further MMH supporting rail arc may cross the centre of the MMH supporting rail arc (718), or the axis of rotation (716) of the MM hub, or the target. The further MMH supporting rail (730) arc plane may have a direction that crosses axis of rotation (716) of the MM hub.

The further MMH supporting rail (730) may be configured for slidable attachment of the above-mentioned instrument holder. Examples of instruments include skin retractor, muscle/bone flap retractor, dural retractor, brain spatula, exoscope. The position of the instrument holder on the further MMH supporting rail (730) may be adjusted and fixed, for instance, using a screw clamp or spring clamp. The further MMH supporting rail (730) may be provided with a surface-marked measurement gauge; the measurement gauge is for reading-out a distance or angle of the instrument holder with respect to the further MMH supporting rail. The radius of the further MMH supporting rail (730) arc may be 12-16 cm.

An IHC system comprises an IHC support frame (500) described herein, and an intermediate head clamp (300) as described herein. An IHC system may comprise an IHC support frame (500) described herein, and an intermediate head clamp (300) as described herein, and a dismountable unit (600) as described herein. The IHC system allows the centre of intermediate head clamp (300) (e.g. centre of rotation) to be aligned with the reference point of the subject (MCP of the subject and in a region parallel to and superior to the AC-PC line), and the IHC support frame (500) to be adjusted so that the dismountable unit (600) is aligned with the target.

When the dismountable unit (600) comprises a fixed alpha arm (FAA) (610), the arc-shaped supporting rail (612), the IHC support frame (500) may be adjusted so that the arc-shaped supporting rail (612) is aligned with the target. When dismountable unit (600) comprises a moveable member (MM) hub assembly (700), the IHC support frame (500) may be adjusted so that the centre of the arc of the arc-shaped moveable member hub (MMH) supporting rail (720) crosses the target of treatment of the subject.

The intermediate head clamp (300) can be positioned at the reference point (MCP/AC-PC line) of the subject's head, using for instance, the system (100) described herein, based on a medical image. The medical image provides a plurality of distances allowing the adjustable positioning protrusions (260, a, b, c, d, e) of the superior positioning cap (200) to be set (manually or automatically) so that the intermediate head clamp (300) is positioned at said reference point. The medical image also provides x-y-z distances allowing the IHC support frame (500) to be set (manually or automatically (e.g. motorised)) so that the dismountable unit (600) is aligned with the target (e.g. tumour, electrode target). The IHC system finds utility as a navigational device in medical care centres not disposed with an expensive navigation system. In particular, as distances can be set manually, interventions can be performed in situation where live imaging or other navigational tools are not available, as is frequent in developing countries.

Since the intermediate head clamp (300) is centered on the reference point (MCP/AC-PC line) of the subject's head, the intermediate head clamp (300) constantly can be used as mechanical reference for cerebral procedures (e.g. in traumatology): the position of the dismountable unit (600) can be adjusted accurately by the IHC support frame (500) by movement (manual or motorised) along the x-y-z axes.

Just prior to the medical intervention, one or medical images are taken of the subject's head in the region of the brain. The medical images are typically three-dimensional.

The anterior (12) commissure (AC) (22) and posterior (14) commissure (PC) (28) are determined from which an AC-PC line (30) is known. A midpoint of the AC (22) and PC (28) along the AC-PC line (30) is determined, which is also mid commissural point (MCP) (26). This MCP (26) is considered to be the centre of the brain.

As mentioned earlier, the intermediate head clamp (300) pose is accurately set and fixed with respect to the MCP (26), using the superior positioning cap (200) and the inferior positioning cap (400). The subject is then positioned on the operating table, and the intermediate head clamp (300) is attached in fixed relation to the operating table using the IHC coupling (330). The IHC support frame base (510) is fixed relation to the intermediate head clamp (300) via the IHC coupling (330).

With the intermediate head clamp (300) centred above the MCP, and with a medical image of the subject indicating both the position of the MCP and of target, the adjustment of the IHC support frame axes can be determined to move the moveable member and bring the moveable member and the dismountable unit (600) into alignment with the target.

Figure 35:
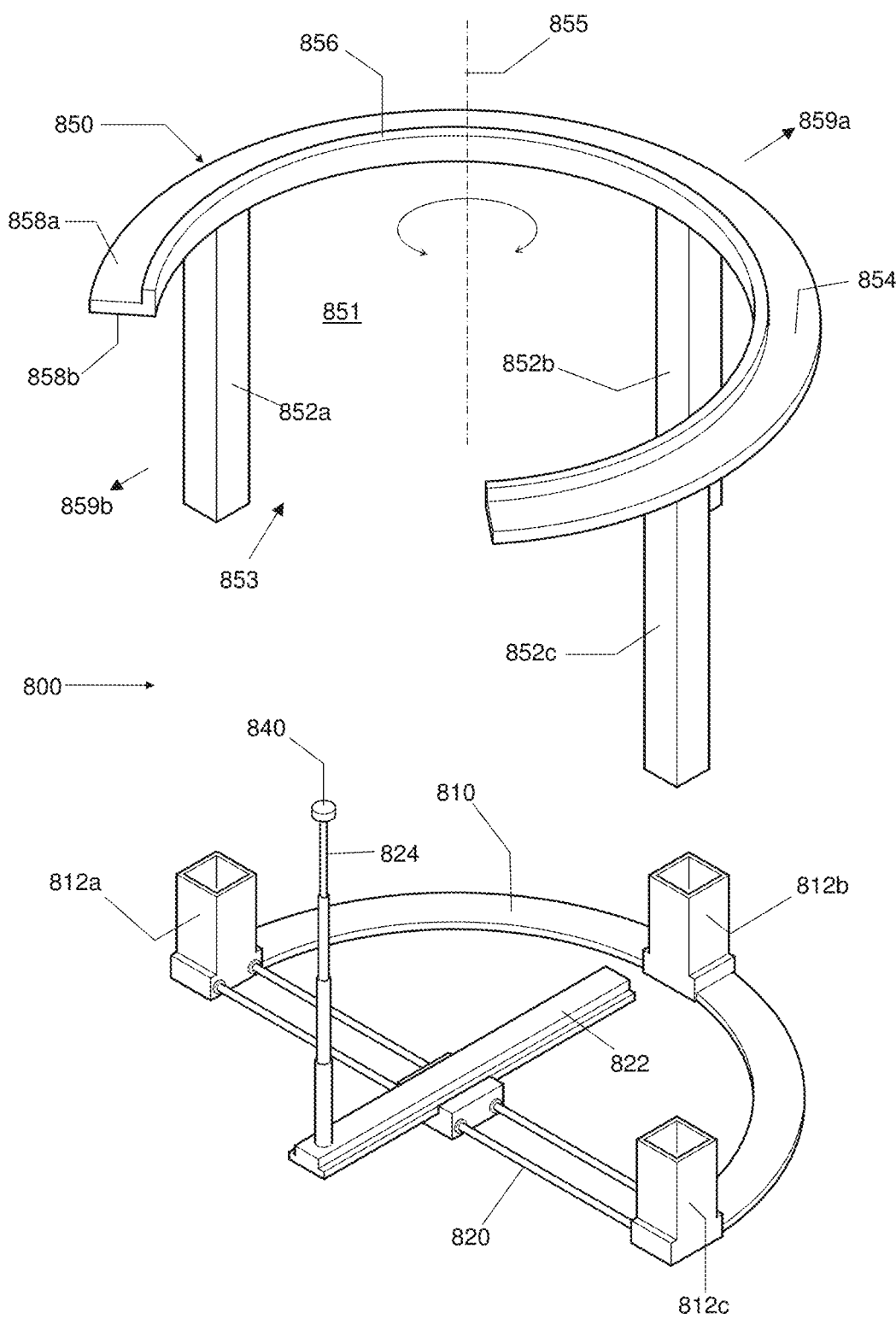
Figure 36:
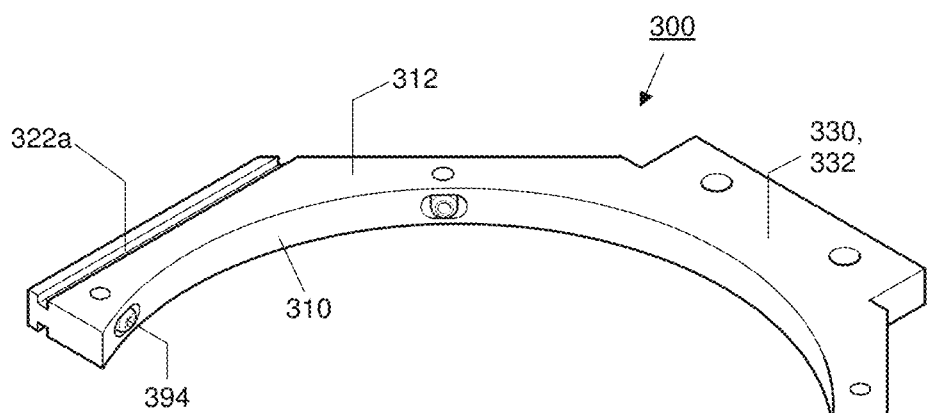
Figure 37:
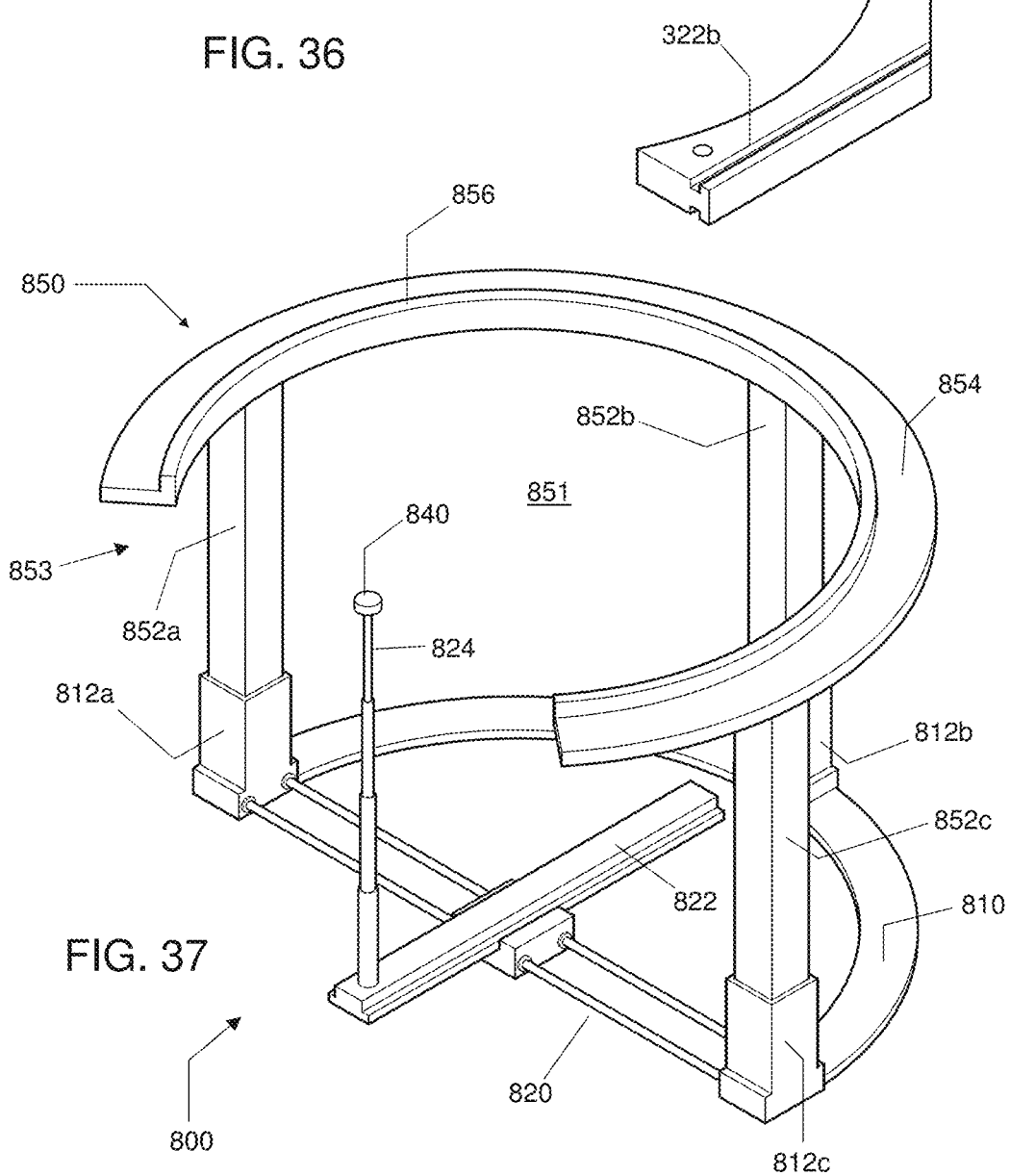
Figure 38:
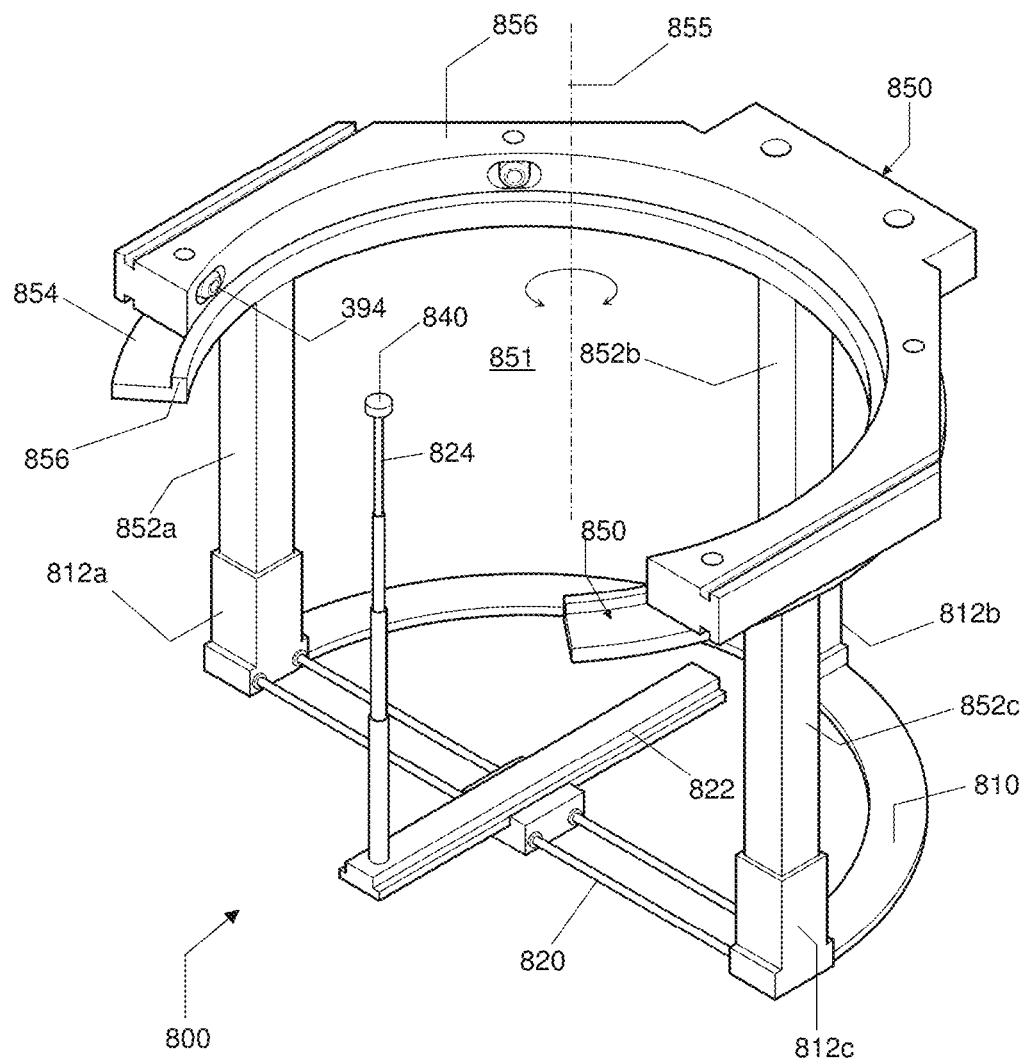

Provided is a phantom (800) that reproduces the spatial position and optionally orientation of the target for treatment of the subject relative to the intermediate head clamp (300). The phantom (800) comprises a phantom base (810) and a target body (840) whose spatial position and optionally orientation is moveable and fixable relative to the phantom base (810). An exemplary phantom (800) is depicted in FIGS. 35, 37, 38. The target body (840) is moveable in at least 3 DOFs relative to phantom base (810). The at least 3 DOFs of movement may be achieved by a plurality of links (820, 822, 840), each connected by a prismatic or revolute joint. Preferably, the 3DOF are realised by a chain of three links (820, 822, 840), each link being slidable along a different axis linear axes, the linear axes being mutually perpendicular (i.e. x, y, z). The link (824) attached to the target body (840) is part of a telescopic assembly; it is appreciated that a telescopic assembly is just one way to implement a prismatic joint. The phantom (800) may be further provided with one or more surface-marked measurement gauges for manually setting the position and optionally orientation of the target body (840). Each joint and/or link of the phantom (800) may be disposed with a surface-marked measurement gauge.

The phantom (800) further comprises an inferior supporting element (850) configured to support the intermediate head clamp (300), and to allow rotations of the intermediate head clamp (300) relative to the phantom base (810). The inferior supporting element (850) has an axis of reference (855), which is an axis around which the intermediate head clamp (300) rotates is disposed in fixed relation to the phantom base (810). It may be disposed perpendicular to the phantom base (810). An inferior supporting element (850) is depicted in FIG. 35 (separated from the phantom base (810)) and FIGS. 37 and 38 (attached to the phantom base (810)). The inferior supporting element (850) comprises a main body (854) having superior side (858a) and opposing inferior side (858b). The superior side (858a) and optionally the inferior side (858b) may be planar. The inferior supporting element (850) further comprises a holding space (851) at least partially surrounded by the main body (854) dimensioned such that it could receive the head of the subject. The holding space (851) may have a span of 22-26 cm, preferably 24 cm. The holding space (851) preferably has a circular profile.

The inferior supporting element (850) main body (854) may have an anterior side (859a) that could align with the face (e.g. nasion) of the subject and an opposing posterior side (859b) that could align with the back of the head of the subject. A side opening (853) in the main body (854) may be provided for connecting the holding space to an exterior edge of the main body (854). The side opening (853) may be disposed on a posterior side of the main body (854). The side opening (853) may span a geometric segment of the circular path of the movement guide (856) that is between 55-180 deg, preferably 65 deg. The main body (854) has a height, that is a dimension parallel to the axis of reference (450) of the inferior positioning support (400); the height may be 1-3 cm.

The superior side (858a) may be disposed with a movement guide (856) configured to co-operate with the complementary movement guide (346') of the intermediate head clamp (300). An exemplary movement guide (446) is shown in FIGS. 7A and 7B and in FIG. 8. The movement guide (856) limits relative movement of the parts along to a guide path. The guide path is a circular path. Herein, a circular path includes a complete circle or a circular arc. The circular path is planar. The movement guide (856) describes a circular path of rotation. The movement guide has an axis of reference (855), which is an axis passing through the centre of the circular path and is perpendicular to a plane of the circular path, and is disposed in fixed relation to the phantom base (810).

The inferior supporting element (850)/movement guide (856) axis of reference (855) coincides with the IHC axis of reference (350). Revolute movement of the IHC (300) relative to the inferior supporting element (850)/movement guide (856) may be limited to rotations around the axis of reference (855).

An edge of the main body (854) may be disposed with a surface-marked measurement gauge or scale; the measurement gauge is for reading-out an angle setting of the intermediate head clamp (300) with respect to the inferior supporting element (850). The edge is an outside edge. The marking may be in angular degrees (e.g. 0 to 359 deg). 0 degrees may correspond to the nasion.

When both the movement guides (856, 346) of the inferior supporting element (850) and of the intermediate head clamp (300) co-operate, movement of the intermediate head clamp (300) is limited to rotation about the inferior supporting element (850), in particular around the axis of reference (855). The movement guide (856) may comprise a continuous or discontinuous protrusion or recess or edge, that couples with a complementary continuous or discontinuous recess or protrusion or surface of the complementary movement guide of the intermediate head clamp (300).

The inferior supporting element (850) may be dismountably attached or non-dismountably attached to the phantom base (810). In the case of dismountable attachment, a coupling (812a, 812b, 812c) may be provided on the phantom base (810) for dismountable attachment of the inferior supporting element (850), configured to maintain the inferior supporting element (850) in fixed positional and rotational relation to the phantom base (810). A plurality of spacers (852a, 852b, 852c) may be provided which displace the inferior supporting element (850) in a superior direction (858a) from the phantom base (810) by a fixed and known amount.

The inferior supporting element (850) may be made from any suitable material that provides the requisite strength and rigidity. The material may be non-ferrous to allow use with a medical imager. The material should also comply with the requirements of good surgical practice, e.g. be washable. It may be a sterilizable material also. Examples of suitable materials include polymers (e.g. polyethylene, polypropylene, polycarbonate, polyurethane), metals or alloys (e.g. aluminium, titanium), ceramic (silicon based), composites.

The inferior supporting element (850) movement guide (856) is dimensioned the same as the inferior positioning support (400) movement guide (446). This allows coupling of the intermediate head clamp (300) to either one of the inferior supporting element (850) or inferior positioning support (400). Alternatively, the inferior supporting element (850) main body (854) and movement guide (856) may be the same as the inferior positioning support (400) main body and movement guide (446). In particular, the inferior supporting element (850) may include the features of the inferior positioning support (400); this means that the inferior supporting element (850) can be used in both the phantom (850) and in the system (100). FIG. 38 shows the IHC (300) revolutely coupled to the inferior supporting element (850) main body (854) and movement guide (856).

The phantom (800) allows alignment of the dismountable unit (600) with the target without the need in the operating theatre for a navigational system; the joints of the IHC frame (500) and of the phantom (800) can be set manually. The position of the target body (840) is set to the position of the treatment target, based on data from a 3D medical image. In doing so, the position of the target body (840) is also set in known relation to the IHC (300).

Figure 39:
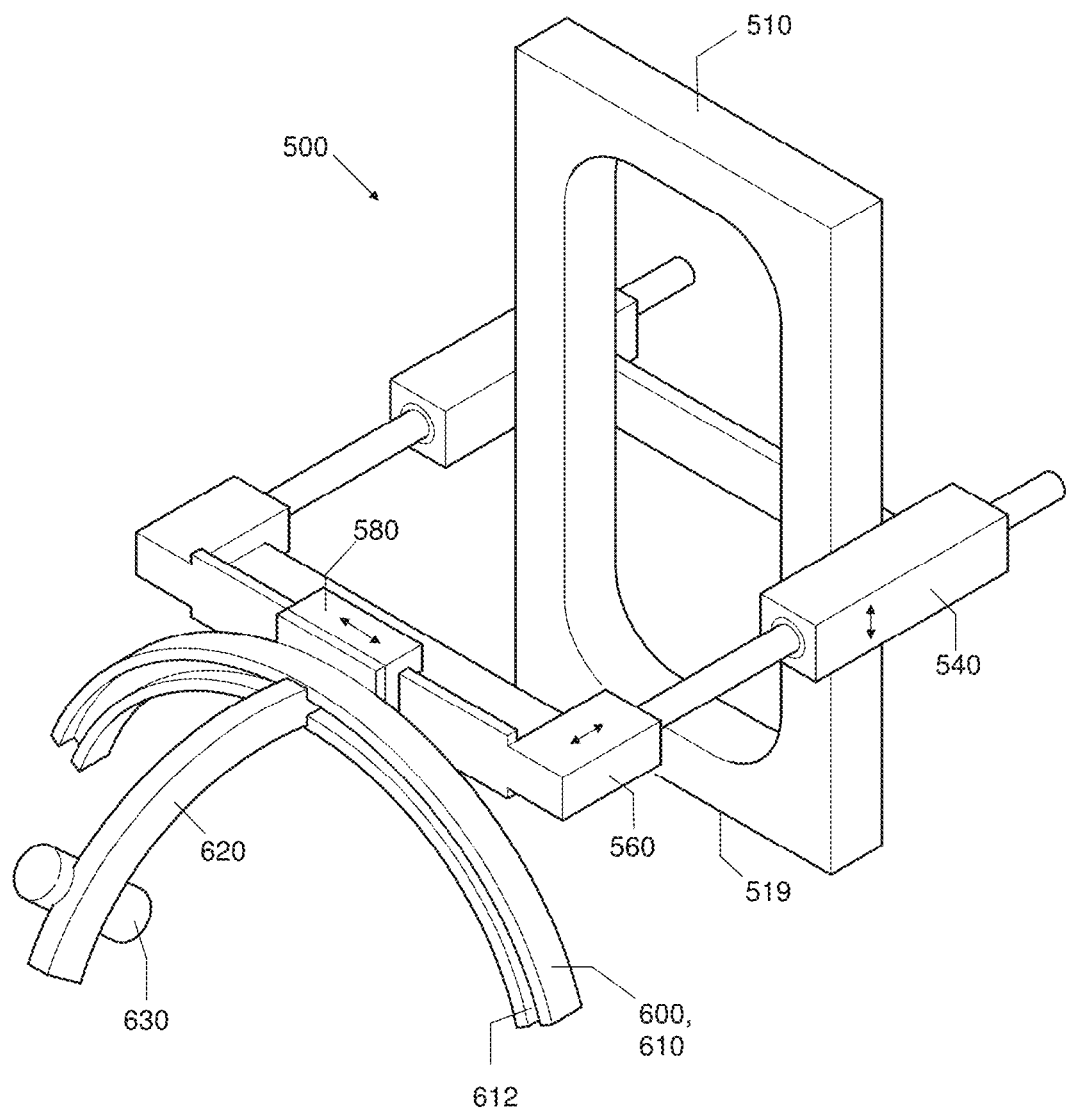
Figure 40:
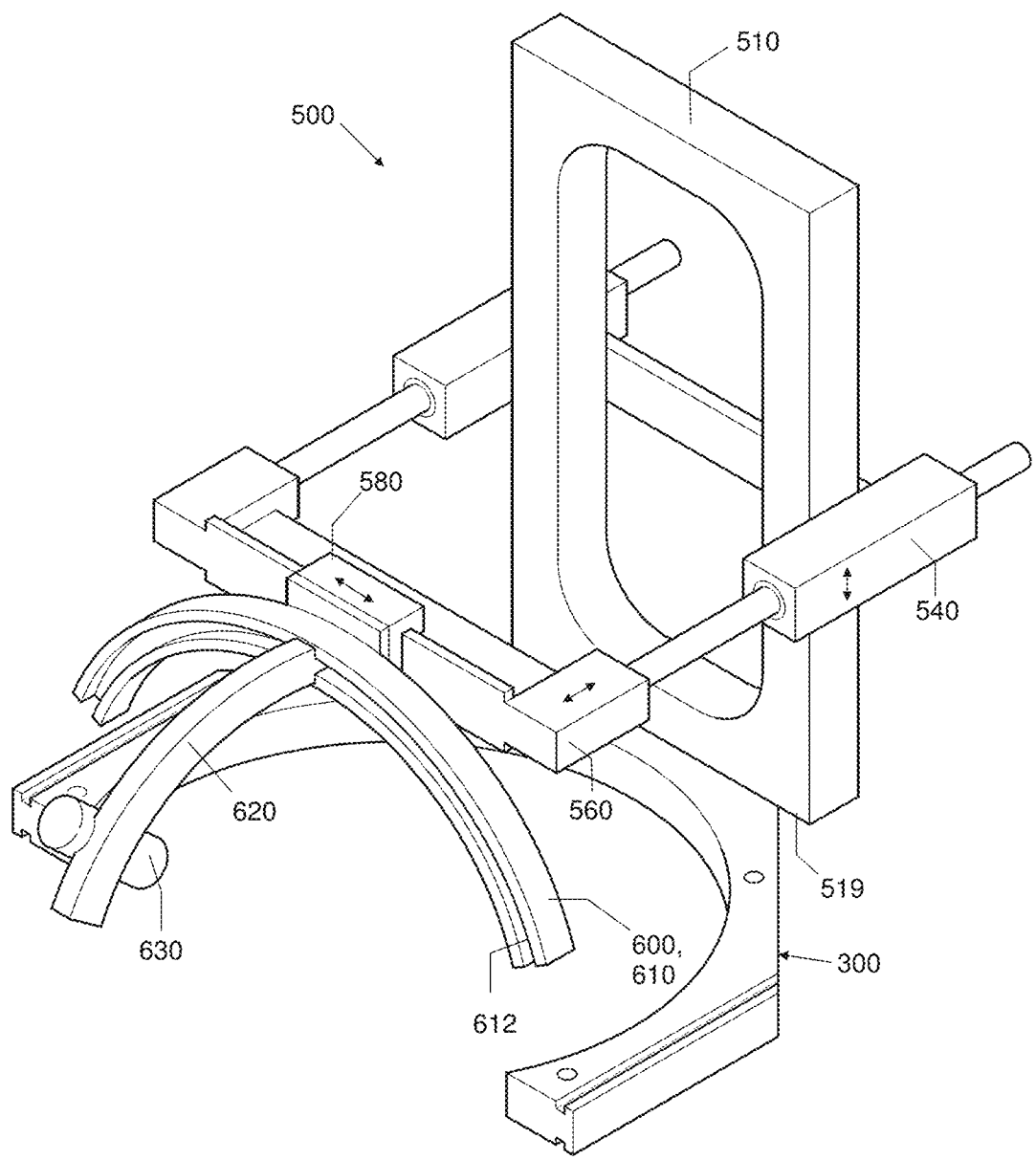

The IHC support frame base (510) is attached to the IHC (300) (at the IHC coupling (330)) so the frame base (510) is held in fixed relation to the IHC (300). FIG. 40 shows the IHC support frame base (510) of FIG. 39 disposed with a dismountable unit (600) comprising the fixed alpha arm (FAA) (610) and the beta arm (620) attached to the IHC (300). The links (540, 560, 580) are manually slidably adjustable.

Figure 41:
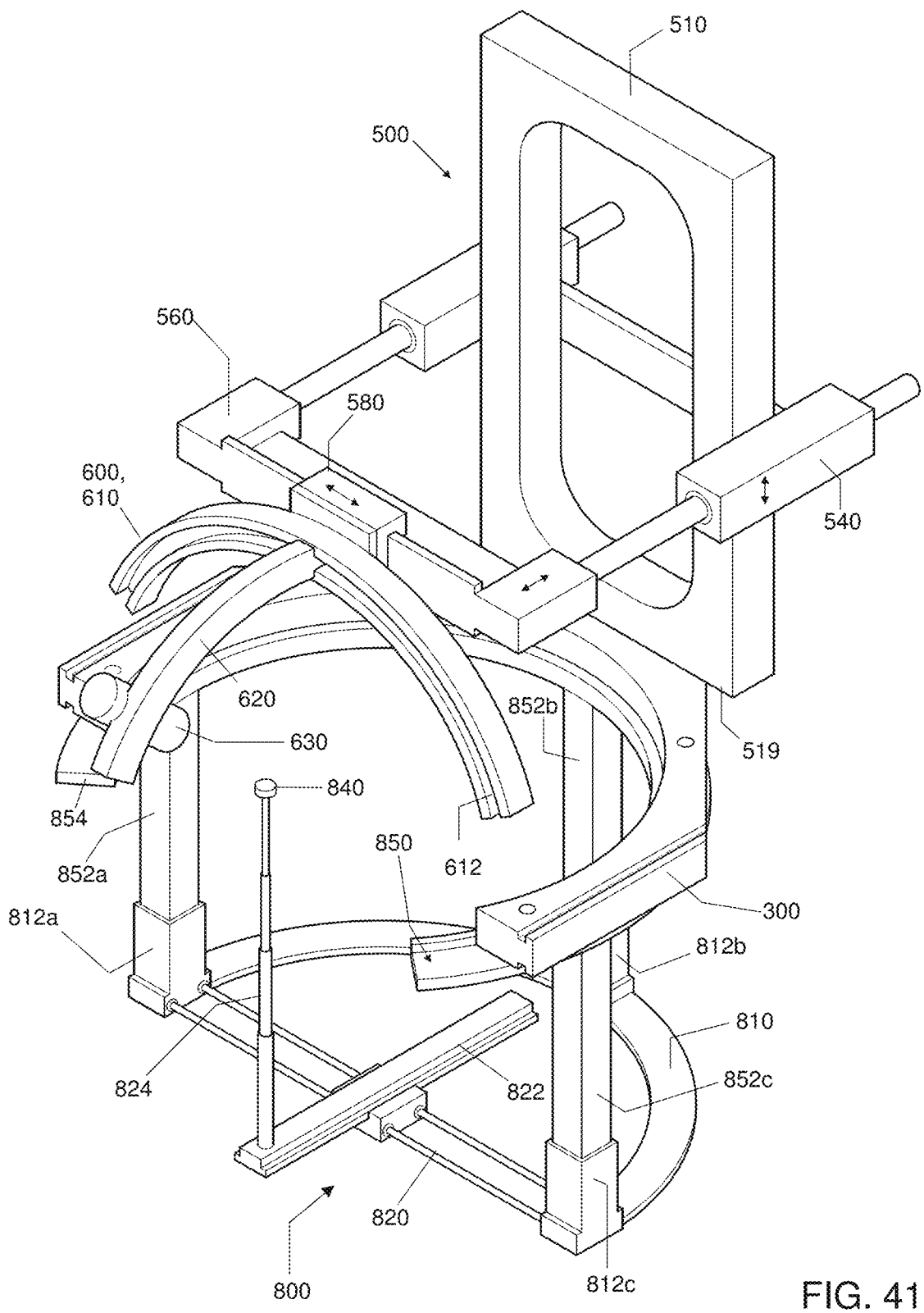

While still attached to the IHC frame (500) base (510), the intermediate head clamp (300) is revolutely coupled to the inferior supporting element (850). The revolute angle of the intermediate head clamp (300) relative to the inferior supporting element (850) may be set manually, based on data from a 3D medical image; usually the rotation is such that the target is at the zenith. FIG. 41 shows the IHC support frame (500) attached to the IHC (300), wherein the IHC (300) is revolutely coupled to the inferior supporting element (850) movement guide (856). The links (540, 560, 580) of the IHC support frame (500) are manually adjustable such that the dismountable unit (600) is, by visual inspection, aligned with the position of the target body (840). In particular, the arc centre of the fixed alpha arm (FAA) (and of the beta arm (620) supporting rail (622)) is aligned with the position of the target body (840). Once the links (540, 560, 580) are adjusted, they are fixed. The phantom (800) is removed, the intermediate head clamp (300) is detached from the IHC support frame (500).

At the appropriate time before the intervention, the intermediate head clamp (300) is accurately positioned on and fixed on the head of the subject using the system (100) described herein. The adjustable protrusions (260, a, b, c, d, e) of the superior positioning cap (200) may be set manually, based on data from a 3D medical image. The subject wearing the intermediate head clamp (300) is then placed on the operation table. The IHC frame (500) is attached to the operation table by the base (510). The IHC (300) is attached to the IHC frame (500) base (510), thereby placing the head of the subject in known fixed relation to the dismountable unit (600), whereby the dismountable unit (600) is aligned with the treatment target.

Provided is an in-vitro method for manually setting the position of the dismountable unit (600) of the IHC system relative to the intermediate head clamp (300), so that the dismountable unit (600) is aligned with the target when intermediate head clamp (300)-centred on the MCP of the subject and disposed parallel to and superior to the AC-PC line.

One method for setting the IHC system comprises:
obtaining a target body (840) dataset, comprising a plurality of (angular or distance) settings for each of the joints of the phantom (800), wherein the target body (840) dataset is determined from a (3D) medical image of the subject;
manually setting the joints (i.e. x, y, z) of the phantom (800) according to the target body dataset (thereby setting the position and optionally orientation of the target body (840) relative to the phantom base);
attaching the IHC support frame base (510) (at one or more couplings (519, a, b)) to the IHC (300) (at the IHC coupling (330)) so the frame base (510) is held in fixed relation to the IHC (300);
coupling the IHC (300) fixed to the IHC support frame base (510) to the inferior positioning support (400) fixed to the phantom (800) base (810), so the IHC (300) is rotatable around the axis of rotation (350) relative to the inferior positioning support (400);
obtaining an IHC (300) dataset, comprising an angular setting of the IHC (300) around the axis of rotation (350) relative to the inferior positioning support (400);
setting the angle of the IHC (300) relative to the inferior positioning support (400) according to the IHC (300) dataset;
manually adjusting the joints (i.e. x, y, z) of the IHC support frame (500) such that the dismountable unit (600) is, by visual inspection, aligned with the position of the target body (840).

The dismountable unit (600) may comprise the fixed alpha arm (FAA) (610); in which case the centre (718) of the arc-shaped supporting rail (612) is manually aligned with the position of the target body (840). The dismountable unit (600) may comprise one or more MMH supporting rails (720), in which case the arc centre of each rail (718) is manually aligned with the position of the target body (840).

Provided is a phantom system comprising:
a phantom (800) as described herein, and
optionally an intermediate head clamp (300) as described herein, and
optionally an IHC support frame (500) as described herein.

Provided is a method for determining placement of an intermediate head clamp (IHC) (300) configured for attachment of the head of the subject in relation to an operating table, comprising:
providing the IHC (300) configured for attachment of the head of the subject in relation to an operating table, the IHC having an arc-shaped (circle) body (310) disposed with a plurality of clamps (390, a-d) and an opening for manual access to the head,
receiving a 3D medical image of the head of the subject,
determining from the 3D medical image, a placement of the IHC such that:
a centre of the arc coincides with the MHC of the subject,
the arc is parallel with the AC-PC plane of the subject,
opening of the arc clears manual access to the target.

Preferably the opening of the arc is oriented at the zenith (±10 deg) on the operating table. The method allows the user to orient the subject head on the operating table for manual interventions.

Provided is a system for assisting head surgery comprising:
an intermediate head clamp (IHC) (300) configured for attachment of the head of the subject in relation to an operating table, the IHC having an arc-shaped (circle) body (310) disposed with a plurality of clamps (390, a-d) and an opening for manual access to the head,
a calculating unit, configured to
determine, from a 3D medical image, a placement of the IHC (300) on the head of the subject such that:
the centre of the arc coincides with the MHC of the subject,
the arc is parallel with the AC-PC plane of the subject,
opening of the arc clears access to the target
opening of the arc is oriented at the zenith (±10 deg) on the operating table configured to output an angle (gamma) that is set using the system (100) described herein.

The calculating unit may be a person or machine.

Provided is a method for configuring a phantom system comprising:
providing the IHC (300) configured for attachment of the head of the subject in relation to an operating table, the IHC having an arc-shaped (circle) body (310) disposed with a plurality of clamps (390, a-d) and an opening for manual access to the head,
receiving a 3D medical image of the head of the subject,
determining from the 3D medical image:
the Mid Commissural Point MCP (26),
the distances between the Mid Commissural Point MCP (26) skull (e.g. a, ah, h, ph, p, l, lh, rh (see FIGS. 42A, 42B)) allowing setting of the adjustable protrusions (292a-f) of the superior positioning cap (200), and
the position of the target in cartesian co-ordinates, allowing setting of the joints (i.e. x, y, z) of the phantom (800),
entry point/target point angle (EP) on the skull, allowing setting of the intermediate head clamp (IHC) (300) so that the side opening (324) is aligned with the Entry Point/Target Point.

Further steps may include:
On the phantom (800) setting the position of the target body (540) using the cartesian co-ordinates (i.e. x, y, z);
Coupling the dismountable inferior supporting element (850) (that is an inferior positioning support (400)) to the Intermediate head clamp (300), rotate the Intermediate head clamp (300) until angle EP is set; fixing the angle EP
Mounting the inferior supporting element (850) to the base of the phantom (800);
Attaching the Intermediate head clamp (300) (still coupled with the phantom (800) inferior supporting element (850)) to the IHC support frame (500); and
Adjusting the moveable member (580) and hence dismountable unit (600) of the IHC support frame (500) until the dismountable unit (600) is aligned with the target. Fixing the position of the moveable member (580).

Further steps may include:
Removing the IHC support frame (500) from the Intermediate head clamp (300) fixed to the inferior supporting element (850) (that is an inferior positioning support (400));
Dismounting the inferior supporting element (850) (that is an inferior positioning support (400)) from the base of the phantom (800);
Setting the depths of the depth of the adjustable protrusions (292a-f) of the superior positioning cap (200) based on the distances between the Mid Commissural Point MCP (26) skull (e.g. a, ah, h, ph, p, l, lh, rh (see FIGS. 42A, 42B));
Coupling the superior positioning cap (200) to the intermediate head clamp (300) fixed to the inferior supporting element (850) (that is an inferior positioning support (400));
Mounting on head (16) of the subject;
Deploying intermediate head clamp (300) clamps (390, a-d) to fix the intermediate head clamp (300) at the set pose to the head (16) of the subject;
Removing the superior positioning cap (200) and inferior supporting element (850)
Fixing the intermediate head clamp (300) (and subject) to the operation table (e.g. via a Mayfield device);
Fixing the IHC support frame (500) to the intermediate head clamp (300) and so the operation table (e.g. via the Mayfield device);
Starting the intervention.

LIST OF MAIN ABBREVIATIONS

IHC—intermediate head clamp (300)
SPC—superior positioning guide (200)
IPS—inferior positioning support (400)
SOB—side opening bride (3010)
AC-PC line—anterior commissure-posterior commissure line (30)
MCP—mid commissural point (26)
DOF—degree of freedom
FAA—fixed alpha arm (610)
BA—beta arm (620)
MM—moveable member (580)
MMH—moveable member hub (710, a, b)

What is claimed is:

1. A system for positioning an intermediate head clamp on a subject for medical interventions thereon, comprising:
a superior positioning cap configured for placement on a head of the subject having a domed receiving space for receiving a part of the head of the subject, wherein the superior positioning cap is provided with a plurality of adjustable protrusions, each configured for controlled advancement into the domed receiving space or withdrawal therefrom and for contacting the part of the head of the subject, wherein the plurality of adjustable protrusions adjusts a pose of the superior positioning cap and of an axis of reference of the superior positioning cap in relation to the head;
an intermediate head clamp, wherein the intermediate clamp comprises a main body, a holding space at least partially surrounded by the main body dimensioned to receive the head of the subject, a plurality of clamps each configured for advancement into the holding space or withdrawal therefrom and for contacting the part of the head of the subject, wherein deployment of the plurality of clamps fixes a pose of the main body relative to the head of the subject; and an inferior positioning support comprising a main body configured for placement around the head of the subject in a region coinciding with a forehead, and a plurality of locating bodies each for locating in and engaging with a bodily recess of the subject's head and each locating body being attached in adjustable and fixable in positional relation to the main body of the inferior positioning support, wherein the plurality of locating bodies adjusts a pose of the inferior positioning support and of an axis of reference of the inferior positioning support in relation to the head, wherein the superior positioning cap and inferior positioning support are configured to flank and each engage with the intermediate head clamp such that the axes of reference of the superior positioning cap and of the inferior positioning support are co-axial, and the intermediate head clamp is rotatable around an axis of rotation co-axial with the axes of reference of the superior positioning cap and of the inferior positioning support.

2. The system according to claim 1, wherein each of the superior positioning cap, and inferior positioning support comprises a movement guide configured to co-operate with a complementary movement guide disposed respectively on superior and inferior sides of the intermediate head clamp, the movement guides having a circular or arc path centred on the coaxial arrangement of the axes of reference and axis of rotation.

3. The system according to claim 1, wherein the intermediate head clamp is provided with at least one intermediate head clamp hub configured for dismountable attachment of at least one arc-shaped intermediate head clamp supporting rail, wherein the intermediate head clamp hub is configured to allow rotation of the intermediate head clamp supporting rail around a rail axis of rotation that crosses the axis of rotation of the intermediate head clamp.

4. The system according to claim 1, wherein the intermediate head clamp main body is provided with a side opening connecting the holding space to an exterior edge of the main body.

5. The system according to claim 4, further comprising a side-opening bridge configured for dismountable attachable to the intermediate head clamp body across the side opening, wherein the side-opening bridge is provided with a side-opening bridge supporting rail having an arc-shape and having an arc centre coinciding with the axis of rotation of the intermediate head clamp.

6. The system according to claim 5, further comprising a further side-opening bridge supporting rail configured for slidable attachment to the side-opening bridge supporting rail, wherein the further side-opening bridge supporting rail has an arc-shape having an arc centre coinciding with the arc centre of the side-opening bridge supporting rail, and wherein the arcs of the side-opening bridge supporting rail and of the further side-opening bridge supporting rail are perpendicular.

7. The system according to claim 6, further comprising an instrument holder slidably attached to the further side-opening bridge supporting rail, the instrument holder configured to fix an instrument direction to coincide with the axis of rotation of the intermediate head clamp.

8. The system according to claim 6, further comprising a marking arc attached at one end rotatably to the further side-opening bridge supporting rail, such that a centre of the marking arc crosses the axis of rotation of the intermediate head clamp, wherein an instrument holder is slidably attached to the marking arc, the instrument holder configured to fix an instrument direction to coincide with the axis of rotation of the intermediate head clamp.

* * * * *